(12) United States Patent
Wang et al.

(10) Patent No.: US 7,208,311 B2
(45) Date of Patent: Apr. 24, 2007

(54) CATALYTIC DOMAIN OF ADAM33 AND METHODS OF USE THEREOF

(75) Inventors: Wenyan Wang, Edison, NJ (US); Hung V. Le, Rockaway, NJ (US); Jian-Jun Liu, Parlin, NJ (US); Vincent S. Madison, Mountain Lakes, NJ (US); Winifred W. Prosise, Ramsey, NJ (US); Shahriar Shane Taremi, Upper Montclair, NJ (US); Li Xiao, Woodbridge, NJ (US); Jun Zou, Cranbury, NJ (US)

(73) Assignee: Schering Corporation, Kenilworth, NJ (US)

( * ) Notice: Subject to any disclaimer, the term of this patent is extended or adjusted under 35 U.S.C. 154(b) by 224 days.

(21) Appl. No.: 10/741,204

(22) Filed: Dec. 19, 2003

(65) Prior Publication Data

US 2004/0151715 A1 Aug. 5, 2004

Related U.S. Application Data

(60) Provisional application No. 60/440,263, filed on Jan. 15, 2003, provisional application No. 60/434,830, filed on Dec. 19, 2002, provisional application No. 60/434,802, filed on Dec. 19, 2002.

(51) Int. Cl.
*C12N 9/64* (2006.01)
*C12N 15/12* (2006.01)
*C12N 15/57* (2006.01)
*C12N 15/79* (2006.01)

(52) U.S. Cl. .................. 435/226; 435/69.1; 435/252.3; 435/320.1; 435/471

(58) Field of Classification Search ...................... None
See application file for complete search history.

(56) References Cited

U.S. PATENT DOCUMENTS

| | | | | |
|---|---|---|---|---|
| 5,830,742 | A | 11/1998 | Black et al. | 435/226 |
| 6,013,466 | A | 1/2000 | Black et al. | 435/23 |
| 6,420,154 | B1 | 7/2002 | Sheppard et al. | 435/212 |
| 6,683,165 | B1 * | 1/2004 | Keith et al. | 536/22.1 |
| 6,762,044 | B2 * | 7/2004 | Sheppard et al. | 435/212 |
| 6,927,056 | B2 * | 8/2005 | Todd et al. | 435/226 |
| 2002/0172670 | A1 * | 11/2002 | Rose et al. | 424/94.61 |
| 2003/0138925 | A1 * | 7/2003 | Keith et al. | 435/183 |
| 2003/0235882 | A1 * | 12/2003 | Shimkets et al. | 435/69.1 |
| 2004/0002470 | A1 | 1/2004 | Keith et al. | |
| 2004/0018970 | A1 * | 1/2004 | Shimkets et al. | 514/12 |
| 2004/0023215 | A1 | 2/2004 | Keith et al. | |
| 2004/0077011 | A1 | 4/2004 | Keith et al. | |
| 2004/0091473 | A1 * | 5/2004 | DuBose et al. | 424/94.63 |
| 2004/0152869 | A1 | 8/2004 | Zhang et al. | |
| 2004/0157309 | A1 | 8/2004 | Orth et al. | |

FOREIGN PATENT DOCUMENTS

WO WO 03/031594 A2 4/2003

OTHER PUBLICATIONS

Yamamoto-Katayama, S., et al., 2001, "Site-directed removal of N-glycosylation sites in BST-1/CD157: Effects on molecular and functional heterogeneity", Biochemical Journal, vol. 357, pp. 385-392.*
Armour, Augustin, et al., "The enzymatic activity of ADAM8 and ADAM9 is not regulated by TIMPs," FEBS Letters 524:154-8 (2002).
Black, Roy A., et al., "A metalloproteinase disintegrin that releases tumour-necrosis factor-α from cells," Nature 385:729-33 (1997).
Bottomley, Kevin M., et al., "Matrix metalloproteinases and the potential therapeutic role for matrix metalloproteinase inhibitors in Chronic Obstructive Pulmonary Disease (COPD)," Annual Reports in Medicinal Chemistry 37:209-16 (2002).
Coombs, Gary S., et al., "Substrate specificity of prostate-specific antigen (PSA)," Chemistry & Biology 5:475-488 (1998).
Drazen, Jeffrey M., et al., "Inherit the wheeze," Nature 418:383-4 (2002).
Fernandez-Catalan, Carlos, et al., "Crystal structure of the complex formed by the membrane type 1-matrix metalloproteinase with the tissue inhibitor of metalloproteinase-2, the soluble progelatinase A receptor," The EMBO Journal 17:5238-48 (1998).
Gearing, A.J.H., et al., "Processing of tumor necrosis factor-α precursor by metalloproteinases," Nature 370:555-7 (1994).
Gomis-Rüth, Franz-Xaver, et al., "Mechanism of inhibition of the human matrix metalloproteinase stromelysin-1 by TIMP-1," Nature 389:77-81 (1997).
Gunn, Teresa M., et al., "Identification and preliminary characterization of mouse *Adam33*," BMC Genetics 3:1-8 (2002).
Hogate, ST, et al., "ADAM 33: just another asthma gene or a breakthrough in understanding the origins of bronchial hyperresponsiveness?" Thorax 58:466-9 (2003).
Houghten, Richard A., et al., "Generation and use of synthetic peptide combinatorial libraries for basic research and drug discovery," Nature 354:84-6 (1991).

(Continued)

Primary Examiner—Nashaat T. Nashed
Assistant Examiner—William W. Moore

(57) ABSTRACT

The present invention discloses purified polypeptides that comprise an active ADAM33 catalytic domain. In addition, the present invention discloses nucleic acids that encode the polypeptides of the present invention. The present invention also discloses methods of growing X-ray diffractable crystals of polypeptides comprising the active ADAM33 catalytic domain. In addition, the present invention discloses methods of using the X-ray diffractable crystals of ADAM33 in structure-based drug design to identify compounds that can modulate the enzymatic activity of ADAM33. The present invention also discloses methods of treating respiratory disorders by administering therapeutic amounts of the ADAM33 catalytic domain.

10 Claims, No Drawings

OTHER PUBLICATIONS

Lee, Meng-Huee, et al., "Mapping and characterization of the functional epitopes of tissue inhibitor of metalloproteinases (TIMP)-3 using TIMP-1 as the scaffold: A new frontier in TIMP engineering," *Protein Science* 11:2493-2503 (2002).

Lind, Denise L., et al., "*ADAM33* is not associated with asthma in Puerto Rican or Mexican Populations," *American Journal of Respiratory and Critical Care Medicine* 168:1312-16 2003).

Maskos, Klaus, et al., "Crystal structure of the catalytic domain of human tumor necrosis factor-α-converting enzyme," *Proc. Natl. Acad. Sci.* 95:3408-12 (1998).

Matthews, David J., et al., "Substrate phage: selection of protease substrates by monovalent phage display," *Science* 260:1113-7 (1993).

Matthews, David J., et al., "A survey of furin substrate specificity using substrate phage display," *Protein Science* 3:1197-1205 (1994).

McGeehan, Gerard M., et al., "Regulation of tumour necrosis factor-α processing by a metalloproteinase inhibitor," *Nature* 370:558-61 (1994).

Milla, Marcos E., et al., "Specific sequence elements are required for the expression of funcional tumor necrosis factor-α-converting enzyme (TACE)," The Journal of Biological Chemistry 274:30563-70 (1999).

Mohan, Mohita J., et al., "The tumor necrosis factor-α converting enzyme (TACE): a unique metalloproteinase with highly defined substrate selectivity," *Biochemistry* 41:9462-69 (2002).

Mohler, Kendall M., et al., "Protection against a lethal dose of endotoxin by an inhibitor of tumour necrosis factor processing," *Nature* 370:218-220 (1994).

Morgunova, Ekaterina, et al., "Structure of human pro-matrix metalloproteinase-2: activation mechanism revealed," *Science* 284:1667-70 (1999).

Morris, David G., et al., "Loss of integrin αvβ6-mediated TGF-β activation causes Mmp12-dependent emphysema," *Nature* 422:169-73 (2003).

Nagase, Hideaki, "Activation Mechanisms of Matrix Metalloproteinases," *Biol. Chem.* 378:151-160 (1997).

Nagase, Hideaki, et al., "Matrix metalloproteinases," *The Journal of Biological Chemistry* 274:21491-4 (1999).

Orth, Peter, et al. "Crystal structure of the catalytic domain of human ADAM33," *J. Mol. Biol.* 335:129-37 (2004).

Polgár, László, "Metalloproteases," Mechanisms of Protease Action, CRC Press, Inc., Boca Raton, Florida pp. 183-218 (1989).

Postma, D.S., et al., "*ADAM33* gene: confirming a gene without linkage," *Clin. Exp. Allergy* 34:1-3 (2004).

Roberts, Anita B., "Smoke signals for lung disease," *Nature* 422:130-1 (2003).

Shapiro, Steven D., et al., "*ADAM-33* Surfaces as an Asthma Gene," *N Engl J Med* 347:936-8 (2002).

Smutzer, Gregory, "Molecular Demolition," *The Scientist* 16:34 (2002).

Turk, Benjamin E., et al., "Determination of protease cleavage site motifs using mixture-based oriented peptide libraries," *Nature Biotechnology* 19:661-7 (2001).

Van Eerdewegh, Paul, et al., "Association of the *ADAM33* gene with asthma and bronchial hyperresponsiveness," *Nature* 418:426-30 (2002).

Werner, M., et al., "Asthma is associated with single-nucleotide polymorphisms in *ADAM33*," *Clin Exp Allergy* 34:26-31 (2004).

Yoshinaka, Tsuyoshi, et al., "Identification and characterization of novel mouse and human ADAM33s with potential metalloprotease activity," *Gene* 282:227-36 (2002).

Prosise et al., Protease domain of human ADAM33 produced by Drosophila S2 cells. Protein Expr Purif. Dec. 2004;38(2):292-301.

Orth et al., Crystal structure of the catalytic domain of human ADAM33. J Mol Biol. Jan. 2, 2004;335(1):129-37.

* cited by examiner

US 7,208,311 B2

CATALYTIC DOMAIN OF ADAM33 AND METHODS OF USE THEREOF

This application claims the benefit of U.S. Provisional Applications 60/434,830, filed Dec. 19, 2002, 60/434,802, filed Dec. 19, 2002, and 60/440,263, filed Jan. 15, 2003. These applications are hereby incorporated by reference in their entirety.

FIELD OF THE INVENTION

The present invention pertains to a catalytic domain of a protein that is characterized by having a disintegrin and metalloprotease domain (ADAM). The present invention also pertains to a process of obtaining specific samples of this catalytic domain that are amenable to forming homogenous crystals for X-ray crystallization analysis.

BACKGROUND OF THE INVENTION

Asthma is a chronic respiratory disorder that afflicts hundreds of millions of people throughout the world [Drazen and Weiss, *Nature* 418:383–384 (2002)]. Though the occurrence of this respiratory disorder has been noted for over two thousand years, during the past twenty years industrialized nations have experienced an increase in asthma sufferers that approaches epidemic proportions [Umetsu et al., *Nature Immunology* 3:715–720 (2002)]. Indeed, 10–20% of the population of industrialized countries currently suffers from asthma. Not surprisingly, the dramatic increase in the number of asthmatics in industrialized nations has resulted in a concomitant expenditure of resources to treat this condition [Umetsu et al., *Nature Immunology* 3:715–720 (2002)]. Despite this strong commitment, to date the treatments employed only control the symptoms.

Asthma is characterized by life-threatening attacks due to episodic obstructions to, or abnormal narrowing of the airways in response to otherwise innocuous stimuli [Drazen and Weiss, *Nature* 418:383–384 (2002)].

Common symptoms of asthma include recurrent episodes of coughing, wheezing and breathlessness. The immediate cause for the thickening of the airway walls, smooth muscle contraction, and narrowing of the airways observed in asthmatics is an inflammation mediated by T-cells [Van Eerdewegh et al., *Nature* 418:426–430 (2002)]. Both genetic and environmental factors play key roles in inducing this T-cell-mediated inflammation, though the actual mechanism has yet to be delineated. What is known is that asthmatics have a genetic predisposition for the disease, and environmental factors serve to either trigger or protect against this immunological dysregulation [Umetsu et al., *Nature Immunology* 3:715–720 (2002)].

Recently, the gene encoding a membrane anchored protein known as ADAM33 has been shown to be linked to asthma by positional cloning in an outbred population [Van Eerdewegh et al., *Nature* 418:426–430 (2002)]. ADAM33 is a member of the "A Disintegrin And Metalloprotease" (ADAM) family of proteins which comprises over thirty such proteins, including the well characterized ADAM17, the TNF-α converting enzyme (TACE) [Cross et al., *J. Am. Chem. Soc.* 124:11004–11007 (2002); Schlondorff and Blobel, *J. Cell Sci.*, 112:3603–3617 (1999); Black, *Intern. J. Biochem. Cell Biol* 34:1–5 (2002); U.S. Pat. No. 5,830,742]. The ADAM family of proteins is a class of type-I transmembrane proteins that share a unique domain structure composed of a signal sequence, a pro domain, a metalloprotease/catatlytic domain, a disintegrin domain, a cysteine-rich domain, an epidermal growth factor-like domain, a transmembrane and a cytoplasmic domain.

U.S. Pat. No. 6,420,154 B1 discloses a human nucleic acid sequence that subsequently was shown to encode ADAM33, along with the corresponding amino acid sequence. Others also have disclosed human and mouse ADAM33 nucleic acid and amino acid sequences [Yoshinaka et al., *Gene* 282:227–236 (2002); Gunn et al., BMC Genetics 3:2 1–8, (2002)]. However, little specific information has been provided regarding the catalytic activity of ADAM33. Moreover, heretofore, the ADAM33 protein domains, including the catalytic domain, had not been specifically delineated and isolated.

Due to its genetic linkage to asthma, ADAM33 has become a promising target protein for use in identifying pharmaceuticals to treat asthma [Shapiro and Owen, *N Engl J Med* 347:936–938 (2002)]. Structure-based drug design is one way to optimize the success of such drug discovery. However, use of this powerful methodology requires the three-dimensional structure of the target protein and, heretofore, little to no information has been provided regarding the three-dimensional structure of ADAM33. This is in sharp contrast with other Zinc dependent metalloproteases such as Adamalysin II, [Gomis-Ruth et al., *Protein Science* 7:283–292 (1998)] and TACE, [Letavic et al., *Biorgan. & Medic. Chem Lett.* 12:1387–1390 (2002); WO9940182] for which three-dimensional structures have been determined. Indeed, the current inability to generate X-ray diffractable crystals of ADAM33 and/or of its catalytic domain has greatly hampered efforts for obtaining the requisite structural information necessary to perform structure-based drug design on this protease.

Therefore, there is a need to define the nucleic acid and amino acid sequences of the catalytic domain of ADAM33. Moreover, there is a need to prepare nucleic acid constructs that encode the ADAM33 catalytic domain. In addition, there is a need to design purification procedures that lead to the preparation of isolated active ADAM33 protein and/or fragments thereof. Furthermore, there is a need to obtain ADAM33 protein samples that are amenable to forming homogenous crystals for X-ray crystallization analyses. In addition, there is a need to obtain X-ray diffractable crystals of the ADAM33 catalytic domain of sufficient quality for X-ray crystallization analyses.

The citation of any reference herein should not be construed as an admission that such reference is available as "prior art" to the instant application.

SUMMARY OF THE INVENTION

The present invention provides purified and/or recombinant polypeptides that comprise an ADAM33 catalytic domain or an active fragment thereof. Preferably, the polypeptides of the present invention retain the catalytic activity of ADAM33. These polypeptides have many uses including in assays to identify compounds that modulate the activity of ADAM33. The present invention further provides nucleic acids that encode the polypeptides of the present invention. In addition, the present invention provides methods for producing a catalytic domain of a zinc metalloprotease, such as ADAM33, that is free of its pro domain. Moreover, the present invention provides a method of treating respiratory disorders by administering a therapeutic amount of the ADAM33 catalytic domain.

In a particular aspect of the present invention, a monodisperse protein preparation of a polypeptide that comprises a modified ADAM33 catalytic domain is provided. In a preferred embodiment of this type the polypeptide is amenable to being crystallized. The present invention further provides crystals that comprise the modified ADAM33 catalytic domain, corresponding protein-ligand binding complexes, and corresponding protein-ligand binding complexes that have had their initial ligand replaced with a substitute ligand.

More particularly, the present invention provides a polypeptide consisting essentially of SEQ ID NO: 4. In one particular embodiment the present invention provides a polypeptide consisting essentially of SEQ ID NO: 4 having a conservative amino acid substitution. The present invention further provides an active, purified and/or recombinant polypeptide consisting of an ADAM33 catalytic domain having the amino acid sequence of SEQ ID NO: 4. The present invention further provides active fragments of the ADAM33 catalytic domain. Chimeric proteins comprising a wild type ADAM33 catalytic domain or active fragments thereof are also provided by the present invention.

The present invention also provides an active, purified and/or recombinant polypeptide comprising a modified ADAM33 catalytic domain. In one such embodiment, the polypeptide comprises a modified ADAM33 catalytic domain that has at least 80% identity with the amino acid sequence of SEQ ID NO: 14. Preferably the modified ADAM33 catalytic domain has at least 90% identity with the amino acid sequence of SEQ ID NO: 14. More preferably the modified ADAM33 catalytic domain has at least 95% identity with the amino acid sequence of SEQ ID NO: 14. Most preferably, these polypeptides catalyze the proteolytic cleavage of a peptide comprising the amino acid sequence of SEQ ID NO: 35 and/or bind to marimastat, N4-[2,2-dimethyl-1(S)-[(methylamino)carbonyl]propyl]-N1,2(S)-dihydroxy-3(R)-(2-methylpropyl) butanediamide.

In one such embodiment the modified ADAM33 catalytic domain comprises the amino acid sequence of SEQ ID NO: 6. In another embodiment the modified ADAM33 catalytic domain comprises the amino acid sequence of SEQ ID NO: 8. In yet another embodiment the modified ADAM33 catalytic domain comprises the amino acid sequence of SEQ ID NO: 10. In still another embodiment the modified ADAM33 catalytic domain comprises the amino acid sequence of SEQ ID NO: 12. In yet another embodiment the modified ADAM33 catalytic domain comprises the amino acid sequence of SEQ ID NO: 14. In still another embodiment the modified ADAM33 catalytic domain comprises the amino acid sequence of SEQ ID NO: 16. Any of these amino acid sequences can further comprise a conservative amino acid substitution. The present invention further provides corresponding polypeptides consisting essentially of, and/or consisting of, these modified ADAM33 catalytic domains.

In another embodiment, the invention provides a ADAM33 polypeptide that comprises one or more amino acid modifications in its pro domain. In some embodiments, the modified ADAM33 polypeptides comprise one or more amino acid substitutions selected from the group consisting of C131A, C179A, K176I and D183N. In another embodiment, the invention provides a single chain zymogen form of ADAM33, e.g. an ADAM33 comprising the R203T/R207S modifications.

The present invention also provides active fragments of the modified ADAM33 catalytic domain. The present invention further provides a full-length ADAM33 protein or fragment thereof that comprises the ADAM33 modified catalytic domain and/or comprises fragments of the modified ADAM33 catalytic domain. In one such embodiment the ADAM33 protein comprises the ADAM33 pre domain, the ADAM33 pro domain, and a modified ADAM33 catalytic domain. In another embodiment, the fragment of the ADAM33 polypeptide consists of the ADAM33 pro domain and the modified ADAM33 catalytic domain.

In addition, the present invention provides chimeric proteins comprising the modified ADAM33 catalytic domains and chimeric proteins comprising the active fragments of the modified ADAM33 catalytic domains. In a preferred embodiment the chimeric protein consists of the amino acid sequence of SEQ ID NO: 38.

In another embodiment, the chimeric ADAM33 is a fusion protein comprising the ADAM33 pre domain, the ADAM33 pro domain, the modified catalytic domain and a polyhistidine Tag. In a preferred embodiment, the chimeric ADAM33 is a fusion protein comprising the *Drosophila* Bip pre domain, the ADAM33 pro domain, the modified catalytic domain and a polyhistidine Tag. In yet another embodiment, the chimeric protein comprises the modified ADAM33 catalytic domain and a polyhistidine Tag. In a preferred embodiment, the polyhistidine Tag further comprises a seryl-glycyl- (i.e., Ser-Gly) linker, and has the amino acid sequence of SEQ ID NO:36.

The present invention further provides isolated and/or recombinant nucleic acids that encode all of the polypeptides, including the chimeric proteins, of the present invention. These nucleic acids can further comprise heterologous nucleotide sequences. In one embodiment, the nucleic acid encodes a polypeptide having the amino acid of SEQ ID NO: 4. In a particular embodiment of this type the nucleic acid comprises the nucleotide sequence of SEQ ID NO: 3. In another embodiment the nucleic acid encodes a polypeptide comprising the amino acid sequence of SEQ ID NO: 6. In a particular embodiment of this type the nucleic acid comprises the nucleotide sequence of SEQ ID NO: 5. In a preferred embodiment the nucleic acid encodes a polypeptide comprising the amino acid sequence of SEQ ID NO: 8. In a particular embodiment of this type the nucleic acid comprises the nucleotide sequence of SEQ ID NO: 7. In still another embodiment the nucleic acid encodes a polypeptide comprising the amino acid sequence of SEQ ID NO: 10. In a particular embodiment of this type the nucleic acid has the nucleotide sequence of SEQ ID NO: 9. In yet another embodiment the nucleic acid encodes a polypeptide comprising the amino acid sequence of SEQ ID NO: 11. In a particular embodiment of this type the nucleic acid comprises the nucleotide sequence of SEQ ID NO: 12. In still another embodiment the nucleic acid encodes a polypeptide comprising the amino acid sequence of SEQ ID NO: 14. In a particular embodiment of this type the nucleic acid has the nucleotide sequence of SEQ ID NO: 13. In yet another embodiment the nucleic acid encodes a polypeptide comprising the amino acid sequence of SEQ ID NO: 16. In a particular embodiment of this type the nucleic acid comprises the nucleotide sequence of SEQ ID NO: 15. In a preferred embodiment the nucleic acid consists of the nucleotide sequence of SEQ ID NO: 1. In a related embodiment, this nucleotide sequence further comprises a heterologous nucleotide sequence.

In yet another embodiment, the present invention provides a nucleic acid that encodes a polypeptide comprising a modified ADAM33 catalytic domain that has at least 95% identity with the amino acid sequence of SEQ ID NO: 14. Preferably, the polypeptide catalyzes the proteolytic cleavage of a peptide comprising the amino acid sequence of SEQ ID NO: 35 and/or binds to N4-[2,2-dimethyl-1(S)-[(methylamino)carbonyl]propyl]-N1,2(S)-dihydroxy-3(R)-(2-methylpropyl) butanediamide.

In a particular embodiment a nucleic acid encodes a polypeptide comprising an ADAM33 pro domain and an ADAM33 catalytic domain. In one such embodiment, the nucleic acid consists of the nucleotide sequence of SEQ ID NO: 29. In another embodiment the nucleic acid comprises the nucleotide sequence of SEQ ID NO: 31. In yet another embodiment the nucleic acid comprises the nucleotide sequence of, SEQ ID NO: 33. Preferably, when these sequences encode a modified ADAM33 catalytic domain, the amino acid residue encoded at the position 231 is a glutamine in place of the wild type asparagine. In addition, these sequences can further comprise a heterologous nucleotide sequence that encodes a secretion signaling sequence. In one such embodiment the secretion signaling sequence has the amino acid sequence of SEQ ID NO: 22. In another embodiment the secretion signaling sequence has the amino acid sequence of SEQ ID NO: 23. In still another embodiment the secretion signaling sequence has the amino acid sequence of SEQ ID NO: 24. In yet another embodiment the secretion signaling sequence has the amino acid sequence of SEQ ID NO: 25. In still another embodiment the secretion signaling sequence has the amino acid sequence of SEQ ID NO: 26. In yet another embodiment the secretion signaling sequence has the amino acid sequence of SEQ ID NO: 27. In still another embodiment, the secretion signaling sequence has the amino acid sequence of SEQ ID NO: 28. The heterologous nucleotide sequences of these nucleic acids can further encode a C-terminal Ser-Gly His$_6$ Tag (SEQ ID NO: 36).

The present invention further provides expression vectors that can comprise any of the nucleic acids of the present invention and a transcriptional control sequence. Preferably the nucleic acids of the present invention are operatively linked to a transcriptional control sequence in the expression vectors. Host cells comprising the expression vectors are also part of the present invention.

In addition, the present invention provides methods for producing the above-mentioned polypeptides. One such embodiment comprises culturing a host cell of the present invention that expresses a nucleic acid encoding a polypeptide of the present invention thereby producing the polypeptide. Methods for purifying and/or obtaining the resulting recombinant polypeptides are also included in the present invention, as are the purified recombinant polypeptides. In a particular embodiment, 10 µM to 1 mM $Zn^{2+}$ are included during the expression of the polypeptides. In another embodiment, greater than 10 µM $Ca^{2+}$ is included during the purification and/or during protein storage. More preferably between 0.3–100 mM $Ca^{2+}$ is included during the purification and/or during protein storage. In a particular embodiment 5 mM $Ca^{2+}$ is included during the purification and/or during protein storage. In a preferred embodiment, the $Ca^{2+}$ is included in the purification and/or during storage by adding the corresponding concentration of $CaCl_2$ to the purification and/or storage buffers.

In a preferred embodiment the host cell is a *Drosophila melanogaster* Schneider 2 (S2) stable cell line. In another preferred embodiment the pro domain and the catalytic domain of the ADAM family protein are driven by the *Drosophila* metallothionein promoter (PMT) in the recombinant DNA construct. In a particular embodiment the expression of the recombinant metalloproteins is induced by $Cd^{2+}$ at the concentration of 1–25 µM, preferably in the presence of 10 µM–1 mM $Zn^{2+}$. In a preferred embodiment of this type, the induction of the PMT promoter is achieved at 10 µM $Cd^{2+}$ in the presence of 200 µM $Zn^{2+}$. In a particular embodiment, $CdCl_2$ and $ZnCl_2$ are used to supply the $Cd^{2+}$ and $Zn^{2+}$.

The present invention further provides methods of obtaining a purified form of the ADAM33 catalytic domain that comprises purifying the polypeptide produced by a method of the present invention. In addition, the purified form of the ADAM33 of the present invention is also provided.

In yet another aspect, the present invention provides a method for producing a catalytic domain of a zinc metalloprotease that is free of its pro domain. Preferably this catalytic domain is active. One such method employs an expression vector that has a nucleic acid encoding a polypeptide comprising a pro domain and a catalytic domain of a zinc metalloprotease. The nucleic acid is constructed so that the coding sequence is operatively linked to a transcriptional control sequence. The vector is placed into a host cell that is then grown in an appropriate cell culture medium. The host cell is induced to express the nucleic acid producing the polypeptide in the presence of 1 to 25 µM $Cd^{2+}$ and 10 µM to 1 mM $Zn^{2+}$. In a preferred embodiment, the transcriptional control sequence comprises a metallothionein promoter.

In a particular embodiment the host cell is a *Drosophila melanogaster* Schneider 2 (S2) cell. In a preferred embodiment of this type, the metallothionein promoter is a Drosophila metallothionein promoter. The present invention further provides methods of obtaining a purified form of a catalytic domain of a zinc metalloprotease that is free of its pro domain. One such embodiment comprises purifying the polypeptide produced by a method of the present invention. The purified form of the catalytic domain that is free of the pro domain is also provided by the present invention.

In another aspect, the invention provides assays for identifying activators or inhibitors of ADAM33. One embodiment comprises mixing a test compound with an ADAM33 catalytic domain or an active fragment thereof and an ADAM33 substrate, measuring the rate of cleavage in the presence and absence of the compound, and determining if the compound inhibits or activates cleavage of the substrate, thus identifying an inhibitor or activator, respectively. In another embodiment, compounds may be tested in this assay using a pro/cat form of ADAM33 or a single chain zymogen form of ADAM33. In another embodiment, compounds may be tested in this assay using modified forms of ADAM33.

In another aspect, the invention provides assays for identifying substrates of ADAM33. One embodiment comprises mixing a potential substrate with an ADAM33 catalytic domain or an active fragment thereof and measuring whether the test substrate is cleaved by the ADAM33 catalytic domain. In another embodiment, potential substrates may be tested in this assay using a pro/cat form of ADAM33 or a single chain zymogen form of ADAM33. In another embodiment, potential substrates may be tested in this assay using modified forms of ADAM33.

In still another aspect, the present invention provides methods of treating respiratory disorders. In a particular embodiment of this type the respiratory disorder is asthma. One such embodiment comprises administering a therapeutic amount of a polypeptide comprising an ADAM33 catalytic domain or an active fragment thereof of the present invention to a subject with respiratory disorder, e.g., asthma. In another embodiment polypeptide being administered consists essentially of an ADAM33 catalytic domain or an active fragment thereof. In still another embodiment the polypeptide consists of an ADAM33 catalytic domain or an active fragment thereof. In a particular embodiment, the polypeptide administered is in a crystalline form.

In one particular embodiment of this type the administering is performed by intramuscular injection or infusion of the polypeptide into the subject. In another embodiment the administering is performed by subcutaneous injection or infusion of the polypeptide into the subject. Preferably the polypeptide is a recombinant polypeptide. In an alternative embodiment the administering is performed by introducing a vector into the subject as part of a gene therapy protocol. In this case the vector encodes a recombinant polypeptide that encodes the ADAM33 catalytic domain and the recombinant polypeptide is expressed in a therapeutic amount in the subject. In a particular embodiment of this type the vector is an adenoviral vector.

Crystals comprising a modified ADAM33 catalytic domain, and/or one of the protein-ligand complexes of the present invention, also are part of the present invention. Preferably, such crystals effectively diffract X-rays for the determination of the atomic coordinates of the protein and/or of the protein-ligand complex to a resolution of greater than 5.0 Angstroms. More preferably, a crystal of the present invention effectively diffracts X-rays for the determination of the atomic coordinates to a resolution of greater than 3.5 Angstroms. Even more preferably, a crystal of the present invention effectively diffracts X-rays for the determination of the atomic coordinates equal to or greater than 3.0 Angstroms. Still more preferably, a crystal of the present invention effectively diffracts X-rays for the determination of the atomic coordinates equal to or greater than 2.5 Angstroms, and, yet even more preferably, equal to or greater than 2.0 Angstroms. Most preferably, a crystal of the present invention effectively diffracts X-rays for the determination of the atomic coordinates equal to or greater than 1.8 Angstroms.

In a particular embodiment, the crystal comprises a modified ADAM33 catalytic domain. In another embodiment, the crystal comprises a protein-ligand binding complex. Preferably the modified ADAM33 catalytic domain catalyzes the proteolytic cleavage of a peptide comprising the amino acid sequence of SEQ ID NO: 35. More preferably, the modified ADAM33 catalytic domain also binds to the compound, N4-[2,2-dimethyl-1(S)-[(methylamino)carbonyl]propyl]-N1,2(S)-dihydroxy-3(R)-(2-methylpropyl) butanediamide. In one such embodiment, the crystal comprises a modified ADAM33 catalytic domain comprising an amino acid sequence having at least 95% identity with the amino acid sequence of SEQ ID NO: 14.

In one embodiment, the modified ADAM33 catalytic domain comprises the amino acid sequence of SEQ ID NO: 6. In a particular embodiment of this type, the modified ADAM33 catalytic domain comprises the amino acid sequence of SEQ ID NO: 8. In a preferred embodiment the modified ADAM33 catalytic domain consists essentially of the amino acid sequence of SEQ ID NO: 8. In a more preferred embodiment, the modified ADAM33 catalytic domain consists of the amino acid sequence of SEQ ID NO: 38. In a particular embodiment of this type, the crystal has the space group of $P222_1$, having unit cell dimensions of: a=53.8, b=66.1, c=96.1 Angstroms. In a related embodiment, the crystal comprises a protein-ligand binding complex with the modified ADAM33 catalytic domain.

In another aspect of the present invention, methods are provided for obtaining a crystal comprising a modified ADAM33 catalytic domain by vapor diffusion. One such embodiment comprises incubating an aliquot of a polypeptide comprising the modified ADAM33 catalytic domain in a buffered solution at pH 9.5–10.7 containing 10–40% PEG 3000 and/or PEG 8000. In a particular embodiment 0.0–0.2M sodium chloride is also included.

In another aspect, the present invention provides a crystalline form of ADAM33 that is amenable to ligand soaking experiments. This enables X-ray crystallographic structural determinations to be performed on multiple ADAM33-ligand complexes in rapid succession. The ability to rapidly generate three-dimensional structures of ADAM33-ligand complexes can be critical to the success of a structure-based drug design program. Indeed, the structural information generated using the compositions and methods of the present invention greatly facilitates the identification of new and more potent inhibitors of the ADAM33 protease. Selected inhibitors, in turn, become lead candidates in the development of drugs that will be useful for the treatment of respiratory diseases, such as asthma.

The present invention therefore, further provides methods of obtaining a crystal comprising a protein-ligand complex between a ligand and a polypeptide comprising a modified ADAM33 catalytic domain. One such method comprises incubating (e.g., soaking) an excess of a ligand with a crystal comprising a modified ADAM33 catalytic domain. In a preferred embodiment, the soaking is performed between pH 5.5 to pH 7.5. The incubation is performed under the appropriate conditions and for a sufficient time period for the ligand to form a protein-ligand complex with the ADAM33 catalytic domain. A crystal comprising the protein-ligand complex between the ligand and the modified ADAM33 catalytic domain is thus obtained.

The present invention further provides methods of obtaining a crystal comprising a protein-ligand complex between a substitute ligand and a modified ADAM33 catalytic domain. One such method comprises incubating an excess of a substitute ligand with a crystal of a protein-ligand binding complex comprising a modified ADAM33 catalytic domain and an initial ligand. The incubation is performed under the appropriate conditions and for a sufficient time period for the substitute ligand to replace the initial ligand in the protein-ligand complex. A crystal comprising the protein-ligand complex between the substitute ligand and the modified ADAM33 catalytic domain is then obtained.

In yet another aspect, the present invention provides a method for identifying an agent for use as an inhibitor of ADAM33. One such embodiment comprises obtaining a set of atomic coordinates that define the three-dimensional structure of the ADAM33 catalytic domain from a crystal of the present invention. In a related embodiment, a set of atomic coordinates that define the three-dimensional structure of the protein-ligand binding complex from a crystal of the present invention is obtained. In either case, a potential agent is then selected by performing structure-based drug design with the atomic coordinates obtained. Preferably, the selection is performed in conjunction with computer modeling.

A potential agent can be contacted with a proteolytic polypeptide that comprises the catalytic domain of ADAM33 or an active fragment thereof. The catalytic activity of the proteolytic polypeptide then can be determined in an ADAM33 activity assay. A potential agent is identified as an agent that inhibits ADAM33 when there is a decrease in the activity of the proteolytic polypeptide in the presence of the agent relative to in its absence.

In a variation of this method, the inhibitor is further contacted with one or more proteolytic polypeptides, preferably individually, that comprise a catalytic domain of an alternative ADAM family protease or an active fragment thereof. A compound is then selected as a unique ADAM33 inhibitor when the inhibitory effect of the inhibitor on the ADAM33 catalytic domain is at least two-fold greater (preferably 5–10 fold greater) than that observed for the alternative ADAM family protease in its corresponding enzyme assay.

Accordingly, it is a principal object of the present invention to provide a DNA construct that can be used to express an active ADAM33 catalytic domain.

It is a further object of the present invention to provide an active ADAM33 catalytic domain that can be used as a therapeutic agent to treat a respiratory ailment such as asthma.

It is a further object of the present invention to provide an active ADAM33 catalytic domain that can form a stable X-ray diffractable crystal.

It is a further object of the present invention to provide a method for generating an ADAM family protein or fragment thereof, e.g., ADAM33, that is pure, active and stable.

It is a further object of the present invention to provide a way to obtain multiple crystals of the ADAM33 catalytic domain each comprising a different protein-ligand complex.

It is a further object of the present invention to provide a process for exchanging the ligands of a crystalline form of a protein ligand complex containing an ADAM33 catalytic domain.

It is a further object of the present invention to provide an effective way of performing structure-based drug design with ADAM33.

It is a further object of the present invention to provide drug candidates for treating medical conditions that are linked to variant ADAM33 proteolytic activity.

It is a further object of the present invention to provide drug candidates for the treatment of asthma.

These and other aspects of the present invention will be better appreciated by reference to the following Detailed Description.

DETAILED DESCRIPTION OF THE INVENTION

The present invention provides the amino acid sequence of the ADAM33 catalytic domain, thereby enabling the design of nucleic acid constructs that encode and express polypeptides comprising ADAM33 proteolytic activity. The nucleic acid constructs designed are also provided. The present invention further provides specific induction conditions for the expression of recombinant ADAM family proteins and fragments thereof, e.g., the ADAM33 catalytic domain, which results in the proteins and protein fragments having significantly improved purity, activity and stability. In one such embodiment, a Drosophila S2 expression system is provided that facilitates the purification of polypeptides that comprise active ADAM family catalytic domains. The protein purification conditions that optimize the amount of active protein obtained are also provided.

In addition, the two N-glycosylation sites of the ADAM33 catalytic domain were identified, and the modification of one or both of the N-glycosylation sites of the ADAM33 catalytic domain made the resulting preparation of the purified polypeptide monodisperse and amenable for forming X-ray diffractable crystals.

Thus, the present invention provides a polypeptide that comprises a modified ADAM33 catalytic domain that is amenable to crystallization. The resulting crystals can be used to obtain the three-dimensional structure of the ADAM33 catalytic domain at a resolution of 1.8 Å. The present invention further provides drug development methods that apply this and related three-dimensional structural information obtained to the design and/or identification of inhibitors of ADAM33 for use in the treatment of respiratory disorders, such as asthma.

Structure-based drug design is the most efficient method of drug development. In one common paradigm, a three dimensional structure is determined for a protein, e.g., the modified ADAM33 catalytic domain, and/or a corresponding protein-ligand complex. Potential antagonists (e.g., inhibitors and/or potential drugs) of the protein are then identified and/or designed with the aid of computer modeling [Bugg et al., Scientific American, Dec.: 92–98 (1993); West et al., TIPS, 16:67–74 (1995); Dunbrack et al., Folding & Design, 2:27–42 (1997)]. The drug candidates are then selected and tested. The most promising drug candidates are identified and then combined with the protein in a crystalline protein-ligand complex. The three-dimensional structure of the protein-ligand complex is then determined, and new potential antagonists of the protein are identified and/or designed with the aid of computer modeling. This process can then be continued in successive iterations until a lead drug candidate is identified.

Heretofore, the ability to perform structure-based drug design with ADAM33 was severely hampered because there were no X-ray diffraction quality crystals available. The expression and purification of a monodisperse preparation of a polypeptide comprising the modified ADAM33 catalytic domain as disclosed herein, is therefore critical for the initiation of a structure-based drug design program. The present invention also provides crystals of the modified ADAM33 catalytic domain that are conducive for both ligand addition and exchange.

As used herein the following terms shall have the definitions set out below:

As used herein the term "polypeptide" is used interchangeably with the term "protein" and is further meant to encompass peptides. Therefore, as used herein, a polypeptide is a polymer of two or more amino acids joined together by peptide linkages. Preferably, a polypeptide is a polymer comprising twenty or more amino acid residues joined together by peptide linkages, whereas a peptide comprises two to twenty amino acid residues joined together by peptide linkages.

As used herein a polypeptide "consisting essentially of" or that "consists essentially of" a specified amino acid sequence is a polypeptide that (i) retains an important characteristic of the polypeptide comprising that amino acid sequence, e.g., the catalytic activity of the polypeptide, and (ii) further comprises the identical amino acid sequence, except it consists of plus or minus 10% (or a lower percentage), and preferably plus or minus 5% (or a lower percentage) of the amino acid residues. Additional amino acid residues can be part of a linked Tag, such as the C-terminal Ser-Gly $His_6$ Tag (SEQ ID NO: 36) disclosed herein.

As used herein a "modified ADAM33 catalytic domain" is an ADAM33 catalytic domain that has been modified to remove at least one N-glycosylation site, and retains its catalytic activity, at least to an extent that the catalytic activity is equivalent to that retained for an active fragment as defined below. Preferably, at least one of the two amino acid residues of ADAM33 that are N-glycosylation sites, i.e., Asn231 or Asn 276, has been replaced. Any other amino acid can replace these two asparagines, but preferably the substitute amino acid is a glutamine. In a preferred embodiment the modified ADAM33 catalytic domain has the amino acid sequence of SEQ ID NO: 8. Other modified ADAM33 catalytic domains are also exemplified below.

The numbering of ASN231 and ASN276 as used herein, is with respect to the wild type ADAM33 pre, pro and catalytic amino acid sequences, i.e., the ADAM33 pre sequence (SEQ ID NO: 21) combined with the amino acid sequences of the ADAM33 pro and catalytic domains (SEQ ID NO: 30).

As used herein a "polypeptide comprising a modified ADAM33 catalytic domain", can be (i) the full length ADAM33 protein comprising the modified ADAM33 catalytic domain in place of the wild type catalytic domain (ii) a fragment of the ADAM33 protein that includes the modified ADAM33 catalytic domain e.g., the pro and catalytic domain, (iii) the modified ADAM33 catalytic domain alone, or (iv) a chimeric protein which comprises any of the above.

As used herein a "proteolytic ADAM33 polypeptide" of the present invention is a polypeptide that is capable of catalyzing the proteolytic cleavage of a substrate (natural or artificial) of the native ADAM33 protease. A proteolytic ADAM33 polypeptide of the present invention minimally comprises an active fragment of the ADAM33 catalytic domain that retains proteolytic activity. A proteolytic ADAM33 polypeptide of the present invention can be a chimeric protein.

As used herein an "active fragment" of the catalytic domain of ADAM33" is a fragment of the catalytic domain of ADAM33 that retains at least about 10%, preferably at least about 20%, and more preferably at least about 25% of the proteolytic activity of the wild type ADAM33 protease (SEQ ID NO: 4). These activity measurements can be determined with the proteolytic assay provided herein. Preferably, the active fragment retains at least about 25%, more preferably at least about 50%, and even more preferably at least about 75% of the amino acid residues of the catalytic domain of ADAM33 having the amino acid sequence of SEQ ID NO: 4. More preferably, the amino acid sequence of the active fragment of the ADAM33 catalytic domain has at least about 95% identity to the corresponding amino acid residues of SEQ ID NO: 4.

As used herein the term "chimeric" protein is meant to include "fusion proteins". "Chimeric" proteins of the present invention comprise at least a portion of a non-ADAM33 protein or peptide joined via a peptide bond to at least a portion of an ADAM33 catalytic domain. Chimeric proteins can have additional structural, regulatory, and/or catalytic properties. As used herein a chimeric protein can contain multiple additions to at least a portion of an ADAM33 catalytic domain, e.g., it can comprise both a Ser-Gly-His$_6$Tag (SEQ ID NO: 36) and a secretion signaling signal, as exemplified below. In a particular embodiment the chimeric protein functions as a means of detecting and/or isolating the polypeptide or fragment thereof after a recombinant nucleic acid encoding the ADAM33 catalytic domain or fragment thereof is expressed. Non-ADAM33 amino acid sequences are preferably either amino- or carboxy-terminal to the ADAM33 sequence.

As used herein one amino acid sequence is 100% "identical" to a second amino acid sequence when the amino acid residues of both sequences are identical. Accordingly, an amino acid sequence is 50% "identical" to a second amino acid sequence when 50% of the amino acid residues of the two amino acid sequences are identical. The sequence comparison is performed over a contiguous block of amino acid residues comprised by the ADAM33 polypeptide or fragment thereof or the portion of the ADAM33 polypeptide or fragment thereof being compared, e.g., a modified ADAM33 catalytic domain (SEQ ID NO: 6). In a preferred embodiment, selected deletions or insertions that could otherwise alter the correspondence between the two amino acid sequences are taken into account.

As used herein, DNA and protein sequence percent identity can be determined using C, MacVector 6.0.1, Vector NTI (Informax, Inc. MD), Oxford Molecular Group PLC (1996) and the Clustal W algorithm with the alignment default parameters, and default parameters for identity. These commercially available programs can also be used to determine sequence similarity using the same or analogous default parameters. Alternatively, an Advanced Blast search under the default filter conditions can be used, e.g., using the GCG (Genetics Computer Group, Program Manual for the GCG Package, Version 7, Madison, Wis.) pileup program using the default parameters.

As used herein a "zinc metalloprotease" is a proteinase and/or a peptidase that requires zinc for its proteolytic activity.

As used herein, a "cysteine switch" is a cysteine residue from one domain of a zinc metalloprotease that binds to the zinc of the catalytic domain of a zinc metalloprotease, and thereby acts as a natural inhibitor of the catalytic activity of the zinc metalloprotease. Therefore, dislodging the cysteine residue from the zinc of the catalytic domain can serve to activate the proteolytic activity of the catalytic domain.

As used herein a "nucleic acid" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. When referring to a nucleic acid that is double stranded both the "sense" strand and the complementary "antisense" strand are intended to be included. Thus a nucleic acid that is hybridizable to SEQ ID NO: 1, for example, can be either hybridizable to the "sense" strand of SEQ ID NO: 1, which is particularly listed in the SEQUENCE LISTING, or to the "antisense" strand which can be readily determined from that SEQUENCE LISTING.

A DNA "coding sequence" is a double-stranded DNA sequence that is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

Transcriptional and translational control sequences are DNA regulatory sequences, such as promoters, enhancers, terminators, and the like, that provide for the expression of a coding sequence in a host cell. In eukaryotic cells, polyadenylation signals are control sequences.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which can then be trans-RNA spliced and translated into the protein encoded by the coding sequence.

A nucleic acid sequence is "operatively linked" to an expression control sequence when the expression control sequence controls or regulates the transcription and translation of that nucleic acid sequence. The term operatively linked includes having an appropriate start signal.

A "heterologous nucleotide sequence" as used herein is a nucleotide sequence that is added by recombinant methods to a nucleotide sequence encoding a portion of the ADAM33 of the present invention to form a nucleic acid that is not naturally formed in nature. Such nucleic acids can encode chimeric proteins such as one comprising an alternative secretion signaling sequence e.g., the Bip pre sequence having the amino acid sequence of SEQ ID NO: 22, and a SerGly His$_6$Tag (SEQ ID NO: 36), as exemplified below. Thus, as used herein, a heterologous nucleotide sequence need not be a single contiguous nucleotide sequence, but can include multiple non-contiguous nucleotide sequences that have been combined with a nucleotide sequence encoding a portion of the ADAM33 of the present invention. A heterologous nucleotide sequence can comprise non-coding sequences including restriction sites, regulatory sites, promoters and the like. In still another embodiment the heterologous nucleotide can function as a means of detecting a nucleotide sequence of the present invention. The present invention provides heterologous nucleotide sequences that when combined with nucleotide sequences encoding ADAM33 or a fragment thereof, are necessary and sufficient to encode all of the chimeric proteins of the present invention.

The phrase "binding to" in regard to a ligand binding to a polypeptide is used herein to include any or all such specific interactions that lead to a protein-ligand binding complex. This can include processes such as covalent, ionic (electrostatic and/or charged), hydrophobic and hydrogen bonding, but does not include non-specific associations such solvent preferences.

As used herein a "ligand" of a polypeptide (e.g., ADAM33) is a compound that binds to the polypeptide in a protein-ligand binding complex. In a specific embodiment of the present invention the polypeptide has an enzymatic activity and the ligand inhibits that activity when bound to the polypeptide in a protein-ligand binding complex. Such a ligand is also termed an "inhibitor".

As used herein the term "initial ligand" denotes a ligand in a protein-ligand complex that is, or can be displaced by a "substitute ligand".

As used herein, a "protein-ligand binding complex" is a specific association between a polypeptide and the compound that binds to it. In a preferred embodiment of the present invention, the ligand is an inhibitor of the polypeptide. In a particular embodiment of this type, the binding of the inhibitor to the polypeptide occurs at the active site of the polypeptide.

As used herein "incubating a ligand with a crystal" is used interchangeably with "soaking a crystal with a ligand".

Incubating a ligand with a crystal is the contacting of a ligand with a crystal of a polypeptide under the appropriate conditions and for a sufficient time period (e.g., several days) for the ligand to bind to the crystalline polypeptide and form a crystalline protein-ligand complex. Such incubating can further and/or alternatively include contacting an excess of a substitute ligand with a crystal of a protein-ligand complex under the appropriate conditions and for a sufficient time period (e.g., several days) for the substitute ligand to replace the initial ligand and form the new crystalline protein-ligand complex.

As used herein the terms "displacing", "replacing", and "exchanging" are used interchangeably in regard to the substitution of one ligand in a protein-ligand complex for another.

As used herein an "excess of a substitute ligand" is an amount of that ligand that is sufficient to replace 80% or more, and preferably 90% or more, of the initial ligand in a protein-ligand complex. In a particular embodiment of this type, the concentration of the substitute ligand is about ten-fold higher than the concentration of the protein-ligand complex. In a preferred embodiment, the concentration of the substitute ligand is about one hundred-fold higher than the concentration of the protein-ligand complex.

As used herein the term "X-ray diffractable crystal" is a crystal of a compound that yields a discernable diffraction pattern when subjected to 0.5 to 2.5 Å incident X-ray radiation.

As used herein an "X-ray quality crystal" is an X-ray diffractable crystal that can yield meaningful structural data of its crystalline composition when subjected to X-ray crystallographic analysis.

As used herein, and unless otherwise specified, the terms "agent", "potential drug", "compound", or "test compound" are used interchangeably, and refer to chemicals that have or potentially have a use as a modulator of the proteolytic activity of ADAM33. Preferably the modulator is an inhibitor of the proteolytic activity of ADAM33. Preferably such agents include drugs for the treatment or prevention of a disease and/or condition involving the proteolytic action of ADAM33, e.g., asthma. Therefore, such agents may be used, as described herein, in drug assays and drug screens and the like.

As used herein a "small organic molecule" is an organic compound [or organic compound complexed with an inorganic compound (e.g., metal)] that has a molecular weight of less than 3 Kd.

As used herein the terms "approximately" and "about" are used to signify that a value is within twenty percent of the indicated value i.e., an amino acid sequence containing "approximately" 260 amino acid residues can contain between 208 and 312 amino acid residues.

As used herein the phrases "structure-based rational drug design", "structure-based drug design" and "structure assisted drug design" are used interchangeably. These phrases are meant to convey a particular method of identifying and/or designing a ligand (preferably an inhibitor) for a specific target protein that includes the use of the three-dimensional structure of that protein and/or its corresponding protein-ligand complex.

Nucleic Acids Encoding ADAM33

Obtaining and/or constructing a cDNA that encodes a polypeptide comprising a ADAM33 catalytic domain, e.g., comprising the amino acid sequence of SEQ ID NO: 38, facilitates the production of the large quantities of protein required to perform standard enzyme assays and/or X-ray crystallographic analysis. In addition, the nucleic acids can be used in gene therapy, or alternatively to generate the ADAM33 catalytic domain for use in a protein therapy protocol in the treatment of respiratory diseases such as asthma.

The present invention provides specific nucleic acid constructs that allow for the expression and isolation of large quantities of stable and active fragments of ADAM33 comprising the ADAM33 catalytic domain. These nucleic acids can further contain heterologous nucleotide sequences. To express a recombinant protein of the present invention in a host cell, an expression vector can be constructed comprising the corresponding cDNA. The present invention therefore, provides expression vectors containing nucleic acids encoding polypeptides comprising the ADAM33 catalytic domains of the present invention. Due to the degeneracy of nucleotide coding sequences, other DNA sequences which encode substantially the same amino acid sequence as a nucleic acid encoding a polypeptide comprising the ADAM33 catalytic domain or a modified ADAM 33 catalytic domain of the present invention may be used in the practice of the present invention. These include, but are not limited to, allelic genes, homologous genes from other species, which are altered by the substitution of different codons that encode the same amino acid residue within the sequence, thus producing a silent change. Host cells comprising the expression vectors of the present invention are also provided. One particular host cell, the *Drosophila melanogaster* S2 cell line is specifically exemplified below.

General methods for the cloning of cDNAs and expression of their corresponding recombinant proteins have been described [see Sambrook and Russell, *Molecular Cloning, A Laboratory Manual*, 3rd edition, Cold Spring Harbor Laboratory Press, Cold Spring Harbor L.I. (2000)]. The particular methodology used herein is exemplified below.

The nucleotide sequence for open reading frame of an ADAM33 of the present invention with an SG linker, and a polyHis Tag (H6), SEQ ID NO: 36, is shown below (SEQ ID NO: 1). In particular, the pre domain can be the ADAM33 pre domain (SEQ ID NO: 21), or another secretion signal sequence that is derived from a eukaryotic organism or a virus. The BIP sequence, exemplified below, is derived from the *Drosophila* immunoglobulin binding chaperon protein, and is a preferred embodiment. Other possible pre domains can be employed including that from: PIPP (i.e. Pre-intermoult gene-1 protein precursor), HBM (i.e., Honeybee Mellitin), H1C (i.e. Larval/pupal cuticle protein H1C precursor), LPM (i.e, Leucokinins precursor of mosquito Aedes aegypti), Egt (i.e., Baculovirus ecdysteroid UDP glucosyltransferase) and P67 (i.e., Baculovirus envelope glycoprotein P67).

| | | |
|---|---|---|
| ADAM33: | MGWRPRRARGTPLLLLLLLLLLWPVPGAGV | (SEQ ID NO: 21) |
| BIP: | MKLCILLAVVAFVGLSLG | (SEQ ID NO: 22) |
| PIPP: | MKLTKLWLLFVCLGLFVTLVVS | (SEQ ID NO: 23) |
| HBM: | MKFLVNVNLVFMVVYISYIYA | (SEQ ID NO: 24) |
| H1C: | MYKFVVFAAALAYANA | (SEQ ID NO: 25) |
| LPM: | MAMLLQVALPLLAAVSWG | (SEQ ID NO: 26) |
| EGT: | MTILCWLALLSTLTAVNA | (SEQ ID NO: 27) |
| P67: | MVSAIVLYVLLAAAAHSAFAAEHC | (SEQ ID NO: 28) |

In addition, any technique for mutagenesis known in the art can be used to convert the native (wild type) ADAM33 catalytic domain to a modified domain, including but not limited to, in vitro site-directed mutagenesis [Hutchinson et al., *J. Biol. Chem.*, 253:6551 (1978); Zoller and Smith, *DNA*, 3:479–488 (1984); Oliphant et al., *Gene*, 44:177 (1986); Hutchinson et al., *Proc. Natl. Acad. Sci. U.S.A.*, 83:710 (1986)]. The use of TAB@ linkers (Pharmacia), etc. and PCR techniques also can be employed for site directed mutagenesis [see Higuchi, "Using PCR to Engineer DNA", in PCR Technology: Principles and Applications for DNA Amplification, H. Erlich, ed., Stockton Press, Chapter 6, pp. 61–70 (1989)].

Preferably mutagenesis (i.e., modification) of the ADAM33 catalytic domain is performed in a two step process [Wang, and Malcolm, *BioTechniques* 26:680–682 (1999)]. In the Example below, two extension reactions were performed in separate tubes in the first stage: (i) one containing the forward primer, and (ii) the other containing the reverse primer. After two cycles, the two reactions are mixed and the standard QuickChange mutagenesis procedure is carried out for an additional 18 cycles. Following amplification, the parental strand is digested with 1 Unit of Dpn1 for 1 hour and an aliquot is transformed into DH5-alpha cells [GeneWiz, New York, N.Y.]. Preferably all of the constructs are sequence confirmed.

The ADAM33 Polypeptide

The ADAM33 protein fragment that was initially expressed in the *Drosophila* S2 cell line exemplified below, has the amino acid sequence of SEQ ID NO: 2. The amino acid sequences for the catalytic domains of the modified ADAM33 polypeptides include:

EARRTRKYLELYIVADHTLFLTRHRNLXHTKQRLLEVANYVDQLLRTLDIQVALTGL   SEQ ID NO: 6

EVWTERDRSRVTQDANATLWAFLQWRRGLWAQRPHDSAQLLTGRAFQGATVGLAPVE

-continued

```
GMCRAESSGGVSTDHSELPIGAAATMAHEIGHSLGLSHDPDGCCVEAAAESGGCVMA

AATGHPFPRVFSACSRRQLRAFFRKGGGACLSNAP:
```

Where "X" can be any amino acid except asparagine. In a preferred embodiment, X is Q, as exemplified below (SEQ ID NO: 8).

```
EARRTRKYLELYIVADHTLFLTRHRNLNHTKQRLLEVANYVDQLLRTLDIQVALTGL    SEQ ID NO: 10

EVWTERDRSRVTQDAXATLWAFLQWRRGLWAQRPHDSAQLLTGRAFQGATVGLAPVE

GMCRAESSGGVSTDHSELPIGAAATMAHEIGHSLGLSHDPDGCCVEAAAESGGCVMA

AATGHPFPRVFSACSRRQLRAFFRKGGGACLSNAP:
```

Where "X" can be any amino acid except asparagine. In a preferred embodiment, X is Q, as exemplified below (SEQ ID NO: 12).

```
EARRTRKYLELYIVADHTLFLTRHRNLX₁HTKQRLLEVANYVDQLLRTLDIQVALTG    SEQ ID NO: 14

LEVWTERDRSRVTQDAX₂ATLWAFLQWRRGLWAQRPHDSAQLLTGRAFQGATVGLAP

VEGMCRAESSGGVSTDHSELPIGAAATMAHEIGHSLGLSHDPDGCCVEAAAESGGCV

MAAATGHPFPRVFSACSRRQLRAFFRKGGGACLSNAP:
```

Where "$X_1$" and "$X_2$" can be the same or different and either can be any amino acid except asparagine. In a preferred embodiment, "$X_1$" and "$X_2$" are both Q, as exemplified below (SEQ ID NO: 16).

The amino acid sequences listed above are without the C-terminal Ser-Gly-His$_6$Tag (SEQ ID NO: 36) that was contained by the modified ADAM33 fragments identified in the Example below.

In a particular embodiment of the present invention, a modified ADAM33 catalytic domain or active fragment thereof is at least about 75% identical, more preferably at least about 90% identical, and most preferably at least about 95% identical to the modified ADAM33 catalytic domain having an amino acid sequence of SEQ ID NO: 8.

Polypeptides comprising the ADAM33 catalytic domains, including the modified ADAM33 catalytic domains, of the present invention include those containing altered sequences in which functionally equivalent amino acid residues are substituted for residues within the sequence resulting in a conservative amino acid substitution. For example, one or more amino acid residues within the sequence can be substituted by another amino acid of a similar polarity, which acts as a functional equivalent, resulting in a silent alteration. Substitutes for an amino acid within the sequence may be selected from other members of the class to which the amino acid belongs. In certain embodiments, there will be up to ten conservative amino acid substitutions, or up to nine, eight, seven, six or five conservative amino acid substitutions. In other embodiments, there will be up to four, three, two or one conservative amino acid substitution.

For example, the nonpolar amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, serine, threonine, cysteine, tyrosine, asparagine, and glutamine. The positively charged (basic) amino acids include arginine, and lysine. The negatively charged (acidic) amino acids include aspartic acid and glutamic acid.

Particularly preferred conserved amino acid exchanges are:

(a) Lys for Arg or vice versa such that a positive charge may be maintained;

(b) Glu for Asp or vice versa such that a negative charge may be maintained;

(c) Ser for Thr or vice versa such that a free —OH can be maintained;

(d) Gln for Asn or vice versa such that a free $NH_2$ can be maintained; and (e) lle for Leu or for Val or vice versa as roughly equivalent hydrophobic amino acids.

All of the ADAM33 catalytic domains, including the modified ADAM33 catalytic domains, of the present invention also can be part of a chimeric protein. In a specific embodiment, a chimeric ADAM33 protein is expressed in a eukaryotic cell. Such a chimeric protein can be a fusion protein used to isolate a modified ADAM33 of the present invention, through the use of an affinity column that is specific for the protein fused to the ADAM33 protein. In one such embodiment, the chimeric ADAM33 is expressed in a eukaryotic cell. Examples of such fusion proteins include: a glutathione-S-transferase (GST) fusion protein, a maltose-binding protein (MBP) fusion protein, a FLAG-tagged fusion protein, or as specifically exemplified below, a polyhistidine-tagged fusion protein. Specific linker sequences such as the Ser-Gly linker exemplified below can also be part of such a fusion protein.

Expression of a chimeric ADAM33 protein, or fragment thereof, as a fusion protein can facilitate stable expression, and/or allow for purification based on the properties of the fusion partner. Thus the purification of the recombinant polypeptides of the present invention can be simplified through the use of fusion proteins having affinity Tags. For example, GST binds glutathione conjugated to a solid support matrix, MBP binds to a maltose matrix, and polyhistidine chelates to a Ni-chelation support matrix, as specifically exemplified below [see Hochuli et al., *Biotechnology* 6:1321–1325 (1998)]. The fusion protein can be eluted from the specific matrix with appropriate buffers, or by treating with a protease that is specific for a cleavage site that has been genetically engineered in between the ADAM33 protein and its fusion partner. Alternatively, an ADAM33 catalytic domain can be combined with a marker protein such as green fluorescent protein [Waldo et al., *Nature Biotech.* 17:691–695 (1999); U.S. Pat. No. 5,625,048 and WO 97/26333].

Alternatively or in addition, other column chromatography steps (e.g., gel filtration, ion exchange, affinity chromatography etc.) can be used to purify the recombinant proteins of the present invention. In many cases, such column chromatography steps employ high performance liquid chromatography or analogous methods in place of the more classical gravity-based procedures.

The specific details for the preferred purification procedure of the recombinant and modified ADAM33 catalytic domains of the present invention are provided in the Example below.

In addition, the present invention provides a method of expressing recombinant catalytic domains of zinc metalloproteins in eukaryotic host cells. Preferably, the zinc metalloproteins are metalloproteases in the ADAM family. In this aspect of the invention, $Cd^{2+}$ and/or $Zn^{2+}$ are employed to induce expression and/or to maximize the amount of the catalytic domain of the protein obtained. Preferably, a recombinant DNA construct is employed comprising a metallothionein promoter that is operatively linked to the nucleotide sequence that encodes the catalytic domain. In a particular embodiment of this type, the expression of the recombinant metalloprotein is induced by 1–25 µM $Cd^{2+}$. In a preferred embodiment 10µM–1 mM $Zn^{2+}$ is included to optimize the amount of the catalytic domain obtained (see the Example below).

Preferably, the eukaryotic host cell is a *Drosophila* cell, and more preferably the *Drosophila* cell is from a *Drosophila melanogaster* Schneider 2 (S2) stable cell line. In a particular embodiment of this type, induction and optimization is achieved with 10 µM $Cd^{2+}$ and 200 µM $Zn^{2+}$.

In still another embodiment, polypeptides comprising the ADAM33 catalytic domains, including the modified ADAM33 catalytic domains, of the present invention are chemically synthesized [see e.g., Synthetic Peptides: *A User's Guide*, W.H. Freeman & Co., New York, N.Y., pp. 382, Grant, ed. (1992)].

Enzyme Assays

The catalytic activity of the ADAM33 protease or active fragment thereof can be determined in any of a number relatively standard protease assay formats. One particularly useful substrate has been derived from the amyloid percursor protein and contains the amino acid sequence of YEVHH-QKLVF (SEQ ID NO: 35). The cleavage site is indicated by the hyphen, i.e., the scissile bond being between the second histidine and the adjacent glutamine. Other useful substrates of ADAM33 protease activity are provided in U.S. Provisional Application 60/440,263. One particular set of assay conditions contains 25 nM of the ADAM33 catalytic domain and 25 µM substrate. The reaction is initiated in 25 mM Hepes, pH 8.0, 2M NaCl by mixing the enzyme with the substrate. The rate of reaction is measured over a defined time period (e.g., for 1 hour at room temperature) and then stopped. Product formation can be quantified at 214 nm by HPLC using a reverse phase column to separate the substrate from the products. The ability of any given compound added to the reaction to act as an inhibitor of ADAM33 can be readily determined by this assay by comparing the rate of cleavage in the absence and presence of the compound.

Alternatively, ADAM33 activity can be determined by following the extent of the cleavage of a synthetic substrate by ADAM33 using surface plasmon resonance (SPR) spectroscopy [U.S. Pat. No. 5,981,167]. In a particular embodiment the substrate is Biotin-YEVHH-QKLVF-Phosphotyrosine (SEQ ID NO: 41) or another substrate described in U.S. Provisional Application 60/440,263. The substrate and ADAM33, or active fragment thereof, are placed in a reaction mixture under conditions that allow the protease to cleave the substrate. The reaction is stopped at a set time and then brought into contact with an anti-phosphotyrosine antibody bound to a sensor chip under conditions that allow the antibody to bind the substrate.

The amount of cleavage is determined by comparing the mass of the intact substrate with the mass of the cleaved substrate as detected by surface plasmon resonance technology.

The SPR-based ADAM33 assay described above also can be used to determine if compound is an inhibitor of ADAM33. In one such assay a compound is placed in the reaction mixture with the ADAM33 or active fragment thereof and the Biotin-YEVHH-QKLVF-Phosphotyrosine substrate or other substrate described U.S. Provisional Application 60/440,263. The reaction is stopped at a set time and then brought into contact with an anti-phosphotyrosine antibody bound to a sensor chip under conditions that allow the antibody to bind the substrate. The amount of cleavage is determined by comparing the mass of the intact substrate with the mass of the cleaved substrate as detected by surface plasmon resonance technology. The compound is identified as an inhibitor of ADAM33 when the amount of cleavage determined is less when the reaction mixture contains the compound than when it did not.

Other assays to measure the catalytic activity of the ADAM33 protease or active fragment thereof, as well as assays for identify substrates and/or inhibitors of ADAM33 are disclosed in U.S. Provisional Application 60/440,263.

Administration

A pharmaceutical composition containing a polypeptide comprising an ADAM33 catalytic domain and a pharmaceutically acceptable carrier can used to treat a respiratory condition, such as asthma. Such pharmaceutical compositions may be administered parenterally, e.g., via intravenous injection, transmucosally, e.g., orally, nasally, rectally, or transdermally, or by pulmonary injection. The administration may also be intra-arteriole, intramuscular, intradermal, subcutaneous, intraperitoneal, intraventricular, and intracranial. A polypeptide comprising an ADAM33 catalytic domain also can be modified to cross cellular or nuclear membranes, which would allow for intravenous or oral administration. Strategies are available for such crossing, including but not limited to, increasing the hydrophobic nature of a protein, introducing the protein as a conjugate to a carrier, such as a ligand for a specific receptor, or targeted to a receptor.

Therefore, the present invention also provides for conjugating targeting molecules to a polypeptide comprising an ADAM33 catalytic domain. A targeting molecule is intended to include a molecule which, when administered in vivo, localizes to one or more desired locations. In various embodiments, the targeting molecule can be a peptide or protein, antibody, lectin, carbohydrate, or steroid. In a related embodiment, the therapeutic compound can be delivered in a vesicle such as a liposome [see Langer, *Science,* 249:1527–1533 (1990); Treat et al., in Liposomes in the Therapy of Infectious Disease and Cancer, Lopez-Berestein and Fidler (eds.), Liss: New York, pp. 353–365 (1989); Lopez-Berestein, ibid., pp. 317–327; see generally ibid.].

In yet another embodiment, the therapeutic compound can be delivered in a controlled release system. For example, the polypeptide may be administered using intravenous infusion, an implantable osmotic pump or other modes of administration [see Langer, *Science,* 249:1527–1533 (1990); Sefton, *CRC Crit. Ref. Biomed. Eng.,* 14:201 (1987); Buchwald et al., *Surgery,* 88:507 (1980); Saudek et al., *N. Engl. J. Med.,* 321:574 (1989)]. Various and numerous methods are known in the art for transdermal administration of a pharmaceutical composition of the present invention, e.g., via a transdermal patch [see U.S. Pat. No. 5,407,713; 5,352,456; 5,008,110]. Nasal delivery of the polypeptides comprising an ADAM33 catalytic domain of the present invention are also contemplated. Nasal delivery allows the passage of the protein to the blood stream directly after administering the therapeutic product to the nose, without the necessity for deposition of the product in the lung. Formulations for nasal delivery include those with dextran or cyclodextran.

Oral solid dosage forms of a polypeptide comprising an ADAM33 catalytic domain are also provided by the present invention. Oral solid dosage forms are described generally in Chapter 45 of Remington's Pharmaceutical Sciences, [20th Ed. (2000), Lippincott, Williams and Wilkins, Baltimore Md. 21201, which is herein incorporated by reference].

A pharmaceutical composition generally includes a pharmaceutically acceptable carrier. Examples of such carriers are normal saline solution, Ringer's solution, dextrose solution, and Hnak's solution. One particular carrier is a macromolecule that is soluble in the circulatory system and that is physiologically acceptable where physiological acceptance means that those of skill in the art would accept injection of said carrier into a patient as part of a therapeutic regime. The carrier preferably is relatively stable in the circulatory system with an acceptable plasma half-life for clearance. Such macromolecules include but are not limited to soya lecithin, oleic acid and sorbitan trioleate, with sorbitan trioleate preferred.

The present invention further provides pharmaceutical compositions that also comprise pharmaceutically acceptable diluents, preservatives, solubilizers, emulsifiers, adjuvants and/or carriers. Such compositions include diluents of various buffer content (e.g.,Tris-HCl, acetate, phosphate), pH and ionic strength, additives such as detergents and solubilizing agents (e.g., Tween 80, Polysorbate 80), anti-oxidants (e.g., ascorbic acid, sodium metabisulfite), preservatives (e.g., thimersol, benzyl alcohol) and bulking substances (e.g., lactose, mannitol), [see, e.g., Remington's Pharmaceutical Sciences, 20th Ed. (2000) Lippincott, Williams and Wilkins, Baltimore Md. 21201, which is hereby incorporated by reference in its entirety]. The compositions may be prepared in any of a number of manners including in liquid form, or in a dried powder, such as a lyophilized powder.

A therapeutic polypeptide comprising an ADAM33 catalytic domain may be chemically modified. The chemical modification can be an attachment of at least one moiety to the polypeptide itself. In one such embodiment the moiety inhibits proteolysis. In another embodiment the moiety facilitates the uptake of the polypeptide into the blood stream from the stomach or intestine. In still another embodiment, the moiety enhances the overall stability of the polypeptide and/or increases its circulation time in the body. One example of such a moiety is polyethylene glycol [see e.g., WO95/13090, U.S. Pat. Nos. 5,711,944, 5,951,974, 5,981,709].

A subject for whom administration of a therapeutic polypeptide comprising an ADAM33 catalytic domain is an effective therapeutic regimen is preferably a human (adult or child), but can be any animal. Thus, as can be readily appreciated by one of ordinary skill in the art, the methods and pharmaceutical compositions of the present invention are particularly suited to administration to any animal for veterinary medical use, particularly a mammal, and including, but by no means limited to domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, and cats.

Gene Therapy

A nucleic acid of the present invention encoding the ADAM33 catalytic domain can be introduced either in vivo, ex vivo, or in vitro into a suitable subject. Preferably, the nucleic acid is contained by a viral vector. Such vectors include an attenuated or defective DNA virus, such as but not limited to herpes simplex virus (HSV), papillomavirus, Epstein Barr virus (EBV), adenovirus, adeno-associated virus (AAV), and the like. A particular viral vector is the adenoviral vector as disclosed in U.S. Pat. No. 6,210,939.

Defective viruses, which entirely or almost entirely lack viral genes, are useful vectors. A defective virus is not infective after its introduction into a cell. Use of defective viral vectors allows for administration in a specific, localized area of a group of cells, without concern that the vector can infect other cells. Examples of particular defective viral vectors include a defective herpes virus I (HSV1) vector [Kaplitt et al., *Molec. Cell. Neurosci.,* 2:320–330 (1991)], and a defective adeno-associated virus vector [see e.g., U.S. Pat. No. 6,040,172].

In another embodiment the gene can be introduced in a retroviral vector, [see e.g., U.S. Pat. No. 5,399,346, WO 95/07358]. Targeted gene delivery has also been described [WO 95/28494]. Alternatively, a vector can be introduced by lipofection [Feigner, et. al., *Proc. Natl. Acad. Sci. U.S.A.,* 84:7413–7417 (1987); see also Mackey et al., *Proc. Natl. Acad. Sci. U.S.A.,* 85:8027–8031 (1988)]. The use of cationic lipids may promote encapsulation of negatively charged nucleic acids, and also promote fusion with negatively charged cell membranes [Felgner and Ringold, *Science,* 337:387–388 (1989)]. The use of lipofection to introduce exogenous nucleic acids into the specific organs in vivo has certain practical advantages. Molecular targeting of liposomes to specific cells represents one area of benefit.

It is also possible to introduce a vector as a naked DNA plasmid. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun, or use of a DNA vector transporter [see, e.g., Wu et al., *J. Biol. Chem.,* 267:963–967

(1992); Wu and Wu, *J. Biol. Chem.*, 263:14621–14624 (1988); U.S. Pat. No. 5,916,879.

Crystallization

Crystals of a polypeptide comprising a modified ADAM33 catalytic domain of the present invention, or a corresponding protein-ligand complex with, e.g., N4-[2,2-dimethyl-1(S)-[(methylamino)carbonyl]propyl]-N1,2(S)-dihydroxy-3(R)-(2-methylpropyl) butanediamide, can be grown by a number of techniques including batch crystallization, vapor diffusion (e.g., by sitting drop or hanging drop) and by microdialysis. In Example 1 below, the modified ADAM33 catalytic domain was crystallized by hanging drop vapor diffusion. Seeding of the crystals in some instances is required to obtain X-ray quality crystals. Standard micro and/or macro seeding of crystals may therefore be used.

A ligand also can be soaked into a crystal of a polypeptide comprising a modified ADAM33 catalytic domain of the present invention to form a protein-initial ligand complex. In addition, a substitute ligand can replace an initial ligand by soaking a crystal of a protein-initial ligand complex with the substitute ligand. In this case, one or more crystals of the protein-initial ligand complex can be placed in the reservoir solution containing about a 10-fold or greater excess of substitute ligand. The crystal is kept under the appropriate conditions and for a sufficient time period for the substitute ligand to replace the initial ligand and form the new crystalline protein-substitute ligand complex (e.g., 1–5 days). After the incubation, the crystal of the protein-substitute ligand complex can be frozen in liquid propane, for example and then used for X-ray diffraction. As taught herein, soaking ligands or substitute ligands into crystals of polypeptides comprising a modified ADAM33 catalytic domain or corresponding protein-initial ligand complexes, is preferably performed under non-alkaline conditions.

Crystals can be characterized using X-rays produced in a conventional source (such as a sealed tube or a rotating anode) or using a synchrotron source. Methods of characterization include, but are not limited to, precision photography, oscillation photography and diffractometer data collection.

As exemplified below, the crystals were flash-cooled in a nitrogen stream at 95 degrees Kelvin. X-ray diffraction data was collected using a Rigaku generator equipped with a Raxis 4++ detector. The data were integrated and scaled using the HKL package. The crystal structure was solved with molecular replacement using the search model atrolysin C (PDB entry 1ATL) [Collaborative Computational Project No.4 *Acta Cryst.* D50 760–763 (1994)].

The Refinement of the structure can be performed using the program CNX which is a commercial version of CNS [Adams et al., *Proc. Natl. Acad. Sci. USA*, 94:5018–5023 (1997)]. Map interpretation and model building also can be performed using O [Jones et al., *Acta Cryst, A* 47:110–119 (1991)]. Other computer programs that can be used to solve crystal structures include: QUANTA, CHARMM; INSIGHT; SYBYL; MACROMODE; and ICM.

Generally, structure-based drug design is performed by analyzing the three-dimensional structures of successive protein-ligand complexes. This iterative process requires X-ray quality crystals of numerous protein-ligand complexes. These crystals can be obtained three ways. First, crystals of each protein-ligand complex can be grown de novo. This is the most time-consuming method, and in many instances requires determining a new set of crystallization conditions. The second method is to incubate (e.g., soak) individual crystals of the uncomplexed protein with each different ligand. This method is much faster than growing new crystals, but still requires a relatively large stock of protein to generate all of the new crystals. The third and most expedient method is to incubate a previously formed protein-ligand crystal with a large excess of a substitute ligand, thereby replacing the initial ligand with the substitute ligand in the protein-ligand complex. The present invention allows all three methods to performed by providing a modified ADAM33 catalytic domain that forms X-ray quality crystals that are also amenable to ligand addition and exchange.

Structure-Based Drug Design

Once three-dimensional structures of crystals comprising modified ADAM33 catalytic domains are determined, a potential inhibitor of ADAM33 can be examined through the use of computer modeling using a docking program such as GRAM, DOCK, or AUTODOCK [Dunbrack et al., *Folding & Design*, 2:2742 (1997)]. This procedure can include computer fitting of potential inhibitors to the modified ADAM33 catalytic domain to ascertain how well the shape and the chemical structure of the potential modulator will interact with the ADAM33 protein [Bugg et al., *Scientific American*, Dec.:92–98 (1993); West et al., *TIBS*, 16:67–74 (1995)]. Computer programs can also be employed to estimate the attraction, repulsion, and steric hindrance of the modified ADAM33 catalytic domain with an inhibitor. In addition, comparison with the structures of other ADAM family proteases allows the selection of inhibitors that are specific for ADAM33.

Generally the tighter the fit, the lower the steric hindrances, and the greater the attractive forces, the more potent the inhibitor, since these properties are consistent with a tighter binding constant. Furthermore, the more specificity in the design of a potential drug the more likely that the drug will not interact as well with other proteins. This will minimize potential side-effects due to unwanted interactions with other proteins.

Initially compounds known to bind ADAM33, or a compound that inhibits the closely related TACE protease [e.g., Letavic et al., *Biorgan. & Medic. Chem Lett.* 12:1387–1390 (2002), Duan et al., *J. Med. Chem.* 45:4954–4957 (2002)], or alternatively, a compound that binds metalloproteases as disclosed as by Zask et al. [*Curr. Pharm. Des.*, 2:624–661 (1996)], can be systematically modified by computer modeling programs until one or more promising potential analogs are identified. Such analysis has been shown to be effective in the development of HIV protease inhibitors [Lam et al., *Science* 263:380–384 (1994); Wlodawer et al., *Ann. Rev. Biochem.* 62:543–585 (1993); Appelt, *Perspectives in Drug Discovery and Design* 1:2348 (1993); Erickson, *Perspectives in Drug Discovery and Design* 1:109–128 (1993)]. Alternatively, a potential inhibitor initially can be obtained by screening a random peptide library or a chemical library. In the former case, a random peptide library can be produced by recombinant bacteriophage, for example, [Scott and Smith, *Science*, 249:386–390 (1990); Cwirla et al., *Proc. Natl. Acad. Sci.*, 87:6378–6382 (1990); Devlin et al., *Science*, 249:404–406 (1990)]. A peptide selected in this manner would then be systematically modified by computer modeling programs, as described above.

If a potential inhibitor is a small organic compound, it either can be selected from a library of chemicals, as are commercially available from most large chemical companies, including Merck, GlaxoSmithKline, Bristol Meyers Squib, Monsanto/Searle, Eli Lilly, Novartis, Aventis and Pfizer. Alternatively, the small organic compound may be synthesized de novo. The de novo synthesis of one or even a relatively small group of specific compounds is reasonable in the art of drug design. Once obtained, the potential inhibitor can be further tested into a standard binding and/or catalytic assay with ADAM33, the ADAM33 catalytic domain, or an active fragment thereof.

For example, a binding assay can be performed following the attachment of the ADAM33 catalytic domain to a solid support. Methods for placing the ADAM33 catalytic domain on the solid support are well known in the art and include such things as linking biotin to the ADAM33 catalytic domain and linking avidin to the solid support. The solid support can be washed to remove unbound protein. A solution of a labeled potential inhibitor can be contacted with the solid support. The solid support is washed again to remove the potential inhibitor not bound to the support. The amount of labeled potential inhibitor remaining with the solid support, and thereby bound to the ADAM33 catalytic domain can be determined. Alternatively, or in addition, the dissociation constant between the labeled potential inhibitor and the ADAM33 catalytic domain, for example, can be determined. Suitable labels for either the ADAM33 catalytic domain or the potential inhibitor include, radioactive labels (e.g., $^{14}C$, $^{1}H$,) and fluorescent labels such as fluorescein isothiocyanate (FITC).

In another embodiment, a Biacore machine can be used to determine the binding constant of the ADAM33 catalytic domain with a potential inhibitor [O'Shannessy et al. *Anal. Biochem.* 212:457–468 (1993); Schuster et al., *Nature* 365: 343–347 (1993)]. In addition, an inhibitor can be identified by following the extent of cleavage of a synthetic substrate by ADAM33 in the presence and absence of the potential inhibitor using surface plasmon resonance (SPR) spectroscopy [U.S. Pat. No. 5,981,167] and as detailed above. In this case a potential inhibitor is identified as an inhibitor of ADAM33 when the amount of substrate cleavage is decreased in the presence of the potential inhibitor relative to in its absence.

When a promising inhibitor is identified, a crystal comprising a protein-ligand complex of the inhibitor and the modified ADAM33 catalytic domain can be prepared. The three-dimensional structure of the resulting crystalline protein-ligand complex can then be determined by molecular replacement analysis, for example.

Molecular replacement involves using a known three-dimensional structure as a search model to determine the structure of a closely related molecule or protein-ligand complex in a different crystalline form. The measured X-ray diffraction properties of the new crystal are compared with the search model structure to compute the position and orientation of the protein in the new crystal. Computer programs that can be used include: X-PLOR [Brunger et al., *Acta Crystallogr. A* 46:585–593 (1990); Brunger et al., *Acta Crystallogr. D Biol. Crystallogr.*, 54:905–921 (1998)], CNS, (Crystallography and NMR System, a next level of XPLOR), and AMORE [Navaza, *Acta Crystallographics* ASO, 157–163 (1994)]. Once the position and orientation are known, an electron density map can be calculated using the search model to provide X-ray phases. Thereafter, the electron density is inspected for structural differences and the search model is modified to conform to the new structure. Using this approach, it is possible to solve the three-dimensional structures of crystals of any protein-ligand complex of the modified ADAM33 catalytic domain.

For all of the drug screening assays described herein, further refinements to the structure of the drug will generally be necessary and can be made by the successive iterations of any and/or all of the steps provided by the particular drug screening assay and/or in combination with other such drug screening assays.

A candidate drug selected by performing structure-based drug design can then be assayed in situ and/or in vivo. A candidate drug can be identified as a drug, for example, if it ameliorates a respiratory symptom linked to the action of ADAM33 in an animal model. Indeed, methods of testing such potential candidate drugs in animal models are well known in the art. The potential drugs can be administered by a variety of ways including topically, orally, subcutaneously, or intraperitoneally depending on the proposed use. Generally, at least two groups of animals are used in the assay, with at least one group being a control group that is administered the administration vehicle without the potential drug.

TABLE 1

TABLE OF SEQUENCES

| SEQ ID NO: | Type | Description |
|---|---|---|
| 1 | N.A. | *Pre, Pro, Catalytic WT domain and SGHis$_6$ Tag |
| 2 | A.A. | Pre, Pro, and Catalytic WT domain |
| 3 | N.A. | WT Catalytic domain |
| 4 | A.A. | WT Catalytic domain |
| 5 | N.A. | Catalytic domain N231X |
| 6 | A.A. | Catalytic domain N231X |
| 7 | N.A. | Catalytic domain N231Q |
| 8 | A.A. | Catalytic domain N231Q |
| 9 | N.A. | Catalytic domain N276X |
| 10 | A.A. | Catalytic domain N276X |
| 11 | N.A. | Catalytic domain N276Q |
| 12 | A.A. | Catalytic domain N276Q |
| 13 | N.A. | Catalytic domain N231X, N276X |
| 14 | A.A. | Catalytic domain N231X, N276X |
| 15 | N.A. | Catalytic domain N231Q, N276Q |
| 16 | A.A. | Catalytic domain N231Q, N276Q |
| 17 | N.A. | N231QF primer |
| 18 | N.A. | N231QR primer |
| 19 | N.A. | N276QF primer |

TABLE 1-continued

TABLE OF SEQUENCES

| SEQ ID NO: | Type | Description |
|---|---|---|
| 20 | N.A. | N276QR primer |
| 21 | A.A. | ADAM33 Pre |
| 22 | A.A. | Bip Pre |
| 23 | A.A. | PIPP Pre |
| 24 | A.A. | Mel Pre |
| 25 | A.A. | H1C Pre |
| 26 | A.A. | LPM Pre |
| 27 | A.A. | Egt Pre |
| 28 | A.A. | P67 Pre |
| 29 | N.A. | Pro, and Catalytic WT domain |
| 30 | A.A. | Pro, and Catalytic WT domain |
| 31 | N.A. | Pro, and N231X, N276X Catalytic domain |
| 32 | A.A. | Pro, and N231X, N276X Catalytic domain |
| 33 | N.A. | Pro, and N231X, Catalytic domain |
| 34 | A.A. | Pro, and N231X, Catalytic domain |
| 35 | A.A. | YEVHH-QKLVF |
| 36 | A.A. | SGHis$_6$ Tag |
| 37 | N.A. | Catalytic domain N231Q and SGHis$_6$ Tag |
| 38 | A.A. | Catalytic domain N231Q and SGHis$_6$ Tag |
| 39 | N.A. | WT primer |
| 40 | N.A. | WT primer |
| 41 | A.A. | YEVHH-QKLVFpY |
| 42 | A.A. | KL-1 Peptide |
| 43 | A.A. | APP Peptide |
| 44 | A.A. | TRANCE Peptide |
| 45 | A.A. | Insulin B Peptide |
| 46 | A.A. | TNF-alpha substrate |
| 47 | A.A. | Fluorogenic substrate |
| 48 | A.A. | MCF Peptide |
| 49 | A.A. | Pro/cat C131A |
| 50 | A.A. | Pro/cat C179A |
| 51 | A.A. | Pro/cat C131A, C179A |
| 52 | A.A. | Pro/cat K176I, C179A |
| 53 | A.A. | Pro/cat C179A, D183N |
| 54 | A.A. | Single chain zymogen R203T/R207S |

*Pre sequence encodes the Drosophila BIP sequence.

The present invention may be better understood by reference to the following non-limiting Example, which is provided as exemplary of the invention. The following example is presented in order to more fully illustrate the preferred embodiments of the invention. It should in no way be construed, however, as limiting the broad scope of the invention.

EXAMPLES

Example 1

Crystallization of ADAM33 For X-ray Diffraction Studies

Summary

A *Drosophila* S2 expression system was established to facilitate the purification of the catalytic domain of ADAM33. Moreover, unique induction conditions and stabilizing reagents for ADAM33 are provided that have significantly improved the purity, activity and stability of the protein.

In addition, the three dimensional structure of the catalytic domain of ADAM33 is provided. This structural information was obtained from a crystal form of the catalytic domain of ADAM33 having a resolution of at least 1.8 Å. This crystalline form is also amenable to inhibitor soaking experiments, thereby eliminating the laborious need to re-crystallize each individual ADAM33-inhibitor co-crystal to be evaluated.

Material and Methods

Cloning of wild type (WT) and modified human ADAM33: The cDNA sequence encoding the ADAM33 pro and catalytic domains and a Ser-Gly-His$_6$ Tag was amplified by PCR using a full length ADAM33 cDNA sequence with the following pair of PCR primers having SEQ ID NOs: 39 and 40.

```
5' ATCTGATATC TCGAGTCAAT GATGGTGATG ATGATGTCCT GACGGGGCAT TGGAGAGGCA AGCGC 3'   (SEQ ID NO: 39)

5' TTAGATTCAT AGGGTACCGC TTCAAGGACA TATCCCTGGG CAG 3'                           (SEQ ID NO: 40)
```

The PCR amplified cDNA was then digested with Kpn and Xho restriction enzymes and ligated into the *Drosophila* expression vector, pMT/Bip/V5-His-C (Invitrogen). The ligation mixture was then transfected into competent bacteria. The positive clones were identified by PCR screening and sequence confirmation The DNA open reading frame of ADAM33 inserted in the cell line for expression was (SEQ ID NO: 1):

Modified ADAM33 catalytic domains (N231Q, N276Q and N231Q/N276Q) were generated using the QucikChange kit (Stratagene, La Jolla, Calif., USA) using the PMT/Bip/216PC 6×His vector as a template and the following complementary mutagenic primers:

```
ATGAAGTTATGCATATTACTGGCCGTCGTGGCCTTTGTTGGCCTCTCGCTCGGGAGATCTCCATGGCCCGGG
GTACCGCTTCAAGGACATATCCCTGGGCAGCCAGTCACCCCGCACTGGGTCCTGGATGGACAACCCTGGCGC
ACCGTCAGCCTGGAGGAGCCGGTCTCGAAGCCAGACATGGGGCTGGTGGCCCTGGAGGCTGAAGGCCAGGAG
CTCCTGCTTGAGCTGGAGAAGAACCACAGGCTGCTGGCCCCAGGATACATAGAAACCCACTACGGCCCAGAT
GGGCAGCCAGTGGTGCTGGCCCCCAACCACACGGATCATTGCCACTACCAAGGGCGAGTAAGGGGTTTCCCC
GACTCCTGGGTAGTCCTCTGCACCTGCTCTGGGATGAGTGGCCTGATCACCCTCAGCAGGAATGCCAGCTAT
TATCTGCGTCCCTGGCCACCCCGGGGCTCCAAGGACTTCTCAACCCACGAGATCTTTCGGATGGAGCAGCTG
CTCACCTGGAAAGGAACCTGTGGCCACAGGGATCCTGGGAACAAAGCGGGCATGACCAGTCTTCCTGGTGGT
CCCCAGAGCAGGGGCAGGCGAGAAGCGCGCAGGACCCGGAAGTACCTGGAACTGTACATTGTGGCAGACCAC
ACCCCTGTTCTTGACTCGGCACCGAAACTTGAACCACACCAAACAGCGTCTCCTGGAAGTCGCCAACTACGTG
GACCAGCTTCTCAGGACTCTGGACATTCAGGTGGCGCTGACCGGCCTGGAGGTGTGGACCGAGCGGGACCGC
AGCCGCGTCACGCAGGACGCCAACGCCACGCTCTGGGCCTTCCTGCAGTGGCGCCGGGGGCTGTGGGCGCAG
CGGCCCCACGACTCCGCGCAGCTGCTCACGGGCCGCGCCTTCCAGGGCGCCACAGTGGGCCTGGCGCCCGTC
GAGGGCATGTGCCGCGCCGAGAGCTCGGGAGGCGTGAGCACGGACCACTCGGAGCTCCCCATCGGCGCCGCA
GCCACCATGGCCATGAGATCGGCCACAGCCTCGGCCTCAGCCACGACCCCGACGGCTGCTGCGTGGAGGCT
GCGGCCGAGTCCGGAGGCTGCGTCATGGCTGCGGCCACCGGGCACCCGTTTCCGCGCGTGTTCAGCGCCTGC
AGCCGCCGCCAGCTGCGCGCCTTCTTCCGCAAGGGGGGCGGCGCTTGCCTCTCCATGCCCCGTCAGGACAT
CATCATCACCATCAT
```

45

The above nucleic acid sequence encodes (1) the "pre" sequence (dashed line); (2) the linker sequence (wavy line);

```
1) N231QF:
5' CTCGGCACCGAAACTTGCAGCACACCAAACAGCGTCTC 3'   (SEQ ID NO: 17)

2) N231QR:
5' GAGACGCTGTTTGGTGTGCTGCAAGTTTCGGTGCCGAG 3'   (SEQ ID NO: 18)

3) N276QF:
5' GTCACGCAGGACGCCCAGGCCACGCTCTGGGCC 3'         (SEQ ID NO: 19)

4) N276QR:
5' GGCCCAGAGCGTGGCCTGGGCGTCCTGCGTGAC 3'         (SEQ ID NO: 20)
```

60

(3) the "pro" domain (the single underline); (4) the wild type catalytic domain (unmarked) that contains the two glycosylation sites ASN231 and ASN276 respectively (in bold); and (5) the SER-GLY-HIS$_6$ Tag (double underlined). Alternative "pre", "linker" and "Tag" sequences can be readily substituted for the ones exemplified in SEQ ID NO: 1 above.

The mutagenesis was performed in two steps as previously described [Wang, and Malcolm, BioTechniques 26: 680–682 (1999)]. In the first stage two extension reactions were performed in separate tubes; one containing the forward primer and the other containing the reverse primer. After two cycles, the two reactions were mixed and the standard QuickChange mutagenesis procedure was carried out for an additional 18 cycles. Following amplification, the parental strand was digested with 1U of Dpn1 for 1 hour and an aliquot was transformed into DH5-alpha cells. All constructs were sequence confirmed [GeneWiz, New York, N.Y.].

The amino acid sequence of the ADAM33 protein fragment expressed in the *Drosophila* S2 cell line was (SEQ ID NO: 2):

PRE) MKLCILLAVVAFVGLSLG (LINKER) RSPWPGVP (PRO) LQGHIPGQPVTPHW
VLDGQPWRTVSLEEPVSKPDMGLVALEAEGOELLLELEKNHRLLAPGYIETHYGPDG
QPVVLAPNHTDHCHYQGRVRGFPDSWVVLCTCSGMSGLITLSRNASYYLRPWPPRGS
KDFSTHEIFRMEQLLTWKGTCGHRDPGNKAGMTSLPGGPQSRGRR (CAT) EARRTRK
YLELYIVADHTLFLTRHRNLNHTKQRLLEVANYVDQLLRTLDIQVALTGLEVWTERD
RSRVTQDANATLWAFLQWRRGLWAQRPHDSAQLLTGRAFQGATVGLAPVEGMCREAS
SGGVSTDHSELPIGAAATMAHEIGHSLGLSHDPDGCCVEAAAESGGCVMAAATGHPF
PRVFSACSRRQLRAFFRKGGGACLSNAPSGHHHHHH

The amino acid sequence of (1) the "pre" sequence (dashed line); (2) the linker sequence (wavy line); (3) the "pro" domain (the single underline); (4) the wild type catalytic domain (unmarked) that contains the two glycosylation sites ASN231 and ASN276 respectively (in bold); and (5) the SER-GLY-HIS$_6$ Tag (double underlined). The two glycosylation sites Asn231 and Asn276 respectively (in bold) that are replaced with glutamine in the modified ADAM33 catalytic domains exemplified below, are in bold.

The amino acid sequence of the wild type ADAM33 catalytic domain is:

clarification by centrifugation. 1 M HEPES pH 7.3 (Fischer # BP299-1) was added to the supernatant so that the final concentration of HEPES was 25 mM. An equal volume of buffer A (25 mM HEPES, pH 7.0, 10% glycerol) was added to reduce the conductivity, and the sample was applied to a an SP-SEPHAROSE FF cation exchange column (Amersham Pharmacia, Piscataway, N.J.).

The SP-SEPHAROSE FF column was washed with 10 column volumes (CV) of buffer A with 100 mM NaCl, and fractions of 1 CV were collected during elution with a salt gradient from 100–500 mM NaCl (Buffer B:25 mM HEPES, pH7.9, 10% glycerol, 500 mM NaCl). The fractions containing the ADAM33 catalytic domain were pooled, 5 mM imidazole was added, and the sample was applied to a Ni-NTA column equilibrated in buffer C (25 mM HEPES, pH7.9, 10% glycerol, 500 mM NaCl, 5 mM Imidazole).

The Ni-NTA column was washed with 15–20 CV of buffer C until a stable baseline was achieved, and the protein EARRTRKYLELYIVADHTLFLTRHRNLNHTKQRLLEVANYVDQLLRTLDIQVALTGL (SEQ ID NO: 4)
EVWTERDRSRVTQDANATLWAFLQWRRGLWAQRPHDSAQLLTGRAFQGATVGLAPVE
GMCRAESSGGVSTDHSELPIGAAATMAHEIGHSLGLSHDPDGCCVEAAAESGGCVMA
AATGHPFPRVFSACSRRQLRAFFRKGGGACLSNAP Establishment of *Drosophila melanogaster* Schneider 2 (S2) stable cell lines: Stable cell lines were produced by utilizing the *Drosophila* Expression System (Invitrogen, Carlsbad, Calif., USA). *Drosophila* S2 cells were transfected with ADAM33 recombinant DNA and the selection vector pCoHygro. Hygromycin resistant cell lines were selected for 6–8 weeks against 300 µg/ml hygromycin, and were stored in liquid nitrogen for an unlimited time.

Expression and Purification of wild type and mutant ADAM33: Stable cell lines containing the recombinant DNA were grown to 10–20×10$^6$ cells/ml in complete DES® Expression Medium (Invitrogen) supplemented with 0.3 mg/ml hygromycin, and 0.1% Pluronic F-68. The cells were collected using centrifugation at 1000 g for 15 minutes. The cell pellet was immediately suspended in Drosophila Serum-Free Medium supplemented with 1% DMSO and 0.1% Pluronic F-68 (Invitrogen, Carlsbad, Calif., USA) at a cell density of 2–4×10$^6$ cells/ml, and allowed to grow for 16–24 hours. Expression of ADAM33 was induced using 10 µM CdCl$_2$ in the presence of 200 µM ZnCl$_2$. The secreted ADAM33 was isolated from the conditioned media after was eluted with 250 mM imidazole in buffer C. The eluted protein was concentrated to 5–15 mg/ml, and then applied to a SUPERDEX-75 gel filtration column equilibrated with buffer GF (25 mM HEPES, pH 7.5, 150 mM NaCl, 10% glycerol, 50 mM imidazole). Fractions corresponding to the monomer of ADAM33 were pooled, and diluted to 0.3 mg/ml, flash-frozen in liquid nitrogen, and stored at −80° C. The presence of imidazole facilitated the separation of the pro domain from the catalytic domain, but also stabilizes the purified protein. When used for crystallography, the frozen protein was thawed on ice and concentrated to 10 mg/ml using Ultrafree®-15 Centrifugation Filter Device (Millipore, Bedford, Mass.). The thawed protein was immediately subjected to crystallization trials. Using this protocol a total of 1–9 mg of ADAM33 N231 Q comprising the amino acid sequence of SEQ ID NO: 8 and SEQ ID NO: 36 (the C-Terminal Ser-Gly His$_6$ Tag) was obtained from 1 liter of conditioned medium. 5 mM CaCl$_2$ is preferably included throughout the purification process. It is also preferred that 5 mM CaCl$_2$ is retained in the storage buffer.

Crystallization: The ADAM33 catalytic domain was expressed and purified using chromatographic methods as described herein. Monodisperse protein preparations were identified by particle size analysis using dynamic light scattering. Crystallization experiments were conducted and crystals were obtained by the hanging drop vapor diffusion method [Ducruix and Giege. *Crystallization of Nucleic Acids and Proteins. A practical approach*. Oxford University Press, (1992)].

A chimeric protein comprising the modified ADAM33 N231Q domain having the amino acid sequence of SEQ ID NO: 38 (1 μl; 6–10 mg/ml) in buffer GF was crystallized by mixing it with an equal volume of precipitant, and then placing it on the underside of a siliconized glass coverslip. The coverslip was sealed in close proximity to 1 ml of the precipitant solution. Crystals were grown from a droplet containing 0.5–1.0 μl of protein and 0.5–1.0 μl of the reservoir solution. The reservoir solution was either: (1) 0.05–0.2M CHAPs, pH 9.5 to 10.7, 10–40% (w/v) PEG 8000 (Fluka catalog #81268), with 0.0 to 0.4 M sodium chloride; or 0.05–0.2M CHES—NaOH buffer, pH 8.7–10.2, 10–40% (w/v) PEG 3000 (Fluka catalog #81227). 0.1 M buffer was particularly preferred. The crystallization plates were incubated at 4° C. Plate crystals of 0.02×0.2 mm grew over 2–30 days.

Crystals of the chimeric protein described above were soaked with a ligand to form crystals of the corresponding crystal of the protein-ligand complex. The ligand was N4-[2,2-dimethyl-1(S)-[(methylamino)carbonyl]propyl]-N1,2 (S)-dihydroxy-3(R)-(2-methylpropyl) butanediamide. One critical factor in the successful soaking in of the ligand into the protein crystal was the lowering of the pH of the buffer solution. The soaking/incubation conditions were 0.05–0.2M sodium-potassium phosphate pH 7.0, 10–40% (w/v) PEG 3000 (Fluka catalog #81227) at 4° C.–22° C.

Results

Homologs of human ADAM33 were identified using the BLASTP program [Altschul et al., *Nucleic Acids* 25:3389–3402 (1997)] and the protein sequence of human ADAM33 to search the SWISS-PROT protein sequence database along with the non-redundant(nr) and the protein data bank (pdb) sequence databases of GenBank at NCBI. The closely-related homologs selected included proteins from the ADAM family and the snake venom metalloproteases (MPs). The full-length sequences of the selected ADAM homologs and the sequences of the catalytic domains of the selected snake venom MPs derived from their X-ray structures were aligned with the full-length sequence of human ADAM33 using the program Clustal W with the default parameters. The alignment and known X-ray structures were analyzed to identify a canonical catalytic domain. The boundaries of the catalytic domain of human ADAM33 were deduced from the canonical domain. The boundaries were selected to include only cysteines of conserved disulfide bonds. From this analysis amino acid residue 409 of human ADAM33 was determined to be the C-terminus and the furin cleavage site was defined as the N-terminus of its catalytic domain. The subsequent cloning and expression of the human ADAM33 protein fragment disclosed below was based on this protein sequence analysis.

After designing an appropriate DNA construct, the expression of the ADAM33 catalytic domain in an eukaryotic cell line needed to be optimized. Surprisingly, induction conditions affected the cell growth, the separation of the pro domain and the catalytic domain, as well as the stability and proteolytic activity of the catalytic domain. The choice of metal chelate columns also unexpectedly affected the integrity of the protein. As suggested by the protocol from Invitrogen as well as other references, 0.5 mM $CuSO_4$ was initially used to induce the expression of wild type (WT) ADAM33 [Lehr, et. al. *Protein Expression and Purification* 19:362–368 (2000)]. However, under these induction conditions, $Cu^{2+}$ readily binds to the C-terminal $His_6$ Tag. Greater than 90% of the ADAM33 was purified as the complex of the pro and catalytic domains when conditioned medium was applied to the uncharged IDA metal chelate column (Chelating Sepharose Fast Flow, Amersham Pharmacia, Piscataway, N.J.) and the IDA metal chelate column was eluted with an imadazole gradient (10–200 mM) in buffer B. The protein was also found to be labile at 4° C. Induction coupled plasma (ICP) analysis indicated that the $Zn^{2+}$ content was less than optimum and that there was an incorporation of 10–30% of $Cu^{2+}$ in the purified protein sample. When the conditioned medium was exchanged into buffer A (25 mM HEPES, pH 7.0, 10% glycerol), and the sample was applied to the Ni-NTA column, the purified protein still retained the 30% $Cu^{2+}$.

The expression of the pro and catalytic domains of ADAM33 were driven by the *Drosophila* metallothionein promoter (PMT) in the recombinant DNA construct. This promoter is regulated by zinc-finger like transcription factors. The use of $Cd^{2+}$, $Zn^{2+}$, and their combination were evaluated for the system. $Zn^{2+}$ alone did not induce expression, whereas $Cd^{2+}$ and the combination of $Cd^{2+}$ and $Zn^{2+}$ did induce expression. The ratio of catalytic domain to the pro domain decreased as the concentration of zinc was increased. ADAM33 can be induced by $Cd^{2+}$ at the concentration of 1–25 μM with higher concentrations causing cytotoxcity . Additional $Zn^{2+}$ increased the ratio of secreted catalytic domain to the pro domain, and facilitated the subsequent purification. $Zn^{2+}$ concentrations of 10 μM–1 mM were effective, with the most effective concentration being 200 μM $Zn^{2+}$.

As both of the metal ions induce heat shock response in *Drosophila* cells, the optimum induction was achieved at 10 μM $Cd^{2+}$ and 200 μM $Zn^{2+}$.

Homogeneity and activity of ADAM33 N231Q: A public-domain partial sequence of human ADAM33 (CAC16509) was obtained from a BLAST search using the human ADAM33 sequence. Comparing this partial amino acid sequence with the human ADAM33 protein sequence, it was determined that this partial sequence was lacking the signal peptide region and the beginning of the pro-domain. The PROSITE database was used to search for sequence motifs of the partial sequence. Four N-glycosylation sites within the pro-domain and the catalytic domain were detected for this partial sequence by PROSITE. Using this information, two N-glycosylation sites were identified in the pro-domain and two N-glycosylation sites were identified in the catalytic domain of the human ADAM33 sequence. It was thereby shown that the wild type ADAM33 catalytic domain contains N-glycosylation sites at N231 and N276.

Glycosylation introduces heterogeneity to the protein, as two distinct migrating species are observed on SDS-PAGE. Amino acid substitutions for these two asparagine residues abolishes the glycan attachment, as confirmed by LC-MS analysis. In an effort to increase the homogeneity, single and double mutations at N231 and/or N276 were introduced to the WT recombinant DNA construct. The proteins were purified using SP-SEPHAROSE and Ni-NTA chromatography, and analyzed by peptide N-terminal sequencing, MALDI-TOF MS and LC-MS, and by enzymatic assays.

The effect of $CaCl_2$ on the stability of the ADAM33 N231Q catalytic domain as determined by thermal denaturation: The effect of the concentration of $CaCl_2$ on the retention of the secondary structure of the ADAM33 N231 Q catalytic domain was monitored by circular dichroism ($\lambda_{220}$ nm) as a function of temperature. A parallel study was performed replacing the $CaCl_2$ with NaCl to control for the effect of the corresponding increase in ionic strength. The ADAM33 N231Q catalytic domain was purified as described above and then diluted to 0.2 mg/ml. The sample was then dialyzed against 25 mM Hepes, pH 7.5, 5% glycerol overnight. 3 µM to 100 mM $CaCl_2$ was added to individual protein solutions as listed in Table 2. The temperature dependent protein denaturation was performed using a JASCO 810 spectropolarimeter under the following conditions:

Protein concentration: 0.2 mg/ml (based on a BioRad Protein Assay)
Cell length: 0.1 cm
Monitor wavelength: 220 nm
Temperature slope: 2° C./min
Measurement range: 20–80° C.

At an equivalent ionic strength, the ADAM33 catalytic domain showed significantly greater stability in the presence of $CaCl_2$ relative to NaCl.

Therefore, greater than 10 µM $CaCl_2$, and preferably between 0.3–100 mM $CaCl_2$ should be included to maintain the stability of this protein. A concentration of 5 mM $CaCl_2$ is suggested to be maintained in both the protein sample prior to its crystallization, and in all the buffers throughout purification. A summary of the results is provided in Table 2.

TABLE 2

THE EFFECT OF $CACL_2$ ON THE STABILITY OF ADAM33 N231Q

| $CaCl_2$, mM | Denaturation Temp., ° C. | ΔDenaturation Temp., ° C. |
|---|---|---|
| 0 | 43.5 | 0.0 |
| 0.003 | 50.6 | 7.1 |
| 0.03 | 52.9 | 9.4 |
| 0.3 | 53.9 | 10.4 |
| 0.5 | 56.9 | 13.4 |
| 1.0 | 57.9 | 14.4 |
| 2.5 | 60.6 | 17.1 |
| 5.0 | 61.5 | 18.0 |
| 10.0 | 63.3 | 19.8 |
| 25.0 | 64.6 | 21.1 |
| 50.0 | 65.6 | 22.1 |
| 100.0 | 65.2 | 21.7 |

The proteolytic activity of all of the wild type and modified ADAM33 catalytic domains were comparable. However, modified ADAM33 catalytic domains N231Q and N231Q/N276Q showed a significant increase in homogeneity relative to that of the wild type protein. After being stored in buffer GF for at least 15 days at 4° C. and 80° C., the proteins remained intact and active, as judged by peptide N-terminal sequencing, mass spectrometry and enzymatic assay.

The decreased homogeneity of the ADAM33 N276Q catalytic domain is due to the nature of heterogeneous glycosylation at the other N-glycosylation site, i.e., Asn231. This was confirmed by N-terminal peptide sequencing and the mass spectrum of the mutant N231Q/N276Q, which showed a N-terminus of "EARRTRK", and a molecular weight of 233542, eliminating the possibility of other forms of post translational modification.

Crystallographic analysis of ADAM33: Crystals of the ADAM33 catalytic domain were obtained by the hanging drop vapor diffusion method as described above.

Prior to data collection, crystals were washed with the reservoir solution of the crystallization setup and transferred into the same solution with 10% glycerol added. The crystals were then flash-cooled in a nitrogen stream at 95° K. X-ray diffraction was collected using a Rigaku generator equipped with a Raxis 4++ detector. Data were integrated and scaled using the HKL package. The crystal structure was solved with molecular replacement using the search model atrolysin C (PDB entry 1ATL). The Refinement of the structure was performed using the program CNX which is a commercial version of CNS [Adams et al., Proc. Natl. Acad. Sci. USA, 94:5018–5023 (1997)].

TABLE 3

DATA COLLECTION STATISTICS

| Resolution | 24-2.3 Å |
|---|---|
| No. of collected reflections | 45040 |
| No. of unique reflections (F >= 0) | 7391 |
| R-sym | 0.128 |
| Percent of theoretical (I/s >= 1) | 93% |
| Unit Cell | a = 53.8 Å, b = 66.1 Å, c = 96.1 Å, $\alpha = \beta = \gamma = 90°$ |
| Space Group | $C222_1$ |
| Asymmetric unit | 1 molecule |

TABLE 4

REFINED STATISTICS

| Theoretical number of reflections | 7907 | |
|---|---|---|
| Number of unobserved reflections | 549 | (6.9%) |
| Number of reflections in working set | 6957 | (88.9%) |
| Number of reflections in test set | 401 | (5.1%) |
| Number of protein residues | 200 | |
| Number of ions | 2 | |
| R-factor | 0.258 | |
| R-free | 0.296 | |
| RMSD bond length | 0.0092 Å | |
| RMSD bond angles | 1.66° | |

Example 2

Peptide Substrates of ADAM33

Materials and Methods

The peptide substrate (50 µM) was incubated with or without ADAM33 (0.1–0.5 µM) in assay buffer (20 mM HEPES, pH 7.5, 0.5 M NaCl, 0.2 mg/ml bovine serum albumin (BSA)) for 2 hours (h) at room temperature (RT) in the presence or absence of various inhibitors [5 mM 1,10-phenanthroline, or a protease inhibitor cocktail (2 µg/ml leupeptin, 0.4 µM benzamidine, 10 µg/ml soybean trypsin inhibitor and 0.5 mM iodoacetamide)]. The reaction was stopped by adding 10% trifluoroacetic acid (TFA) to a final concentration of 1% and samples were analyzed on Agilent HPLC model 1100 with C8 column. Solvents were: A, 0.1% TFA in water; B, 0.09% TFA in acetonitrile. A linear gradient from 2 to 42% B was run over 7 min at 1.5 ml/min and the eluate was monitored at 214 nm. The percentage of peptide cleavage was calculated using the peak area of the cleaved products divided by the sum of the peak areas of both the products and the remaining substrate. The cleavage sites of the peptide were identified by matrix-assisted laser-desorption/ionization time-of-flight (MALDI-TOF) mass spectrometry.

Specificity constants of peptide substrates, APP and KL-1, were obtained by using the HPLC assay described above. In brief, ADAM33cat (80 nM) was incubated with peptide substrate (30–2000 µM) in assay buffer for 10–60 min at RT. Reactions were timed to allow less than 15% turnover of the substrate. The initial cleavage velocities of the peptides were obtained by plotting cleaved product versus reaction time. The specificity constants, $k_{cat}/K_m$, were determined based on best fit of the data with the Michaelis-Menten equation when substrate concentration $S<<K_m$.

Results

To identify peptide substrates of ADAM33, peptides corresponding to cleavage sites of proteins known to be cleaved by ADAMs and matrix metalloproteinases (MMP) were tested for cleavage by ADAM33. Four peptides from the following proteins were found to be cleaved by ADAM33: KL-1 (PPVAASSLRN; SEQ ID NO: 42), APP (YEVHHQKLVF; SEQ ID NO: 43), TRANCE (VGSQHIRAEK; SEQ ID NO: 44), and insulin B chain (HLVEALYLVC; SEQ ID NO: 45). ADAM33 cleaved the APP peptide at H*Q, KL-1 peptide at A*S, insulin B chain peptide at A*L, and human TRANCE peptide at H*I. Kinetic constants ($k_{cat}$, $K_m$ and $k_{cat}/K_m$) for KL-1 and APP were determined. The initial cleavage velocities of the peptides were measured under conditions of low turnover (<15%) so that the substrate concentration did not change significantly. The $k_{cat}$, $K_m$ and $k_{cat}/K_m$ values of KL-1 were determined to be $0.7\pm0.1$ s$^{-1}$, $3.0\pm0.1$ mM, and $(2.6\pm0.5)\times 10^2$ M$^{-1}$ s$^{-1}$ (n=3), respectively. For APP, the $k_{cat}$, $K_m$ and $k_{cat}/K_m$ values were $0.2\pm0.1$ s$^{-1}$, $1.0\pm0.1$ mM and $(1.6\pm0.3)\times 10^2$ M$^{-1}$ s$^{-1}$ (n=2), respectively.

Example 3

Inhibitors of ADAM33

Materials and Methods

The inhibition dissociation constants ($K_i$) for inhibitors were determined as follows: an HPLC assay was performed in the presence or absence of inhibitors for 2 h at RT using ADAM33cat (80 nM) and KL-1 peptide substrate (100 µM). For testing tissue inhibitor of metalloproteinases (TIMPs), ADAM33 and human TIMPs were pre-incubated for 1 h at RT. Serial dilutions of TIMPs or synthetic inhibitors were tested starting at 4 µM (TIMP-2, -3, 4), 2 µM (TIMP-1, IK682), 20 µM (Marimastat), or 200 µM (Immunex compound 1: N-{DL-[2-(hydroxyamino-carbonyl)methyl]4-methylpentanoyl}-L-3-(tertbutyl)glycyl-L-alanine,2-aminoethylamide). Initial velocities were calculated by dividing cleaved product over reaction time. The initial velocities were plotted as a function of inhibitor concentration. For tight binding inhibitors (IK682, TIMP-3), the apparent inhibitor dissociation constants ($K_i$ app values) were calculated by fitting the curve to the following modified Morrison's equation:

$$v_i = v_o\{[(E_o-I_o-K_i^{app})^2 + 4K_i^{app}E_o]^{1/2} + (E_o-I_oK_i^{app})\}/2E_o$$

where $K_i^{app}=K_i(1+S/K_m)$, $v_o$ is the uninhibited initial velocity, $v_i$ is the initial velocity in the presence of inhibitor at any given inhibitor concentration $I_o$, and $E_o$ is initial enzyme concentration. When the substrate concentration $S<<K_m$, $K_i^{app}$ is approximately equal to $K_i$. For all other less potent inhibitors, the inhibitor dissociation constants ($K_i$ values) were determined by fitting the data to the rearranged Michaelis-Menten equation for competitive inhibitor kinetics when $S<<K_m$: $v_i=v_o/(1+I_o/K_i)$.

Inhibition of human ADAM17 by human TIMPs was determined as follows: ADAM17 (1 nM) was pre-incubated with serial dilutions of TIMP-1 (0–4 µM), TIMP-2 (0–1 µM), TIMP-3 (0–0.2 µM), or TIMP-4 (0–4 µM), in assay buffer (25 mM HEPES, pH7.5, 5 mM $CaCl_2$, 0.1 mM $ZnCl_2$) for 1 h at RT, followed by addition of the fluorogenic pro-TNF-alpha substrate (25 µM), K(mca)SPLAQAVRSSS-RK(dnp) (SEQ ID NO: 46). The reaction velocities were measured using the GEMINI fluorescence reader at 320/380 nm for 1 h and inhibition dissociation constants were calculated by fitting the data to Morrison equation (TIMP-2 and TIMP-3) or Michaelis-Menten equation (TIMP-1 and TIMP-4) as described above.

A fluorogenic substrate, K(Dabcyl)LPPVAASSLRNDE(edans)K (SEQ ID NO: 47), based on peptide KL-1 was synthesized and used to measure ADAM33 enzyme activity. The concentration of ADAM33cat was determined to be 780 µM, using a molar extinction coefficient of 26,780 M$^{-1}$ cm$^{-1}$ at 280 nm. The enzyme was titrated with a serial dilution of inhibitor IK682 (0–2 µM) in the presence of substrate (30 µM) in assay buffer (20 mM HEPES, pH 7.5, 0.5 M NaCl) and the reaction velocity was measured at excitation/emission wavelength 340/505 nm with a GEMINI fluorescence reader (Molecular Devices, Sunnyvale, Calif.) for 5 min. The initial velocities were plotted as a function of inhibitor concentration, and the active enzyme concentration was calculated by fitting the curve to the modified Morrison's equation as described above.

Results

The cleavage of the KL-1 peptide by ADAM33 was used to evaluate the effect of different classes of protease inhibitors. Inhibition constants of several hydroxamate compounds, known to inhibit either ADAM17 [IK682, and the Immunex compound 1] or MMPs [Marimastat], were determined. The compound IK682 was the most potent inhibitor of ADAM33 activity with a K value of $23\pm7$ nM (n=2). Marimastat was a less potent inhibitor with a $K_i$ value of $157\pm38$ nM (n=2). The Immunex compound 1 was the least potent, with a $K_i$ value of $2847\pm152$ nM (n=2). Human TIMP-1, -2, -3 and -4, endogenous inhibitors of MMPs and ADAMs, were tested for inhibition of ADAM33 activity. TIMP-3 ($K_i=64\pm16$ nM, n=2) and TIMP4 ($K_i=223\pm16$ nM, n=2) demonstrated significant ADAM33 inhibitory activity while there was no inhibition by TIMP-1 at 2 mM and weak inhibition by TIMP-2 ($K_i=1373\pm269$ nM, n=2). By comparison, human ADAM17 activity was inhibited by TIMP-2, TIMP-3 and TIMP4, and weakly inhibited by TIMP-1.

Example 4

Association of Human ADAM33 Pro and Cat Domains

Materials and Methods

A 12-mer peptide (i.e. Ac-LPPVAASSLNRD-NH$_2$; SEQ ID NO: 48), derived from human mast-cell growth factor (accession number NP-038626) was synthesized as a substrate for ADAM33. Reactions were initiated by addition of 200 nM enzyme to appropriate amounts of substrate in assay buffer (25 mM HEPES, pH 7.5, 0.5 M NaCl, 0.1% n-octyl-β-D-glucoside), incubated at 22° C. for 2 h and subsequently quenched with 1% TFA. When inhibitors were evaluated, the enzyme and inhibitors were preincubated at 22° C. for 30 min prior to initiation of the assays. Substrate and products were separated by HPLC using a C-8 reverse phase column (Zobrax 3.5 µm, 4.6 mmD/5 cmL, Agilent, Palo Alto, Calif., 0.1% TFA acetonitrile/$H_2O$). Elution was monitored at 214 nm, and peaks identified by mass spectroscopy. Initial rates of proteolysis were determined using reactions in which less than 10% of the substrate was consumed. $k_{cat}/K_m$ values were calculated assuming the enzymes were 100% active.

Production of ADAM33 and mutants thereof were produced essentially as described in Example 1. Proteolytic assays and methods for determining catalytic rates are essentially as described in Examples 2 and 3.

Results

When recombinant ADAM33 zymogen was expressed in *Drosophila* S2 cells, the secreted ADAM33 was processed at $RGRR_{203} \downarrow EARR$, similar to observations in mammalian cells. Based on two-dimensional gel electrophoresis analysis, the isoelectric points of the pro and CAT domains were estimated to be 8.3 and 9.6, respectively, suggesting that separation by cation exchange chromatography might be possible. However, the majority of CAT remained associated with the pro domain during chromatography (i.e., ion exchange, hydrophobic interaction, lectin affinity, Ni-NTA affinity, gel filtration, etc.), and only 10–20% of pure CAT could be isolated at the gel filtration stage (see also Example 1). Earlier studies have indicated that most zinc-containing metalloproteases, including ADAMs, are latent until the cysteine switch residue is transiently dissociated from the catalytic zinc ion via reacting with thiol modifying reagents, such as p-aminophenylmercuric acetate (APMA) and iodoacetamide. The disruption of the cysteine-zinc coordination can also be facilitated by detergents, heat treatment and denaturants. To test these possibilities for ADAM33, 50 µM–1 mM APMA or 1 mM iodoacetamide), in the presence and absence of nonionic detergents (i.e. n-octyl-β-D-glucoside, n-octyl-β-D-maltoside), were added to the conditioned medium and the purification buffers. However, the secreted pro/CAT complex remained tightly associated. The purified pro/CAT complex was incubated with 50 µM–1 mM APMA at room temperature for 30 minutes prior to application onto a size exclusion column (Superdex 75, Amersham Pharmacia, N.J.). No further separation of the two domains was observed.

To examine whether the postulated free thiol groups of Cys-131 and Cys-179 contribute to the observed tight association between pro and CAT, they were replaced with Ala. The resulting mutant proteins (C131A (SEQ ID NO: 49), C179A (SEQ ID NO: 50) & C131A/C179A (SEQ ID NO: 51)) were expressed at a level comparable to that of the wild-type protein, processed at the predicted pro-CAT junction $RGRR_{203} \downarrow EARR$, and secreted into the conditioned medium. The mutant proteins also behaved almost identically to the wild-type protein during chromatography. More than 80% of the protease domain remained associated with the pro domain, and the heterodimer was not disrupted by treatment with APMA and/or detergents. The charged residues flanking the cysteine switch have been implicated in pro/CAT binding in MMPs. The corresponding human ADAM33 residues, Lys-176 and Asp-183, were substituted by Ile and Asn, respectively. However, in human ADAM33, dissociation of the pro/CAT heterodimeric complex was not facilitated by mutation of these residues in the double mutants (K176I/C179A (SEQ ID NO: 52) and C179A/D183N (SEQ ID NO: 53)). These findings indicate that the putative cysteine switch, including the flanking charged residues, has little contribution to the association of the zymogen complex.

Mouse ADAM33 shares 70% sequence identity with the human homolog but its pro domain lacks a cysteine switch residue. If the association of the pro and CAT domain were indeed mediated by the cysteine switch mechanism, absence of such a residue should lead to weakened pro-CAT interaction. To test this hypothesis, a soluble mouse ADAM33 zymogen form was expressed essentially as described above in the *Drosophila* S2 system. The zymogen was expressed, efficiently processed at the pro-CAT junction sequence $RVRR_{224} \downarrow EARR$ and secreted into the conditioned medium. However, only pro/CAT complex, not CAT alone, was isolated using a purification strategy similar to that for the protease domain.

The MCF substrate peptide (SEQ ID NO: 48) was used to evaluate proteolytic activity of the protein. The wild-type ADAM33 cleaved the peptide between the residues corresponding to Ala-190 and Ser-191. As expected, the activity was completely abolished in the presence of 1 mM 1,10-phenanthroline or EDTA, supporting zinc specific metalloprotease activity. Under the assay conditions (i.e. 200 nM enzyme and 10–500 µM substrate in the assay buffer at room temperature), the rate of product generation was linear with time for 4 h. Initial velocity was also linear with substrate concentration, suggesting a $K_m$ value greater than the highest tested concentration (500 µM). Using the peptide substrate assay, the CAT domain exhibited an estimated catalytic efficiency of $2.6 \pm 0.5) \times 10^2$ $M^{-1}$ $s^{-1}$. The catalytic efficiency of the pro/CAT complex, tested at a concentration of 50 nM–1 µM, was comparable to that of the CAT domain, indicating a lack of inhibitory effects of the pro domain under these assay conditions.

The results showing comparable kcat/Km values for both purified CAT and pro/CAT proteins suggests that either pro/CAT has completely dissociated under the assay conditions (due to much lower protein concentrations used in the assays versus purification), or the pro domain does not block the active site. To distinguish the two possibilities, a single chain zymogen form of ADAM33 (R203T/R207S; (SEQ ID NO:54)) was engineered and produced using the methods essentially as described above. The catalytic efficiency of the pro-CAT single chain zymogen form also showed no significant difference to that of the CAT domain, supporting the latter hypothesis. However, it is highly probable that when ADAM33 interacts with a protein substrate, the pro domain would act as an inhibitor through steric hindrance. Our findings also imply that the pro domain of ADAM33 might act as an intramolecular chaperone to assist folding and stabilization of the protease domain.

The present invention is not to be limited in scope by the specific embodiments describe herein. Indeed, various modifications of the invention in addition to those described herein will become apparent to those skilled in the art from the foregoing description. Such modifications are intended to fall within the scope of the appended claims.

It is further to be understood that all base sizes or amino acid sizes, and all molecular weight or molecular mass values, given for nucleic acids or polypeptides are approximate, and are provided for description.

Various publications are cited herein, the disclosures of which are incorporated by reference in their entireties.

What is claimed is:

1. An isolated polypeptide comprising the amino acid sequence of SEQ ID NO: 6 wherein the amino acid at position 28 is not asparagine.

2. A chimeric protein comprising the polypeptide of claim 1.

3. A polypeptide comprising a modified ADAM33 catalytic domain, wherein said modified ADAM33 catalytic domain comprises the amino acid sequence of SEQ ID NO: 6 wherein the amino acid at position 28 is not asparagine and wherein said polypeptide catalyzes the proteolytic cleavage of a peptide comprising the amino acid sequence of SEQ ID NO: 35.

4. The polypeptide of claim 1 comprising the amino acid sequence of SEQ ID NO: 8.

5. A chimeric protein comprising the polypeptide of claim 4.

6. The chimeric protein of claim 5 comprising the amino acid sequence of SEQ ID NO: 38.

7. The polypeptide of claim 1 comprising a secretion signal sequence comprising the amino acid sequence of SEQ ID NO: 22.

8. An isolated ADAM33 polypeptide comprising the ADAM33 catalytic domain comprising the amino acid sequence of either SEQ ID NO: 6 wherein the amino acid at position 28 is not asparagine or SEQ ID NO: 8 and wherein said catalytic domain is free of the ADAM33 pro domain, said polypeptide obtained by a method comprising culturing a host cell comprising a vector comprising a polynucleotide encoding the polypeptide, linked to a metallothionein promoter, in a culture medium, wherein 1 to 25 µM $Cd^{2+}$ and 10 µM to 1 mM $Zn^{2+}$ are added to the medium.

9. An isolated polypeptide comprising the amino acid sequence of either SEQ ID NO: 6 wherein the amino acid at position 28 is not asparagine or SEQ ID NO: 8 produced by a method comprising culturing, in a culture medium, a host cell comprising a vector comprising a polynucleotide encoding the polypeptide.

10. A crystal comprising a polypeptide consisting of SEQ ID NO: 38 and the ligand N4-[2,2-dimethyl-1(S)-[(methylamino)carbonyl]propyl]-N1,2(S)-dihydroxy-3(R)-(2-methylpropyl) butanediamide and having the space group $C222_1$ and a unit cell with the following parameters: a=53.8Å, b=66.1 Å, and c=69.1 Å.

* * * * *

SEQUENCE LISTING

<160> NUMBER OF SEQ ID NOS: 54

<210> SEQ ID NO 1
<211> LENGTH: 1239
<212> TYPE: DNA
<213> ORGANISM: homo sapiens

<400> SEQUENCE: 1

```
atgaagttat gcatattact ggccgtcgtg gcctttgttg gcctctcgct cgggagatct      60
ccatggcccg gggtaccgct tcaaggacat atccctgggc agccagtcac cccgcactgg     120
gtcctggatg gacaaccctg gcgcaccgtc agcctggagg agccggtctc gaagccagac     180
atggggctgg tggccctgga ggctgaaggc caggagctcc tgcttgagct ggagaagaac     240
cacaggctgc tggccccagg atacatagaa acccactacg gcccagatgg gcagccagtg     300
gtgctggccc ccaaccacac ggatcattgc cactaccaag gcgagtaag  ggtttcccc      360
gactcctggg tagtcctctg cacctgctct gggatgagtg gcctgatcac cctcagcagg     420
aatgccagct attatctgcg tccctggcca ccccggggct ccaaggactt ctcaacccac     480
gagatctttc ggatggagca gctgctcacc tggaaaggaa cctgtggcca cagggatcct     540
gggaacaaag cggcatgac  cagtcttcct ggtggtcccc agagcagggg caggcgagaa     600
gcgcgcagga cccggaagta cctggaactg tacattgtgg cagaccacac cctgttcttg     660
actcggcacc gaaacttgaa ccacaccaaa cagcgtctcc tggaagtcgc caactacgtg     720
gaccagcttc tcaggactct ggacattcag gtggcgctga ccggcctgga ggtgtggacc     780
gagcgggacc gcagccgcgt cacgcaggac gccaacgcca cgctctgggc cttcctgcag     840
tggcgccggg gctgtgggc  gcagcggccc cacgactccg cgcagctgct cacgggccgc     900
gccttccagg gcgccacagt gggcctggcc cccgtcgagg gcatgtgccg cgccgagagc     960
tcgggaggcg tgagcacgga ccactcggag ctccccatcg gcgccgcagc caccatggcc    1020
catgagatcg gccacagcct cggcctcagc cacgaccccg acggctgctg cgtggaggct    1080
gcggccgagt ccggaggctg cgtcatggct gcggccaccg gcacccgtt  ccgcgcgtg    1140
ttcagcgcct gcagccgccg ccagctgcgc gccttcttcc gcaaggggg  cggcgcttgc    1200
ctctccaatg ccccgtcagg acatcatcat caccatcat                           1239
```

<210> SEQ ID NO 2
<211> LENGTH: 405
<212> TYPE: PRT
<213> ORGANISM: homo sapiens

<400> SEQUENCE: 2

```
Met Lys Leu Cys Ile Leu Leu Ala Val Val Ala Phe Val Gly Leu Ser
1               5                   10                  15

Leu Gly Arg Ser Pro Trp Pro Gly Val Pro Leu Gln Gly His Ile Pro
            20                  25                  30

Gly Gln Pro Val Thr Pro His Trp Val Leu Asp Gly Gln Pro Trp Arg
        35                  40                  45

Thr Val Ser Leu Glu Glu Pro Val Ser Lys Pro Asp Met Gly Leu Val
    50                  55                  60

Ala Leu Glu Ala Glu Gly Gln Glu Leu Leu Leu Glu Leu Glu Lys Asn
65                  70                  75                  80

His Arg Leu Leu Ala Pro Gly Tyr Ile Glu Thr His Tyr Gly Pro Asp
                85                  90                  95
```

```
Gly Gln Pro Val Val Leu Ala Pro Asn His Thr Asp His Cys His Tyr
            100                 105                 110

Gln Gly Arg Val Arg Gly Phe Pro Asp Ser Trp Val Leu Cys Thr
            115                 120                 125

Cys Ser Gly Met Ser Gly Leu Ile Thr Leu Ser Arg Asn Ala Ser Tyr
        130                 135                 140

Tyr Leu Arg Pro Trp Pro Pro Arg Gly Ser Lys Asp Phe Ser Thr His
145                 150                 155                 160

Glu Ile Phe Arg Met Glu Gln Leu Leu Thr Trp Lys Gly Thr Cys Gly
                165                 170                 175

His Arg Asp Pro Gly Asn Lys Ala Gly Met Thr Ser Leu Pro Gly Gly
                180                 185                 190

Pro Gln Ser Arg Gly Arg Arg Glu Ala Arg Thr Arg Lys Tyr Leu
            195                 200                 205

Glu Leu Tyr Ile Val Ala Asp His Thr Leu Phe Leu Thr Arg His Arg
        210                 215                 220

Asn Leu Asn His Thr Lys Gln Arg Leu Leu Glu Val Ala Asn Tyr Val
225                 230                 235                 240

Asp Gln Leu Leu Arg Thr Leu Asp Ile Gln Val Ala Leu Thr Gly Leu
                245                 250                 255

Glu Val Trp Thr Glu Arg Asp Arg Ser Arg Val Thr Gln Asp Ala Asn
                260                 265                 270

Ala Thr Leu Trp Ala Phe Leu Gln Trp Arg Arg Gly Leu Trp Ala Gln
        275                 280                 285

Arg Pro His Asp Ser Ala Gln Leu Leu Thr Gly Arg Ala Phe Gln Gly
290                 295                 300

Ala Thr Val Gly Leu Ala Pro Val Glu Gly Met Cys Arg Ala Glu Ser
305                 310                 315                 320

Ser Gly Gly Val Ser Thr Asp His Ser Glu Leu Pro Ile Gly Ala Ala
                325                 330                 335

Ala Thr Met Ala His Glu Ile Gly His Ser Leu Gly Leu Ser His Asp
                340                 345                 350

Pro Asp Gly Cys Cys Val Glu Ala Ala Ala Glu Ser Gly Gly Cys Val
            355                 360                 365

Met Ala Ala Ala Thr Gly His Pro Phe Pro Arg Val Phe Ser Ala Cys
370                 375                 380

Ser Arg Arg Gln Leu Arg Ala Phe Phe Arg Lys Gly Gly Gly Ala Cys
385                 390                 395                 400

Leu Ser Asn Ala Pro
            405

<210> SEQ ID NO 3
<211> LENGTH: 618
<212> TYPE: DNA
<213> ORGANISM: homo sapiens

<400> SEQUENCE: 3
gaagcgcgca ggacccggaa gtacctggaa ctgtacattg tggcagacca caccctgttc      60
ttgactcggc accgaaactt gaaccacacc aaacagcgtc tcctggaagt cgccaactac     120
gtggaccagc ttctcaggac tctggacatt caggtggcgc tgaccggcct ggaggtgtgg     180
accgagcggg accgcagccg cgtcacgcag gacgccaacg ccacgctctg ggccttcctg     240
cagtggcgcc gggggctgtg ggcgcagcgg ccccacgact ccgcgcagct gctcacgggc     300
```

```
cgcgccttcc agggcgccac agtgggcctg gcgcccgtcg agggcatgtg ccgcgccgag    360
agctcgggag gcgtgagcac ggaccactcg gagctcccca tcggcgccgc agccaccatg    420
gcccatgaga tcggccacag cctcggcctc agccacgacc ccgacggctg ctgcgtggag    480
gctgcggccg agtccggagg ctgcgtcatg gctgcggcca ccgggcaccc gtttccgcgc    540
gtgttcagcg cctgcagccc cgccagctg cgcgccttct ccgcaaggg gggcggcgct    600 tgcctctcca atgccccg                                                  618
```

```
<210> SEQ ID NO 4
<211> LENGTH: 206
<212> TYPE: PRT
<213> ORGANISM: homo sapiens

<400> SEQUENCE: 4
```

| | | | | | | | | | | | | | | | |
|---|---|---|---|---|---|---|---|---|---|---|---|---|---|---|---|
| Glu | Ala | Arg | Arg | Thr | Arg | Lys | Tyr | Leu | Glu | Leu | Tyr | Ile | Val | Ala | Asp |
| 1 | | | | 5 | | | | | 10 | | | | | 15 | |
| His | Thr | Leu | Phe | Leu | Thr | Arg | His | Arg | Asn | Leu | Asn | His | Thr | Lys | Gln |
| | | | | 20 | | | | | 25 | | | | | 30 | |
| Arg | Leu | Leu | Glu | Val | Ala | Asn | Tyr | Val | Asp | Gln | Leu | Leu | Arg | Thr | Leu |
| | | | 35 | | | | | 40 | | | | | 45 | | |
| Asp | Ile | Gln | Val | Ala | Leu | Thr | Gly | Leu | Glu | Val | Trp | Thr | Glu | Arg | Asp |
| | 50 | | | | | 55 | | | | | 60 | | | | |
| Arg | Ser | Arg | Val | Thr | Gln | Asp | Ala | Asn | Ala | Thr | Leu | Trp | Ala | Phe | Leu |
| 65 | | | | | 70 | | | | | 75 | | | | | 80 |
| Gln | Trp | Arg | Arg | Gly | Leu | Trp | Ala | Gln | Arg | Pro | His | Asp | Ser | Ala | Gln |
| | | | | 85 | | | | | 90 | | | | | 95 | |
| Leu | Leu | Thr | Gly | Arg | Ala | Phe | Gln | Gly | Ala | Thr | Val | Gly | Leu | Ala | Pro |
| | | | | 100 | | | | | 105 | | | | | 110 | |
| Val | Glu | Gly | Met | Cys | Arg | Ala | Glu | Ser | Ser | Gly | Gly | Val | Ser | Thr | Asp |
| | | | 115 | | | | | 120 | | | | | 125 | | |
| His | Ser | Glu | Leu | Pro | Ile | Gly | Ala | Ala | Ala | Thr | Met | Ala | His | Glu | Ile |
| | | 130 | | | | | 135 | | | | | 140 | | | |
| Gly | His | Ser | Leu | Gly | Leu | Ser | His | Asp | Pro | Asp | Gly | Cys | Cys | Val | Glu |
| 145 | | | | | 150 | | | | | 155 | | | | | 160 |
| Ala | Ala | Ala | Glu | Ser | Gly | Gly | Cys | Val | Met | Ala | Ala | Ala | Thr | Gly | His |
| | | | | 165 | | | | | 170 | | | | | 175 | |
| Pro | Phe | Pro | Arg | Val | Phe | Ser | Ala | Cys | Ser | Arg | Arg | Gln | Leu | Arg | Ala |
| | | | 180 | | | | | 185 | | | | | 190 | | |
| Phe | Phe | Arg | Lys | Gly | Gly | Gly | Ala | Cys | Leu | Ser | Asn | Ala | Pro | | |
| | | | 195 | | | | | 200 | | | | | 205 | | |

```
<210> SEQ ID NO 5
<211> LENGTH: 618
<212> TYPE: DNA
<213> ORGANISM: homo sapiens
<220> FEATURE:
<221> NAME/KEY: misc_feature
<222> LOCATION: (82)..(84)
<223> OTHER INFORMATION: nnn can be any codon that does not encode
      asparagine.

<400> SEQUENCE: 5
```

```
gaagcgcgca ggacccggaa gtacctggaa ctgtacattg tggcagacca caccctgttc     60
ttgactcggc accgaaactt gnnncacacc aaacagcgtc tcctggaagt cgccaactac    120
gtggaccagt tctcaggac tctggacatt caggtggcgc tgaccggcct ggaggtgtgg    180
accgagcggg accgcagccg cgtcacgcag gacgccaacg ccacgctctg ggccttcctg    240
```

-continued

```
cagtggcgcc gggggctgtg ggcgcagcgg ccccacgact ccgcgcagct gctcacgggc      300
cgcgccttcc agggcgccac agtgggcctg gcgcccgtcg agggcatgtg ccgcgccgag      360
agctcgggag gcgtgagcac ggaccactcg gagctcccca tcggcgccgc agccaccatg      420
gcccatgaga tcggccacag cctcggcctc agccacgacc ccgacggctg ctgcgtggag      480
gctgcggccg agtccggagg ctgcgtcatg gctgcggcca ccgggcaccc gtttccgcgc      540
gtgttcagcg cctgcagccg ccgccagctg cgcgccttct ccgcaaggg gggcggcgct      600 tgcctctcca atgccccg                                                    618
```

<210> SEQ ID NO 6
<211> LENGTH: 206
<212> TYPE: PRT
<213> ORGANISM: homo sapiens
<220> FEATURE:
<221> NAME/KEY: misc_feature
<222> LOCATION: (28)..(28)
<223> OTHER INFORMATION: Xaa can be any amino acid except asparagine.

<400> SEQUENCE: 6

```
Glu Ala Arg Arg Thr Arg Lys Tyr Leu Glu Leu Tyr Ile Val Ala Asp
1               5                   10                  15

His Thr Leu Phe Leu Thr Arg His Arg Asn Leu Xaa His Thr Lys Gln
            20                  25                  30

Arg Leu Leu Glu Val Ala Asn Tyr Val Asp Gln Leu Leu Arg Thr Leu
        35                  40                  45

Asp Ile Gln Val Ala Leu Thr Gly Leu Glu Val Trp Thr Glu Arg Asp
    50                  55                  60

Arg Ser Arg Val Thr Gln Asp Ala Asn Ala Thr Leu Trp Ala Phe Leu
65                  70                  75                  80

Gln Trp Arg Arg Gly Leu Trp Ala Gln Arg Pro His Asp Ser Ala Gln
                85                  90                  95

Leu Leu Thr Gly Arg Ala Phe Gln Gly Ala Thr Val Gly Leu Ala Pro
            100                 105                 110

Val Glu Gly Met Cys Arg Ala Glu Ser Ser Gly Gly Val Ser Thr Asp
        115                 120                 125

His Ser Glu Leu Pro Ile Gly Ala Ala Ala Thr Met Ala His Glu Ile
    130                 135                 140

Gly His Ser Leu Gly Leu Ser His Asp Pro Asp Gly Cys Cys Val Glu
145                 150                 155                 160

Ala Ala Ala Glu Ser Gly Gly Cys Val Met Ala Ala Thr Gly His
                165                 170                 175

Pro Phe Pro Arg Val Phe Ser Ala Cys Ser Arg Gln Leu Arg Ala
            180                 185                 190

Phe Phe Arg Lys Gly Gly Gly Ala Cys Leu Ser Asn Ala Pro
        195                 200                 205
```

<210> SEQ ID NO 7
<211> LENGTH: 1236
<212> TYPE: DNA
<213> ORGANISM: homo sapiens
<220> FEATURE:
<221> NAME/KEY: misc_feature
<222> LOCATION: (84)..(84)
<223> OTHER INFORMATION: n can be a or g

<400> SEQUENCE: 7

```
gaagcgcgca ggacccggaa gtacctggaa ctgtacattg tggcagacca caccctgttc      60
```

-continued

```
ttgactcggc accgaaactt gcancacacc aaacagcgtc tcctggaagt cgccaactac    120
gtggaccagc ttctcaggac tctggacatt caggtggcgc tgaccggcct ggaggtgtgg    180
accgagcggg accgcagccg cgtcacgcag gacgccaacg ccacgctctg ggccttcctg    240
cagtggcgcc gggggctgtg ggcgcagcgg ccccacgact ccgcgcagct gctcacgggc    300
cgcgccttcc agggcgccac agtgggcctg gcgcccgtcg agggcatgtg ccgcgccgag    360
agctcgggag gcgtgagcac ggaccactcg gagctcccca tcggcgccgc agccaccatg    420
gcccatgaga tcggccacag cctcggcctc agccacgacc ccgacggctg ctgcgtggag    480
gctgcggccg agtccggagg ctgcgtcatg gctgcggcca ccgggcaccc gtttccgcgc    540
gtgttcagcg cctgcagccg ccgccagctg cgcgccttct tccgcaaggg gggcggcgct    600
tgcctctcca atgccccgga agcgcgcagg acccggaagt acctggaact gtacattgtg    660
gcagaccaca ccctgttctt gactcggcac cgaaacttgc agcacaccaa acagcgtctc    720
ctggaagtcg ccaactacgt ggaccagctt ctcaggactc tggacattca ggtggcgctg    780
accggcctgg aggtgtggac cgagcgggac cgcagccgcg tcacgcagga cgccaacgcc    840
acgctctggg ccttcctgca gtggcgccgg gggctgtggg cgcagcggcc ccacgactcc    900
gcgcagctgc tcacgggccg cgccttccag ggcgccacag tgggcctggc gcccgtcgag    960
ggcatgtgcc gcgccgagag ctcgggaggc gtgagcacgg accactcgga gctccccatc   1020
ggcgccgcag ccaccatggc ccatgagatc ggccacagcc tcggcctcag ccacgacccc   1080
gacggctgct gcgtggaggc tgcggccgag tccggaggct gcgtcatggc tgcggccacc   1140 ggcacccgt tccgcgcgt gttcagcgcc tgcagccgcc gccagctgcg cgccttcttc   1200
cgcaaggggg gcggcgcttg cctctccaat gccccg                             1236
```

<210> SEQ ID NO 8
<211> LENGTH: 206
<212> TYPE: PRT
<213> ORGANISM: homo sapiens

<400> SEQUENCE: 8

```
Glu Ala Arg Arg Thr Arg Lys Tyr Leu Glu Leu Tyr Ile Val Ala Asp
1               5                   10                  15

His Thr Leu Phe Leu Thr Arg His Arg Asn Leu Gln His Thr Lys Gln
            20                  25                  30

Arg Leu Leu Glu Val Ala Asn Tyr Val Asp Gln Leu Leu Arg Thr Leu
        35                  40                  45

Asp Ile Gln Val Ala Leu Thr Gly Leu Glu Val Trp Thr Glu Arg Asp
    50                  55                  60

Arg Ser Arg Val Thr Gln Asp Ala Asn Ala Thr Leu Trp Ala Phe Leu
65                  70                  75                  80

Gln Trp Arg Arg Gly Leu Trp Ala Gln Arg Pro His Asp Ser Ala Gln
                85                  90                  95

Leu Leu Thr Gly Arg Ala Phe Gln Gly Ala Thr Val Gly Leu Ala Pro
            100                 105                 110

Val Glu Gly Met Cys Arg Ala Glu Ser Ser Gly Gly Val Ser Thr Asp
        115                 120                 125

His Ser Glu Leu Pro Ile Gly Ala Ala Ala Thr Met Ala His Glu Ile
    130                 135                 140

Gly His Ser Leu Gly Leu Ser His Asp Pro Asp Gly Cys Cys Val Glu
145                 150                 155                 160
```

Ala Ala Ala Glu Ser Gly Gly Cys Val Met Ala Ala Thr Gly His
            165                 170                 175

Pro Phe Pro Arg Val Phe Ser Ala Cys Ser Arg Gln Leu Arg Ala
            180                 185                 190

Phe Phe Arg Lys Gly Gly Ala Cys Leu Ser Asn Ala Pro
            195                 200             205

<210> SEQ ID NO 9
<211> LENGTH: 618
<212> TYPE: DNA
<213> ORGANISM: homo sapiens
<220> FEATURE:
<221> NAME/KEY: misc_feature
<222> LOCATION: (217)..(219)
<223> OTHER INFORMATION: nnn is any codon that does not encode
      asparagine.

<400> SEQUENCE: 9
gaagcgcgca ggacccggaa gtacctggaa ctgtacattg tggcagacca cacccgttc      60 ttgactcggc accgaaactt gaaccacacc aaacagcgtc tcctggaagt cgccaactac    120
gtggaccagc ttctcaggac tctggacatt caggtggcgc tgaccggcct ggaggtgtgg    180
accgagcggg accgcagccg cgtcacgcag gacgccnnng ccacgctctg ggccttcctg    240
cagtggcgcc gggggctgtg ggcgcagcgg ccccacgact ccgcgcagct gctcacgggc    300
cgcgccttcc agggcgccac agtgggcctg gcgcccgtcg agggcatgtg ccgcgccgag    360
agctcgggag gcgtgagcac ggaccactcg gagctcccca tcggcgccgc agccaccatg    420
gcccatgaga tcggccacag cctcggcctc agccacgacc ccgacggctg ctgcgtggag    480
gctgcggccg agtccggagg ctgcgtcatg gctgcggcca ccgggcaccc gtttccgcgc    540
gtgttcagcg cctgcagccg ccgccagctg cgcgccttct ccgcaagggg gggcggcgct    600
tgcctctcca atgccccg                                                  618

<210> SEQ ID NO 10
<211> LENGTH: 206
<212> TYPE: PRT
<213> ORGANISM: homo sapiens
<220> FEATURE:
<221> NAME/KEY: misc_feature
<222> LOCATION: (73)..(73)
<223> OTHER INFORMATION: Xaa can be any amino acid except asparagine.

<400> SEQUENCE: 10

Glu Ala Arg Arg Thr Arg Lys Tyr Leu Glu Leu Tyr Ile Val Ala Asp
1               5                   10                  15

His Thr Leu Phe Leu Thr Arg His Arg Asn Leu Asn His Thr Lys Gln
            20                  25                  30

Arg Leu Leu Glu Val Ala Asn Tyr Val Asp Gln Leu Leu Arg Thr Leu
        35                  40                  45

Asp Ile Gln Val Ala Leu Thr Gly Leu Glu Val Trp Thr Glu Arg Asp
    50                  55                  60

Arg Ser Arg Val Thr Gln Asp Ala Xaa Ala Thr Leu Trp Ala Phe Leu
65                  70                  75                  80

Gln Trp Arg Arg Gly Leu Trp Ala Gln Arg Pro His Asp Ser Ala Gln
                85                  90                  95

Leu Leu Thr Gly Arg Ala Phe Gln Gly Ala Thr Val Gly Leu Ala Pro
            100                 105                 110

Val Glu Gly Met Cys Arg Ala Glu Ser Ser Gly Gly Val Ser Thr Asp
            115                 120                 125

```
His Ser Glu Leu Pro Ile Gly Ala Ala Ala Thr Met Ala His Glu Ile
        130                 135                 140
Gly His Ser Leu Gly Leu Ser His Asp Pro Asp Gly Cys Cys Val Glu
145                 150                 155                 160
Ala Ala Ala Glu Ser Gly Gly Cys Val Met Ala Ala Thr Gly His
                165                 170                 175
Pro Phe Pro Arg Val Phe Ser Ala Cys Ser Arg Arg Gln Leu Arg Ala
                180                 185                 190
Phe Phe Arg Lys Gly Gly Ala Cys Leu Ser Asn Ala Pro
            195                 200                 205

<210> SEQ ID NO 11
<211> LENGTH: 618
<212> TYPE: DNA
<213> ORGANISM: homo sapiens
<220> FEATURE:
<221> NAME/KEY: misc_feature
<222> LOCATION: (219)..(219)
<223> OTHER INFORMATION: n can be either a or g.

<400> SEQUENCE: 11
gaagcgcgca ggacccggaa gtacctggaa ctgtacattg tggcagacca caccctgttc      60
ttgactcggc accgaaactt gaaccacacc aaacagcgtc tcctggaagt cgccaactac    120
gtggaccagc ttctcaggac tctggacatt caggtggcgc tgaccggcct ggaggtgtgg    180
accgagcggg accgcagccg cgtcacgcag acgcccang ccacgctctg ggccttcctg    240
cagtggcgcc gggggctgtg ggcgcagcgg ccccacgact ccgcgcagct gctcacgggc    300
cgcgccttcc agggcgccac agtgggcctg gcgcccgtcg agggcatgtg ccgcgccgag    360
agctcgggag gcgtgagcac ggaccactcg gagctcccca tcggcgccgc agccaccatg    420
gcccatgaga tcggccacag cctcggcctc agccacgacc ccgacggctg ctgcgtggag    480
gctgcggccg agtccggagg ctgcgtcatg gctgcggcca ccgggcaccc gtttccgcgc    540
gtgttcagcg cctgcagccg ccgccagctg cgcgccttct ccgcaagggg gggcggcgct    600
tgcctctcca atgccccg                                                  618

<210> SEQ ID NO 12
<211> LENGTH: 206
<212> TYPE: PRT
<213> ORGANISM: homo sapiens

<400> SEQUENCE: 12

Glu Ala Arg Arg Thr Arg Lys Tyr Leu Glu Leu Tyr Ile Val Ala Asp
1               5                   10                  15
His Thr Leu Phe Leu Thr Arg His Arg Asn Leu Asn His Thr Lys Gln
                20                  25                  30
Arg Leu Leu Glu Val Ala Asn Tyr Val Asp Gln Leu Leu Arg Thr Leu
            35                  40                  45
Asp Ile Gln Val Ala Leu Thr Gly Leu Glu Val Trp Thr Glu Arg Asp
        50                  55                  60
Arg Ser Arg Val Thr Gln Asp Ala Gln Ala Thr Leu Trp Ala Phe Leu
65                  70                  75                  80
Gln Trp Arg Arg Gly Leu Trp Ala Gln Arg Pro His Asp Ser Ala Gln
                85                  90                  95
Leu Leu Thr Gly Arg Ala Phe Gln Gly Ala Thr Val Gly Leu Ala Pro
            100                 105                 110
```

```
Val Glu Gly Met Cys Arg Ala Glu Ser Ser Gly Gly Val Ser Thr Asp
        115                 120                 125

His Ser Glu Leu Pro Ile Gly Ala Ala Ala Thr Met Ala His Glu Ile
    130                 135                 140

Gly His Ser Leu Gly Leu Ser His Asp Pro Asp Gly Cys Cys Val Glu
145                 150                 155                 160

Ala Ala Ala Glu Ser Gly Gly Cys Val Met Ala Ala Thr Gly His
                165                 170                 175

Pro Phe Pro Arg Val Phe Ser Ala Cys Ser Arg Arg Gln Leu Arg Ala
                180                 185                 190

Phe Phe Arg Lys Gly Gly Gly Ala Cys Leu Ser Asn Ala Pro
                195                 200                 205
```

<210> SEQ ID NO 13
<211> LENGTH: 618
<212> TYPE: DNA
<213> ORGANISM: homo sapiens
<220> FEATURE:
<221> NAME/KEY: misc_feature
<222> LOCATION: (82)..(84)
<223> OTHER INFORMATION: nnn can be any codon that does not encode
      asparagine.
<220> FEATURE:
<221> NAME/KEY: misc_feature
<222> LOCATION: (217)..(219)
<223> OTHER INFORMATION: nnn can be any codon that does not encode
      asparagine.

<400> SEQUENCE: 13

```
gaagcgcgca ggacccggaa gtacctggaa ctgtacattg tggcagacca caccctgttc      60
ttgactcggc accgaaactt gnnncacacc aaacagcgtc tcctggaagt cgccaactac     120
gtggaccagc ttctcaggac tctggacatt caggtggcgc tgaccggcct ggaggtgtgg     180
accgagcggg accgcagccg cgtcacgcag gacgccnnng ccacgctctg ggccttcctg     240
cagtggcgcc gggggctgtg ggcgcagcgg ccccacgact ccgcgcagct gctcacgggc     300
cgcgccttcc agggcgccac agtgggcctg gcgcccgtcg agggcatgtg ccgcgccgag     360
agctcgggag gcgtgagcac ggaccactcg gagctcccca tcggcgccgc agccaccatg     420
gcccatgaga tcggccacag cctcggcctc agccacgacc ccgacggctg ctgcgtggag     480
gctgcggccg agtccggagg ctgcgtcatg gctgcggcca ccgggcaccc gtttccgcgc     540
gtgttcagcg cctgcagccg ccgccagctg cgcgccttct ccgcaaggg gggcggcgct     600
tgcctctcca atgccccg                                                  618
```

<210> SEQ ID NO 14
<211> LENGTH: 206
<212> TYPE: PRT
<213> ORGANISM: homo sapiens
<220> FEATURE:
<221> NAME/KEY: misc_feature
<222> LOCATION: (28)..(28)
<223> OTHER INFORMATION: Xaa can be any amino acid except asparagine.
<220> FEATURE:
<221> NAME/KEY: misc_feature
<222> LOCATION: (73)..(73)
<223> OTHER INFORMATION: Xaa can be any amino acid except asparagine.

<400> SEQUENCE: 14

```
Glu Ala Arg Arg Thr Arg Lys Tyr Leu Glu Leu Tyr Ile Val Ala Asp
1               5                   10                  15

His Thr Leu Phe Leu Thr Arg His Arg Asn Leu Xaa His Thr Lys Gln
                20                  25                  30
```

-continued

```
Arg Leu Leu Glu Val Ala Asn Tyr Val Asp Gln Leu Leu Arg Thr Leu
             35                  40                  45
Asp Ile Gln Val Ala Leu Thr Gly Leu Glu Val Trp Thr Glu Arg Asp
 50                  55                  60
Arg Ser Arg Val Thr Gln Asp Ala Xaa Ala Thr Leu Trp Ala Phe Leu
 65                  70                  75                  80
Gln Trp Arg Arg Gly Leu Trp Ala Gln Arg Pro His Asp Ser Ala Gln
                 85                  90                  95
Leu Leu Thr Gly Arg Ala Phe Gln Gly Ala Thr Val Gly Leu Ala Pro
            100                 105                 110
Val Glu Gly Met Cys Arg Ala Glu Ser Ser Gly Gly Val Ser Thr Asp
        115                 120                 125
His Ser Glu Leu Pro Ile Gly Ala Ala Thr Met Ala His Glu Ile
    130                 135                 140
Gly His Ser Leu Gly Leu Ser His Asp Pro Asp Gly Cys Cys Val Glu
145                 150                 155                 160
Ala Ala Ala Glu Ser Gly Gly Cys Val Met Ala Ala Thr Gly His
                165                 170                 175
Pro Phe Pro Arg Val Phe Ser Ala Cys Ser Arg Arg Gln Leu Arg Ala
            180                 185                 190
Phe Phe Arg Lys Gly Gly Gly Ala Cys Leu Ser Asn Ala Pro
        195                 200                 205
```

<210> SEQ ID NO 15
<211> LENGTH: 618
<212> TYPE: DNA
<213> ORGANISM: homo sapiens
<220> FEATURE:
<221> NAME/KEY: misc_feature
<222> LOCATION: (84)..(84)
<223> OTHER INFORMATION: n is a or g
<220> FEATURE:
<221> NAME/KEY: misc_feature
<222> LOCATION: (219)..(219)
<223> OTHER INFORMATION: n is a or g

<400> SEQUENCE: 15

```
gaagcgcgca ggacccggaa gtacctggaa ctgtacattg tggcagacca cacccctgttc     60
ttgactcggc accgaaactt gcancacacc aaacagcgtc tcctggaagt cgccaactac    120
gtggaccagc ttctcaggac tctggacatt caggtggcgc tgaccggcct ggaggtgtgg    180
accgagcggg accgcagccg cgtcacgcag gacgcccang ccacgctctg ggccttcctg    240
cagtggcgcc gggggctgtg gcgcagcgg ccccacgact ccgcgcagct gctcacgggc    300
cgcgccttcc agggcgccac agtgggcctg gcgcccgtcg agggcatgtg ccgcgccgag    360
agctcgggag gcgtgagcac ggaccactcg agctccccca tcggcgccgc agccaccatg    420
gcccatgaga tcggccacag cctcggcctc agccacgacc ccgacggctg ctgcgtggag    480
gctgcggccg agtccggagg ctgcgtcatg gctgcggcca ccgggcaccc gtttccgcgc    540
gtgttcagcg cctgcagccg ccgccagctg cgcgccttct ccgcaaggg gggcggcgct    600
tgcctctcca atgccccg                                                  618
```

<210> SEQ ID NO 16
<211> LENGTH: 206
<212> TYPE: PRT
<213> ORGANISM: homo sapiens

<400> SEQUENCE: 16

```
Glu Ala Arg Arg Thr Arg Lys Tyr Leu Glu Leu Tyr Ile Val Ala Asp
1               5                   10                  15

His Thr Leu Phe Leu Thr Arg His Arg Asn Leu Gln His Thr Lys Gln
            20                  25                  30

Arg Leu Leu Glu Val Ala Asn Tyr Val Asp Gln Leu Leu Arg Thr Leu
        35                  40                  45

Asp Ile Gln Val Ala Leu Thr Gly Leu Glu Val Trp Thr Glu Arg Asp
50                  55                  60

Arg Ser Arg Val Thr Gln Asp Ala Gln Ala Thr Leu Trp Ala Phe Leu
65                  70                  75                  80

Gln Trp Arg Arg Gly Leu Trp Ala Gln Arg Pro His Asp Ser Ala Gln
                85                  90                  95

Leu Leu Thr Gly Arg Ala Phe Gln Gly Ala Thr Val Gly Leu Ala Pro
            100                 105                 110

Val Glu Gly Met Cys Arg Ala Glu Ser Ser Gly Val Ser Thr Asp
        115                 120                 125

His Ser Glu Leu Pro Ile Gly Ala Ala Thr Met Ala His Glu Ile
130                 135                 140

Gly His Ser Leu Gly Leu Ser His Asp Pro Asp Gly Cys Cys Val Glu
145                 150                 155                 160

Ala Ala Ala Glu Ser Gly Gly Cys Val Met Ala Ala Thr Gly His
                165                 170                 175

Pro Phe Pro Arg Val Phe Ser Ala Cys Ser Arg Arg Gln Leu Arg Ala
            180                 185                 190

Phe Phe Arg Lys Gly Gly Gly Ala Cys Leu Ser Asn Ala Pro
            195                 200                 205

<210> SEQ ID NO 17
<211> LENGTH: 38
<212> TYPE: DNA
<213> ORGANISM: Artificial sequence
<220> FEATURE:
<223> OTHER INFORMATION: primer

<400> SEQUENCE: 17
ctcggcaccg aaacttgcag cacaccaaac agcgtctc                              38

<210> SEQ ID NO 18
<211> LENGTH: 38
<212> TYPE: DNA
<213> ORGANISM: Artificial sequence
<220> FEATURE:
<223> OTHER INFORMATION: primer

<400> SEQUENCE: 18
gagacgctgt ttggtgtgct gcaagtttcg gtgccgag                              38

<210> SEQ ID NO 19
<211> LENGTH: 33
<212> TYPE: DNA
<213> ORGANISM: Artificial sequence
<220> FEATURE:
<223> OTHER INFORMATION: primer

<400> SEQUENCE: 19
gtcacgcagg acgcccaggc cacgctctgg gcc                                   33

<210> SEQ ID NO 20
<211> LENGTH: 33
```

-continued

```
<212> TYPE: DNA
<213> ORGANISM: Artificial sequence
<220> FEATURE:
<223> OTHER INFORMATION: primer

<400> SEQUENCE: 20
ggcccagagc gtggcctggg cgtcctgcgt gac                                    33

<210> SEQ ID NO 21
<211> LENGTH: 30
<212> TYPE: PRT
<213> ORGANISM: homo sapiens

<400> SEQUENCE: 21

Met Gly Trp Arg Pro Arg Arg Ala Arg Gly Thr Pro Leu Leu Leu Leu
1               5                  10                  15

Leu Leu Leu Leu Leu Trp Pro Val Pro Gly Ala Gly Val
            20                  25                  30

<210> SEQ ID NO 22
<211> LENGTH: 18
<212> TYPE: PRT
<213> ORGANISM: Drosophila melanogaster

<400> SEQUENCE: 22

Met Lys Leu Cys Ile Leu Leu Ala Val Val Ala Phe Val Gly Leu Ser
1               5                  10                  15

Leu Gly

<210> SEQ ID NO 23
<211> LENGTH: 22
<212> TYPE: PRT
<213> ORGANISM: Drosophila melanogaster

<400> SEQUENCE: 23

Met Lys Leu Thr Lys Leu Trp Leu Leu Phe Val Cys Leu Gly Leu Phe
1               5                  10                  15

Val Thr Leu Val Val Ser
            20

<210> SEQ ID NO 24
<211> LENGTH: 21
<212> TYPE: PRT
<213> ORGANISM: Apis mellifera

<400> SEQUENCE: 24

Met Lys Phe Leu Val Asn Val Asn Leu Val Phe Met Val Val Tyr Ile
1               5                  10                  15

Ser Tyr Ile Tyr Ala
            20

<210> SEQ ID NO 25
<211> LENGTH: 16
<212> TYPE: PRT
<213> ORGANISM: Tenebrio molitor

<400> SEQUENCE: 25

Met Tyr Lys Phe Val Val Phe Ala Ala Ala Leu Ala Tyr Ala Asn Ala
1               5                  10                  15

<210> SEQ ID NO 26
<211> LENGTH: 18
<212> TYPE: PRT
```

<213> ORGANISM: Aedes aegypti

<400> SEQUENCE: 26

Met Ala Met Leu Leu Gln Val Ala Leu Pro Leu Ala Ala Val Ser
1               5                   10                  15

Trp Gly

<210> SEQ ID NO 27
<211> LENGTH: 18
<212> TYPE: PRT
<213> ORGANISM: Autographa californica nucleopolyhedrovirus

<400> SEQUENCE: 27

Met Thr Ile Leu Cys Trp Leu Ala Leu Leu Ser Thr Leu Thr Ala Val
1               5                   10                  15

Asn Ala

<210> SEQ ID NO 28
<211> LENGTH: 24
<212> TYPE: PRT
<213> ORGANISM: Autographa californica nucleopolyhedrovirus

<400> SEQUENCE: 28

Met Val Ser Ala Ile Val Leu Tyr Val Leu Leu Ala Ala Ala Ala His
1               5                   10                  15

Ser Ala Phe Ala Ala Glu His Cys
            20

<210> SEQ ID NO 29
<211> LENGTH: 1137
<212> TYPE: DNA
<213> ORGANISM: homo sapiens

<400> SEQUENCE: 29
cttcaaggac atatccctgg gcagccagtc accccgcact gggtcctgga tggacaaccc      60
tggcgcaccg tcagcctgga ggagccggtc tcgaagccag acatgggct ggtggccctg      120
gaggctgaag gccaggagct cctgcttgag ctggagaaga ccacaggct gctggcccca      180
ggatacatag aaaccactaa cggcccagat gggcagccag tggtgctggc ccccaaccac      240
acggatcatt gccactacca agggcgagta aggggtttcc ccgactcctg ggtagtcctc      300
tgcacctgct ctgggatgag tggcctgatc accctcagca ggaatgccag ctattatctg      360
cgtccctggc caccccgggg ctccaaggac ttctcaaccc acgagatctt tcggatggag      420
cagctgctca cctggaaagg aacctgtggc acagggatc ctgggaacaa agcgggcatg      480
accagtcttc ctggtggtcc ccagagcagg ggcaggcgag aagcgcgcag acccggaag      540
tacctggaac tgtacattgt ggcagaccac accctgttct tgactcggca ccgaaacttg      600
aaccacacca aacagcgtct cctggaagtc gccaactacg tggaccagct tctcaggact      660
ctggacattc aggtggcgct gaccggcctg gaggtgtgga ccgagcggga ccgcagccgc      720
gtcacgcagg acgccaacgc cacgctctgg gccttcctgc agtggcgccg ggggctgtgg      780
gcgcagcggc cccacgactc cgcgcagctg ctcacgggcc gcgccttcca gggcgccaca      840
gtgggcctgg cgcccgtcga gggcatgtgc gcgccgaga ctcgggagg cgtgagcacg      900
gaccactcgg agctccccat cggcgccgca gccaccatgg cccatgagat cggccacagc      960
ctcggcctca gccacgaccc cgacggctgc gtgtggagg ctgcggccga gtccggaggc     1020
tgcgtcatgg ctgcggccac cgggcacccg tttccgcgcg tgttcagcgc ctgcagccgc     1080
cgccagctgc gcgccttctt ccgcaagggg ggcggcgctt gcctctccaa tgccccg    1137

<210> SEQ ID NO 30
<211> LENGTH: 379
<212> TYPE: PRT
<213> ORGANISM: homo sapiens

<400> SEQUENCE: 30

Leu Gln Gly His Ile Pro Gly Gln Pro Val Thr Pro His Trp Val Leu
1               5                   10                  15

Asp Gly Gln Pro Trp Arg Thr Val Ser Leu Glu Glu Pro Val Ser Lys
            20                  25                  30

Pro Asp Met Gly Leu Val Ala Leu Glu Ala Glu Gly Gln Glu Leu Leu
        35                  40                  45

Leu Glu Leu Glu Lys Asn His Arg Leu Leu Ala Pro Gly Tyr Ile Glu
    50                  55                  60

Thr His Tyr Gly Pro Asp Gly Gln Pro Val Val Leu Ala Pro Asn His
65                  70                  75                  80

Thr Asp His Cys His Tyr Gln Gly Arg Val Arg Gly Phe Pro Asp Ser
                85                  90                  95

Trp Val Val Leu Cys Thr Cys Ser Gly Met Ser Gly Leu Ile Thr Leu
            100                 105                 110

Ser Arg Asn Ala Ser Tyr Tyr Leu Arg Pro Trp Pro Pro Arg Gly Ser
        115                 120                 125

Lys Asp Phe Ser Thr His Glu Ile Phe Arg Met Glu Gln Leu Leu Thr
130                 135                 140

Trp Lys Gly Thr Cys Gly His Arg Asp Pro Gly Asn Lys Ala Gly Met
145                 150                 155                 160

Thr Ser Leu Pro Gly Gly Pro Gln Ser Arg Gly Arg Glu Ala Arg
                165                 170                 175

Arg Thr Arg Lys Tyr Leu Glu Leu Tyr Ile Val Ala Asp His Thr Leu
            180                 185                 190

Phe Leu Thr Arg His Arg Asn Leu Asn His Thr Lys Gln Arg Leu Leu
        195                 200                 205

Glu Val Ala Asn Tyr Val Asp Gln Leu Leu Arg Thr Leu Asp Ile Gln
    210                 215                 220

Val Ala Leu Thr Gly Leu Glu Val Trp Thr Glu Arg Asp Arg Ser Arg
225                 230                 235                 240

Val Thr Gln Asp Ala Asn Ala Thr Leu Trp Ala Phe Leu Gln Trp Arg
                245                 250                 255

Arg Gly Leu Trp Ala Gln Arg Pro His Asp Ser Ala Gln Leu Leu Thr
            260                 265                 270

Gly Arg Ala Phe Gln Gly Ala Thr Val Gly Leu Ala Pro Val Glu Gly
        275                 280                 285

Met Cys Arg Ala Glu Ser Ser Gly Gly Val Ser Thr Asp His Ser Glu
    290                 295                 300

Leu Pro Ile Gly Ala Ala Thr Met Ala His Glu Ile Gly His Ser
305                 310                 315                 320

Leu Gly Leu Ser His Asp Pro Asp Gly Cys Cys Val Glu Ala Ala Ala
                325                 330                 335

Glu Ser Gly Gly Cys Val Met Ala Ala Ala Thr Gly His Pro Phe Pro
            340                 345                 350

Arg Val Phe Ser Ala Cys Ser Arg Arg Gln Leu Arg Ala Phe Phe Arg
        355                 360                 365

```
Lys Gly Gly Gly Ala Cys Leu Ser Asn Ala Pro
    370                 375
```

<210> SEQ ID NO 31
<211> LENGTH: 1137
<212> TYPE: DNA
<213> ORGANISM: homo sapiens
<220> FEATURE:
<221> NAME/KEY: misc_feature
<222> LOCATION: (601)..(603)
<223> OTHER INFORMATION: nnn can be any codon that encodes any amino
      acid except asparagine.
<220> FEATURE:
<221> NAME/KEY: misc_feature
<222> LOCATION: (736)..(738)
<223> OTHER INFORMATION: nnn can be any codon that encodes any amino
      acid except asparagine.

<400> SEQUENCE: 31

```
cttcaaggac atatccctgg gcagccagtc accccgcact gggtcctgga tggacaaccc      60
tggcgcaccg tcagcctgga ggagccggtc tcgaagccag acatggggct ggtggccctg     120
gaggctgaag gccaggagct cctgcttgag ctggagaaga ccacaggct gctggccccca     180
ggatacatag aaacccacta cggcccagat gggcagccag tggtgctggc ccccaaccac     240
acggatcatt gccactacca agggcgagta aggggtttcc ccgactcctg ggtagtcctc     300
tgcacctgct ctgggatgag tggcctgatc accctcagca ggaatgccag ctattatctg     360
cgtccctggc caccccgggg ctccaaggac ttctcaaccc acgagatctt tcggatggag     420
cagctgctca cctggaaagg aacctgtggc cacagggatc ctgggaacaa agcgggcatg     480
accagtcttc ctggtggtcc ccagagcagg ggcaggcgag aagcgcgcag acccggaag      540
tacctggaac tgtacattgt ggcagaccac accctgttct tgactcggca ccgaaacttg     600
nnncacacca acagcgtctc cctggaagtc gccaactacg tggaccagct tctcaggact     660
ctggacattc aggtggcgct gaccggcctg gaggtgtgga ccgagcggga ccgcagccgc     720
gtcacgcagg acgccnnngc cacgctctgg gccttcctgc agtggcgccg ggggctgtgg     780
gcgcagcggc cccacgactc cgcgcagctg ctcacgggcc gcgccttcca gggcgccaca     840
gtgggcctgg cgcccgtcga gggcatgtgc cgcgccgaga gctcgggagg cgtgagcacg     900
gaccactcgg agctccccat cggcgccgca gccaccatgg cccatgagat cggccacagc     960
ctcggcctca gccacgaccc cgacggctgc tgcgtggagg ctgcggccga gtccggaggc    1020
tgcgtcatgg ctgcggccac cgggcacccg tttccgcgcg tgttcagcgc ctgcagccgc    1080
cgccagctgc gcgccttctt ccgcaagggg ggcggcgctt gcctctccaa tgccccg       1137
```

<210> SEQ ID NO 32
<211> LENGTH: 379
<212> TYPE: PRT
<213> ORGANISM: homo sapiens
<220> FEATURE:
<221> NAME/KEY: misc_feature
<222> LOCATION: (201)..(201)
<223> OTHER INFORMATION: Xaa can be any amino acid except asparagine.
<220> FEATURE:
<221> NAME/KEY: misc_feature
<222> LOCATION: (246)..(246)
<223> OTHER INFORMATION: Xaa can be any amino acid except asparagine.

<400> SEQUENCE: 32

```
Leu Gln Gly His Ile Pro Gly Gln Pro Val Thr Pro His Trp Val Leu
1               5                   10                  15
```

```
Asp Gly Gln Pro Trp Arg Thr Val Ser Leu Glu Glu Pro Val Ser Lys
            20                  25                  30
Pro Asp Met Gly Leu Val Ala Leu Glu Ala Glu Gly Gln Glu Leu Leu
        35                  40                  45
Leu Glu Leu Glu Lys Asn His Arg Leu Leu Ala Pro Gly Tyr Ile Glu
    50                  55                  60
Thr His Tyr Gly Pro Asp Gly Gln Pro Val Val Leu Ala Pro Asn His
65                  70                  75                  80
Thr Asp His Cys His Tyr Gln Gly Arg Val Arg Gly Phe Pro Asp Ser
                85                  90                  95
Trp Val Val Leu Cys Thr Cys Ser Gly Met Ser Gly Leu Ile Thr Leu
            100                 105                 110
Ser Arg Asn Ala Ser Tyr Tyr Leu Arg Pro Trp Pro Arg Gly Ser
        115                 120                 125
Lys Asp Phe Ser Thr His Glu Ile Phe Arg Met Glu Gln Leu Leu Thr
    130                 135                 140
Trp Lys Gly Thr Cys Gly His Arg Asp Pro Gly Asn Lys Ala Gly Met
145                 150                 155                 160
Thr Ser Leu Pro Gly Gly Pro Gln Ser Arg Gly Arg Glu Ala Arg
                165                 170                 175
Arg Thr Arg Lys Tyr Leu Glu Leu Tyr Ile Val Ala Asp His Thr Leu
            180                 185                 190
Phe Leu Thr Arg His Arg Asn Leu Xaa His Thr Lys Gln Arg Leu Leu
        195                 200                 205
Glu Val Ala Asn Tyr Val Asp Gln Leu Leu Arg Thr Leu Asp Ile Gln
    210                 215                 220
Val Ala Leu Thr Gly Leu Glu Val Trp Thr Glu Arg Asp Arg Ser Arg
225                 230                 235                 240
Val Thr Gln Asp Ala Xaa Ala Thr Leu Trp Ala Phe Leu Gln Trp Arg
                245                 250                 255
Arg Gly Leu Trp Ala Gln Arg Pro His Asp Ser Ala Gln Leu Leu Thr
            260                 265                 270
Gly Arg Ala Phe Gln Gly Ala Thr Val Gly Leu Ala Pro Val Glu Gly
        275                 280                 285
Met Cys Arg Ala Glu Ser Ser Gly Gly Val Ser Thr Asp His Ser Glu
    290                 295                 300
Leu Pro Ile Gly Ala Ala Ala Thr Met Ala His Glu Ile Gly His Ser
305                 310                 315                 320
Leu Gly Leu Ser His Asp Pro Asp Gly Cys Cys Val Glu Ala Ala Ala
                325                 330                 335
Glu Ser Gly Gly Cys Val Met Ala Ala Ala Thr Gly His Pro Phe Pro
            340                 345                 350
Arg Val Phe Ser Ala Cys Ser Arg Arg Gln Leu Arg Ala Phe Phe Arg
        355                 360                 365
Lys Gly Gly Gly Ala Cys Leu Ser Asn Ala Pro
    370                 375
```

<210> SEQ ID NO 33
<211> LENGTH: 1137
<212> TYPE: DNA
<213> ORGANISM: homo sapiens
<220> FEATURE:
<221> NAME/KEY: misc_feature
<222> LOCATION: (601)..(603)
<223> OTHER INFORMATION: nnn can encode any amino acid except
    asparagine.

<400> SEQUENCE: 33

```
cttcaaggac atatccctgg gcagccagtc accccgcact gggtcctgga tggacaaccc      60
tggcgcaccg tcagcctgga ggagccggtc tcgaagccag acatggggct ggtggccctg     120
gaggctgaag gccaggagct cctgcttgag ctggagaaga accacaggct gctggcccca     180
ggatacatag aaacccacta cggcccagat gggcagccag tggtgctggc ccccaaccac     240
acggatcatt gccactacca agggcgagta aggggtttcc ccgactcctg ggtagtcctc     300
tgcacctgct ctgggatgag tggcctgatc accctcagca ggaatgccag ctattatctg     360
cgtccctggc caccccgggg ctccaaggac ttctcaaccc acgagatctt tcggatggag     420
cagctgctca cctggaaagg aacctgtggc cacagggatc ctgggaacaa gcgggcatg      480
accagtcttc ctggtggtcc ccagagcagg ggcaggcgag aagcgcgcag acccggaag     540
tacctggaac tgtacattgt ggcagaccac accctgttct tgactcggca ccgaaacttg     600
nnncacacca aacagcgtct cctggaagtc gccaactacg tggaccagct tctcaggact     660
ctggacattc aggtggcgct gaccggcctg gaggtgtgga ccgagcggga ccgcagccgc     720
gtcacgcagg acgccaacgc cacgctctgg gccttcctgc agtggcgccg ggggctgtgg     780
gcgcagcggc cccacgactc cgcgcagctg ctcacgggcc cgccttcca gggcgccaca      840
gtgggcctgg cgcccgtcga gggcatgtgc cgcgccgaga gctcgggagg cgtgagcacg     900
gaccactcgg agctccccat cggcgccgca gccaccatgg cccatgagat cggccacagc     960
ctcggcctca gccacgaccc cgacggctgc tgcgtggagc tgcggccga gtccggaggc    1020
tgcgtcatgg ctgcggccac cgggcacccg tttccgcgcg tgttcagcgc ctgcagccgc    1080
cgccagctgc cgccttctt ccgcaagggg ggcggcgctt gcctctccaa tgccccg      1137
```

<210> SEQ ID NO 34
<211> LENGTH: 379
<212> TYPE: PRT
<213> ORGANISM: homo sapiens
<220> FEATURE:
<221> NAME/KEY: misc_feature
<222> LOCATION: (201)..(201)
<223> OTHER INFORMATION: Xaa can be any amino acid except asparagine.

<400> SEQUENCE: 34

```
Leu Gln Gly His Ile Pro Gly Gln Pro Val Thr Pro His Trp Val Leu
1               5                   10                  15

Asp Gly Gln Pro Trp Arg Thr Val Ser Leu Glu Glu Pro Val Ser Lys
            20                  25                  30

Pro Asp Met Gly Leu Val Ala Leu Glu Ala Glu Gly Gln Glu Leu Leu
        35                  40                  45

Leu Glu Leu Glu Lys Asn His Arg Leu Leu Ala Pro Gly Tyr Ile Glu
    50                  55                  60

Thr His Tyr Gly Pro Asp Gly Gln Pro Val Val Leu Ala Pro Asn His
65                  70                  75                  80

Thr Asp His Cys His Tyr Gln Gly Arg Val Arg Gly Phe Pro Asp Ser
                85                  90                  95

Trp Val Val Leu Cys Thr Cys Ser Gly Met Ser Gly Leu Ile Thr Leu
            100                 105                 110

Ser Arg Asn Ala Ser Tyr Tyr Leu Arg Pro Trp Pro Pro Arg Gly Ser
        115                 120                 125

Lys Asp Phe Ser Thr His Glu Ile Phe Arg Met Glu Gln Leu Leu Thr
    130                 135                 140
```

```
Trp Lys Gly Thr Cys Gly His Arg Asp Pro Gly Asn Lys Ala Gly Met
145                 150                 155                 160

Thr Ser Leu Pro Gly Gly Pro Gln Ser Arg Gly Arg Arg Glu Ala Arg
            165                 170                 175

Arg Thr Arg Lys Tyr Leu Glu Leu Tyr Ile Val Ala Asp His Thr Leu
        180                 185                 190

Phe Leu Thr Arg His Arg Asn Leu Xaa His Thr Lys Gln Arg Leu Leu
    195                 200                 205

Glu Val Ala Asn Tyr Val Asp Gln Leu Leu Arg Thr Leu Asp Ile Gln
210                 215                 220

Val Ala Leu Thr Gly Leu Glu Val Trp Thr Glu Arg Asp Arg Ser Arg
225                 230                 235                 240

Val Thr Gln Asp Ala Asn Ala Thr Leu Trp Ala Phe Leu Gln Trp Arg
                245                 250                 255

Arg Gly Leu Trp Ala Gln Arg Pro His Asp Ser Ala Gln Leu Leu Thr
            260                 265                 270

Gly Arg Ala Phe Gln Gly Ala Thr Val Gly Leu Ala Pro Val Glu Gly
        275                 280                 285

Met Cys Arg Ala Glu Ser Ser Gly Val Ser Thr Asp His Ser Glu
    290                 295                 300

Leu Pro Ile Gly Ala Ala Ala Thr Met Ala His Glu Ile Gly His Ser
305                 310                 315                 320

Leu Gly Leu Ser His Asp Pro Asp Gly Cys Cys Val Glu Ala Ala Ala
                325                 330                 335

Glu Ser Gly Gly Cys Val Met Ala Ala Ala Thr Gly His Pro Phe Pro
            340                 345                 350

Arg Val Phe Ser Ala Cys Ser Arg Arg Gln Leu Arg Ala Phe Phe Arg
        355                 360                 365

Lys Gly Gly Gly Ala Cys Leu Ser Asn Ala Pro
    370                 375

<210> SEQ ID NO 35
<211> LENGTH: 10
<212> TYPE: PRT
<213> ORGANISM: Artificial sequence
<220> FEATURE:
<223> OTHER INFORMATION: synthetic peptide

<400> SEQUENCE: 35

Tyr Glu Val His His Gln Lys Leu Val Phe
1               5                   10

<210> SEQ ID NO 36
<211> LENGTH: 8
<212> TYPE: PRT
<213> ORGANISM: artificial sequence
<220> FEATURE:
<223> OTHER INFORMATION: linker plus His-Tag

<400> SEQUENCE: 36

Ser Gly His His His His His His
1               5

<210> SEQ ID NO 37
<211> LENGTH: 642
<212> TYPE: DNA
<213> ORGANISM: homo sapiens
<220> FEATURE:
<221> NAME/KEY: misc_feature
```

```
<222> LOCATION: (84)..(84)
<223> OTHER INFORMATION: n can be a or g.

<400> SEQUENCE: 37
gaagcgcgca ggacccggaa gtacctggaa ctgtacattg tggcagacca cacctgttc      60 ttgactcggc accgaaactt gcancacacc aaacagcgtc tcctggaagt cgccaactac    120
gtggaccagc ttctcaggac tctggacatt caggtggcgc tgaccggcct ggaggtgtgg    180
accgagcggg accgcagccg cgtcacgcag gacgccaacg ccacgctctg ggccttcctg    240
cagtggcgcc gggggctgtg ggcgcagcgg ccccacgact ccgcgcagct gctcacgggc    300
cgcgccttcc agggcgccac agtgggcctg gcgcccgtcg agggcatgtg ccgcgccgag    360
agctcgggag gcgtgagcac ggaccactcg gagctcccca tcggcgccgc agccaccatg    420
gcccatgaga tcggccacag cctcggcctc agccacgacc ccgacggctg ctgcgtggag    480
gctgcggccg agtccggagg ctgcgtcatg gctgcggcca ccgggcaccc gtttccgcgc    540
gtgttcagcg cctgcagccg ccgccagctg cgcgccttct tccgcaaggg gggcggcgct    600
tgcctctcca atgccccgtc aggacatcat catcaccatc at                        642

<210> SEQ ID NO 38
<211> LENGTH: 214
<212> TYPE: PRT
<213> ORGANISM: homo sapiens

<400> SEQUENCE: 38

Glu Ala Arg Arg Thr Arg Lys Tyr Leu Glu Leu Tyr Ile Val Ala Asp
1               5                   10                  15

His Thr Leu Phe Leu Thr Arg His Arg Asn Leu Gln His Thr Lys Gln
            20                  25                  30

Arg Leu Leu Glu Val Ala Asn Tyr Val Asp Gln Leu Leu Arg Thr Leu
        35                  40                  45

Asp Ile Gln Val Ala Leu Thr Gly Leu Glu Val Trp Thr Glu Arg Asp
    50                  55                  60

Arg Ser Arg Val Thr Gln Asp Ala Asn Ala Thr Leu Trp Ala Phe Leu
65                  70                  75                  80

Gln Trp Arg Arg Gly Leu Trp Ala Gln Arg Pro His Asp Ser Ala Gln
                85                  90                  95

Leu Leu Thr Gly Arg Ala Phe Gln Gly Ala Thr Val Gly Leu Ala Pro
            100                 105                 110

Val Glu Gly Met Cys Arg Ala Glu Ser Ser Gly Gly Val Ser Thr Asp
        115                 120                 125

His Ser Glu Leu Pro Ile Gly Ala Ala Ala Thr Met Ala His Glu Ile
    130                 135                 140

Gly His Ser Leu Gly Leu Ser His Asp Pro Asp Gly Cys Cys Val Glu
145                 150                 155                 160

Ala Ala Ala Glu Ser Gly Gly Cys Val Met Ala Ala Ala Thr Gly His
                165                 170                 175

Pro Phe Pro Arg Val Phe Ser Ala Cys Ser Arg Gln Leu Arg Ala
            180                 185                 190

Phe Phe Arg Lys Gly Gly Gly Ala Cys Leu Ser Asn Ala Pro Ser Gly
        195                 200                 205

His His His His His His
    210

<210> SEQ ID NO 39
```

```
<211> LENGTH: 65
<212> TYPE: DNA
<213> ORGANISM: Artificial sequence
<220> FEATURE:
<223> OTHER INFORMATION: primer

<400> SEQUENCE: 39
atctgatatc tcgagtcaat gatggtgatg atgatgtcct gacggggcat tggagaggca    60
agcgc                                                                65

<210> SEQ ID NO 40
<211> LENGTH: 43
<212> TYPE: DNA
<213> ORGANISM: Artificial sequence
<220> FEATURE:
<223> OTHER INFORMATION: primer

<400> SEQUENCE: 40
ttagattcat agggtaccgc ttcaaggaca tatccctggg cag                       43

<210> SEQ ID NO 41
<211> LENGTH: 11
<212> TYPE: PRT
<213> ORGANISM: artificial sequence
<220> FEATURE:
<223> OTHER INFORMATION: artificial substrate
<220> FEATURE:
<221> NAME/KEY: misc_feature
<222> LOCATION: (11)..(11)
<223> OTHER INFORMATION: Tyr is a phosphotyrosine.

<400> SEQUENCE: 41

Tyr Glu Val His His Gln Lys Leu Val Phe Tyr
1               5                   10

<210> SEQ ID NO 42
<211> LENGTH: 10
<212> TYPE: PRT
<213> ORGANISM: artificial sequence
<220> FEATURE:
<223> OTHER INFORMATION: KL-1 Peptide

<400> SEQUENCE: 42

Pro Pro Val Ala Ala Ser Ser Leu Arg Asn
1               5                   10

<210> SEQ ID NO 43
<211> LENGTH: 10
<212> TYPE: PRT
<213> ORGANISM: artificial sequence
<220> FEATURE:
<223> OTHER INFORMATION: APP Peptide

<400> SEQUENCE: 43

Tyr Glu Val His His Gln Lys Leu Val Phe
1               5                   10

<210> SEQ ID NO 44
<211> LENGTH: 10
<212> TYPE: PRT
<213> ORGANISM: TRANCE Peptide

<400> SEQUENCE: 44

Val Gly Ser Gln His Ile Arg Ala Glu Lys
1               5                   10
```

```
<210> SEQ ID NO 45
<211> LENGTH: 10
<212> TYPE: PRT
<213> ORGANISM: insulin B chain peptide

<400> SEQUENCE: 45

His Leu Val Glu Ala Leu Tyr Leu Val Cys
1               5                   10

<210> SEQ ID NO 46
<211> LENGTH: 14
<212> TYPE: PRT
<213> ORGANISM: artificial sequence
<220> FEATURE:
<223> OTHER INFORMATION: TNF-alpha substrate

<400> SEQUENCE: 46

Lys Ser Pro Leu Ala Gln Ala Val Arg Ser Ser Ser Arg Lys
1               5                   10

<210> SEQ ID NO 47
<211> LENGTH: 15
<212> TYPE: PRT
<213> ORGANISM: artificial sequence
<220> FEATURE:
<223> OTHER INFORMATION: fluorogenic substrate

<400> SEQUENCE: 47

Lys Leu Pro Pro Val Ala Ala Ser Ser Leu Arg Asn Asp Glu Lys
1               5                   10                  15

<210> SEQ ID NO 48
<211> LENGTH: 12
<212> TYPE: PRT
<213> ORGANISM: artificial sequence
<220> FEATURE:
<223> OTHER INFORMATION: MCF peptide

<400> SEQUENCE: 48

Leu Pro Pro Val Ala Ala Ser Ser Leu Asn Arg Asp
1               5                   10

<210> SEQ ID NO 49
<211> LENGTH: 379
<212> TYPE: PRT
<213> ORGANISM: homo sapiens

<400> SEQUENCE: 49

Leu Gln Gly His Ile Pro Gly Gln Pro Val Thr Pro His Trp Val Leu
1               5                   10                  15

Asp Gly Gln Pro Trp Arg Thr Val Ser Leu Glu Glu Pro Val Ser Lys
            20                  25                  30

Pro Asp Met Gly Leu Val Ala Leu Glu Ala Glu Gly Gln Glu Leu Leu
        35                  40                  45

Leu Glu Leu Glu Lys Asn His Arg Leu Leu Ala Pro Gly Tyr Ile Glu
    50                  55                  60

Thr His Tyr Gly Pro Asp Gly Gln Pro Val Val Leu Ala Pro Asn His
65                  70                  75                  80

Thr Asp His Cys His Tyr Gln Gly Arg Val Arg Gly Phe Pro Asp Ser
                85                  90                  95

Trp Val Val Leu Ala Thr Cys Ser Gly Met Ser Gly Leu Ile Thr Leu
            100                 105                 110

Ser Arg Asn Ala Ser Tyr Tyr Leu Arg Pro Trp Pro Pro Arg Gly Ser
```

115                 120                     125
Lys Asp Phe Ser Thr His Glu Ile Phe Arg Met Glu Gln Leu Leu Thr
        130                     135                 140

Trp Lys Gly Thr Cys Gly His Arg Asp Pro Gly Asn Lys Ala Gly Met
145                 150                     155                 160

Thr Ser Leu Pro Gly Gly Pro Gln Ser Arg Gly Arg Arg Glu Ala Arg
                165                     170                 175

Arg Thr Arg Lys Tyr Leu Glu Leu Tyr Ile Val Ala Asp His Thr Leu
                180                     185                 190

Phe Leu Thr Arg His Arg Asn Leu Asn His Thr Lys Gln Arg Leu Leu
                195                     200                 205

Glu Val Ala Asn Tyr Val Asp Gln Leu Leu Arg Thr Leu Asp Ile Gln
        210                     215                 220

Val Ala Leu Thr Gly Leu Glu Val Trp Thr Glu Arg Asp Arg Ser Arg
225                 230                     235                 240

Val Thr Gln Asp Ala Asn Ala Thr Leu Trp Ala Phe Leu Gln Trp Arg
                245                     250                 255

Arg Gly Leu Trp Ala Gln Arg Pro His Asp Ser Ala Gln Leu Leu Thr
                260                     265                 270

Gly Arg Ala Phe Gln Gly Ala Thr Val Gly Leu Ala Pro Val Glu Gly
                275                     280                 285

Met Cys Arg Ala Glu Ser Ser Gly Val Ser Thr Asp His Ser Glu
        290                     295                 300

Leu Pro Ile Gly Ala Ala Ala Thr Met Ala His Glu Ile Gly His Ser
305                 310                     315                 320

Leu Gly Leu Ser His Asp Pro Asp Gly Cys Cys Val Glu Ala Ala Ala
                325                     330                 335

Glu Ser Gly Gly Cys Val Met Ala Ala Ala Thr Gly His Pro Phe Pro
                340                     345                 350

Arg Val Phe Ser Ala Cys Ser Arg Arg Gln Leu Arg Ala Phe Phe Arg
                355                     360                 365

Lys Gly Gly Gly Ala Cys Leu Ser Asn Ala Pro
        370                     375

<210> SEQ ID NO 50
<211> LENGTH: 379
<212> TYPE: PRT
<213> ORGANISM: homo sapiens

<400> SEQUENCE: 50

Leu Gln Gly His Ile Pro Gly Gln Pro Val Thr Pro His Trp Val Leu
1               5                   10                  15

Asp Gly Gln Pro Trp Arg Thr Val Ser Leu Glu Glu Pro Val Ser Lys
                20                  25                  30

Pro Asp Met Gly Leu Val Ala Leu Glu Ala Glu Gly Gln Glu Leu Leu
        35                  40                  45

Leu Glu Leu Glu Lys Asn His Arg Leu Leu Ala Pro Gly Tyr Ile Glu
    50                  55                  60

Thr His Tyr Gly Pro Asp Gly Gln Pro Val Val Leu Ala Pro Asn His
65                  70                  75                  80

Thr Asp His Cys His Tyr Gln Gly Arg Val Arg Gly Phe Pro Asp Ser
                85                  90                  95

Trp Val Val Leu Cys Thr Cys Ser Gly Met Ser Gly Leu Ile Thr Leu
            100                 105                 110

```
Ser Arg Asn Ala Ser Tyr Tyr Leu Arg Pro Trp Pro Arg Gly Ser
        115                 120                 125

Lys Asp Phe Ser Thr His Glu Ile Phe Arg Met Glu Gln Leu Leu Thr
130                 135                 140

Trp Lys Gly Thr Ala Gly His Arg Asp Pro Gly Asn Lys Ala Gly Met
145                 150                 155                 160

Thr Ser Leu Pro Gly Gly Pro Gln Ser Arg Gly Arg Glu Ala Arg
                165                 170                 175

Arg Thr Arg Lys Tyr Leu Glu Leu Tyr Ile Val Ala Asp His Thr Leu
                180                 185                 190

Phe Leu Thr Arg His Arg Asn Leu Asn His Thr Lys Gln Arg Leu Leu
        195                 200                 205

Glu Val Ala Asn Tyr Val Asp Gln Leu Leu Arg Thr Leu Asp Ile Gln
        210                 215                 220

Val Ala Leu Thr Gly Leu Glu Val Trp Thr Glu Arg Asp Arg Ser Arg
225                 230                 235                 240

Val Thr Gln Asp Ala Asn Ala Thr Leu Trp Ala Phe Leu Gln Trp Arg
                245                 250                 255

Arg Gly Leu Trp Ala Gln Arg Pro His Asp Ser Ala Gln Leu Leu Thr
                260                 265                 270

Gly Arg Ala Phe Gln Gly Ala Thr Val Gly Leu Ala Pro Val Glu Gly
        275                 280                 285

Met Cys Arg Ala Glu Ser Ser Gly Gly Val Ser Thr Asp His Ser Glu
        290                 295                 300

Leu Pro Ile Gly Ala Ala Ala Thr Met Ala His Glu Ile Gly His Ser
305                 310                 315                 320

Leu Gly Leu Ser His Asp Pro Asp Gly Cys Cys Val Glu Ala Ala Ala
                325                 330                 335

Glu Ser Gly Gly Cys Val Met Ala Ala Ala Thr Gly His Pro Phe Pro
        340                 345                 350

Arg Val Phe Ser Ala Cys Ser Arg Arg Gln Leu Arg Ala Phe Phe Arg
        355                 360                 365

Lys Gly Gly Gly Ala Cys Leu Ser Asn Ala Pro
        370                 375

<210> SEQ ID NO 51
<211> LENGTH: 379
<212> TYPE: PRT
<213> ORGANISM: homo sapiens

<400> SEQUENCE: 51

Leu Gln Gly His Ile Pro Gly Gln Pro Val Thr Pro His Trp Val Leu
1               5                   10                  15

Asp Gly Gln Pro Trp Arg Thr Val Ser Leu Glu Glu Pro Val Ser Lys
                20                  25                  30

Pro Asp Met Gly Leu Val Ala Leu Glu Ala Glu Gly Gln Glu Leu Leu
            35                  40                  45

Leu Glu Leu Glu Lys Asn His Arg Leu Leu Ala Pro Gly Tyr Ile Glu
        50                  55                  60

Thr His Tyr Gly Pro Asp Gly Gln Pro Val Val Leu Ala Pro Asn His
65                  70                  75                  80

Thr Asp His Cys His Tyr Gln Gly Arg Val Arg Gly Phe Pro Asp Ser
                85                  90                  95

Trp Val Val Leu Ala Thr Cys Ser Gly Met Ser Gly Leu Ile Thr Leu
            100                 105                 110
```

```
Ser Arg Asn Ala Ser Tyr Tyr Leu Arg Pro Trp Pro Arg Gly Ser
        115                 120                 125

Lys Asp Phe Ser Thr His Glu Ile Phe Arg Met Glu Gln Leu Leu Thr
130                 135                 140

Trp Lys Gly Thr Ala Gly His Arg Asp Pro Gly Asn Lys Ala Gly Met
145                 150                 155                 160

Thr Ser Leu Pro Gly Gly Pro Gln Ser Arg Gly Arg Arg Glu Ala Arg
                165                 170                 175

Arg Thr Arg Lys Tyr Leu Glu Leu Tyr Ile Val Ala Asp His Thr Leu
            180                 185                 190

Phe Leu Thr Arg His Arg Asn Leu Asn His Thr Lys Gln Arg Leu Leu
            195                 200                 205

Glu Val Ala Asn Tyr Val Asp Gln Leu Leu Arg Thr Leu Asp Ile Gln
        210                 215                 220

Val Ala Leu Thr Gly Leu Glu Val Trp Thr Glu Arg Asp Arg Ser Arg
225                 230                 235                 240

Val Thr Gln Asp Ala Asn Ala Thr Leu Trp Ala Phe Leu Gln Trp Arg
                245                 250                 255

Arg Gly Leu Trp Ala Gln Arg Pro His Asp Ser Ala Gln Leu Leu Thr
            260                 265                 270

Gly Arg Ala Phe Gln Gly Ala Thr Val Gly Leu Ala Pro Val Glu Gly
        275                 280                 285

Met Cys Arg Ala Glu Ser Ser Gly Gly Val Ser Thr Asp His Ser Glu
290                 295                 300

Leu Pro Ile Gly Ala Ala Ala Thr Met Ala His Glu Ile Gly His Ser
305                 310                 315                 320

Leu Gly Leu Ser His Asp Pro Asp Gly Cys Cys Val Glu Ala Ala Ala
                325                 330                 335

Glu Ser Gly Gly Cys Val Met Ala Ala Ala Thr Gly His Pro Phe Pro
            340                 345                 350

Arg Val Phe Ser Ala Cys Ser Arg Arg Gln Leu Arg Ala Phe Phe Arg
        355                 360                 365

Lys Gly Gly Gly Ala Cys Leu Ser Asn Ala Pro
370                 375

<210> SEQ ID NO 52
<211> LENGTH: 379
<212> TYPE: PRT
<213> ORGANISM: homo sapiens

<400> SEQUENCE: 52

Leu Gln Gly His Ile Pro Gly Gln Pro Val Thr Pro His Trp Val Leu
1               5                   10                  15

Asp Gly Gln Pro Trp Arg Thr Val Ser Leu Glu Glu Pro Val Ser Lys
                20                  25                  30

Pro Asp Met Gly Leu Val Ala Leu Glu Ala Glu Gly Gln Glu Leu Leu
            35                  40                  45

Leu Glu Leu Glu Lys Asn His Arg Leu Leu Ala Pro Gly Tyr Ile Glu
        50                  55                  60

Thr His Tyr Gly Pro Asp Gly Gln Pro Val Val Leu Ala Pro Asn His
65                  70                  75                  80

Thr Asp His Cys His Tyr Gln Gly Arg Val Arg Gly Phe Pro Asp Ser
                85                  90                  95

Trp Val Val Leu Cys Thr Cys Ser Gly Met Ser Gly Leu Ile Thr Leu
```

```
                100             105             110
Ser Arg Asn Ala Ser Tyr Tyr Leu Arg Pro Trp Pro Arg Gly Ser
            115                 120                 125

Lys Asp Phe Ser Thr His Glu Ile Phe Arg Met Glu Gln Leu Leu Thr
130                 135                 140

Trp Ile Gly Thr Ala Gly His Arg Asp Pro Gly Asn Lys Ala Gly Met
145                 150                 155                 160

Thr Ser Leu Pro Gly Gly Pro Gln Ser Arg Gly Arg Glu Ala Arg
            165                 170                 175

Arg Thr Arg Lys Tyr Leu Glu Leu Tyr Ile Val Ala Asp His Thr Leu
            180                 185                 190

Phe Leu Thr Arg His Arg Asn Leu Asn His Thr Lys Gln Arg Leu Leu
            195                 200                 205

Glu Val Ala Asn Tyr Val Asp Gln Leu Leu Arg Thr Leu Asp Ile Gln
            210                 215                 220

Val Ala Leu Thr Gly Leu Glu Val Trp Thr Glu Arg Asp Arg Ser Arg
225                 230                 235                 240

Val Thr Gln Asp Ala Asn Ala Thr Leu Trp Ala Phe Leu Gln Trp Arg
            245                 250                 255

Arg Gly Leu Trp Ala Gln Arg Pro His Asp Ser Ala Gln Leu Leu Thr
            260                 265                 270

Gly Arg Ala Phe Gln Gly Ala Thr Val Gly Leu Ala Pro Val Glu Gly
            275                 280                 285

Met Cys Arg Ala Glu Ser Ser Gly Gly Val Ser Thr Asp His Ser Glu
            290                 295                 300

Leu Pro Ile Gly Ala Ala Ala Thr Met Ala His Glu Ile Gly His Ser
305                 310                 315                 320

Leu Gly Leu Ser His Asp Pro Asp Gly Cys Cys Val Glu Ala Ala Ala
            325                 330                 335

Glu Ser Gly Gly Cys Val Met Ala Ala Ala Thr Gly His Pro Phe Pro
            340                 345                 350

Arg Val Phe Ser Ala Cys Ser Arg Arg Gln Leu Arg Ala Phe Phe Arg
            355                 360                 365

Lys Gly Gly Ala Cys Leu Ser Asn Ala Pro
370                 375

<210> SEQ ID NO 53
<211> LENGTH: 379
<212> TYPE: PRT
<213> ORGANISM: homo sapiens

<400> SEQUENCE: 53

Leu Gln Gly His Ile Pro Gly Gln Pro Val Thr Pro His Trp Val Leu
1               5                   10                  15

Asp Gly Gln Pro Trp Arg Thr Val Ser Leu Glu Glu Pro Val Ser Lys
            20                  25                  30

Pro Asp Met Gly Leu Val Ala Leu Glu Ala Glu Gly Gln Glu Leu Leu
            35                  40                  45

Leu Glu Leu Glu Lys Asn His Arg Leu Leu Ala Pro Gly Tyr Ile Glu
        50                  55                  60

Thr His Tyr Gly Pro Asp Gly Gln Pro Val Val Leu Ala Pro Asn His
65              70                  75                  80

Thr Asp His Cys His Tyr Gln Gly Arg Val Arg Gly Phe Pro Asp Ser
                85                  90                  95
```

```
Trp Val Val Leu Cys Thr Cys Ser Gly Met Ser Gly Leu Ile Thr Leu
            100                 105                 110

Ser Arg Asn Ala Ser Tyr Tyr Leu Arg Pro Trp Pro Pro Arg Gly Ser
            115                 120                 125

Lys Asp Phe Ser Thr His Glu Ile Phe Arg Met Glu Gln Leu Leu Thr
            130                 135                 140

Trp Lys Gly Thr Ala Gly His Arg Asn Pro Gly Asn Lys Ala Gly Met
145                 150                 155                 160

Thr Ser Leu Pro Gly Gly Pro Gln Ser Arg Gly Arg Glu Ala Arg
                165                 170                 175

Arg Thr Arg Lys Tyr Leu Glu Leu Tyr Ile Val Ala Asp His Thr Leu
            180                 185                 190

Phe Leu Thr Arg His Arg Asn Leu Asn His Thr Lys Gln Arg Leu Leu
            195                 200                 205

Glu Val Ala Asn Tyr Val Asp Gln Leu Leu Arg Thr Leu Asp Ile Gln
            210                 215                 220

Val Ala Leu Thr Gly Leu Glu Val Trp Thr Glu Arg Asp Arg Ser Arg
225                 230                 235                 240

Val Thr Gln Asp Ala Asn Ala Thr Leu Trp Ala Phe Leu Gln Trp Arg
            245                 250                 255

Arg Gly Leu Trp Ala Gln Arg Pro His Asp Ser Ala Gln Leu Leu Thr
            260                 265                 270

Gly Arg Ala Phe Gln Gly Ala Thr Val Gly Leu Ala Pro Val Glu Gly
            275                 280                 285

Met Cys Arg Ala Glu Ser Ser Gly Gly Val Ser Thr Asp His Ser Glu
            290                 295                 300

Leu Pro Ile Gly Ala Ala Ala Thr Met Ala His Glu Ile Gly His Ser
305                 310                 315                 320

Leu Gly Leu Ser His Asp Pro Asp Gly Cys Cys Val Glu Ala Ala Ala
            325                 330                 335

Glu Ser Gly Gly Cys Val Met Ala Ala Ala Thr Gly His Pro Phe Pro
            340                 345                 350

Arg Val Phe Ser Ala Cys Ser Arg Arg Gln Leu Arg Ala Phe Phe Arg
            355                 360                 365

Lys Gly Gly Gly Ala Cys Leu Ser Asn Ala Pro
    370                 375

<210> SEQ ID NO 54
<211> LENGTH: 379
<212> TYPE: PRT
<213> ORGANISM: homo sapiens

<400> SEQUENCE: 54

Leu Gln Gly His Ile Pro Gly Gln Pro Val Thr Pro His Trp Val Leu
1               5                   10                  15

Asp Gly Gln Pro Trp Arg Thr Val Ser Leu Glu Pro Val Ser Lys
            20                  25                  30

Pro Asp Met Gly Leu Val Ala Leu Glu Ala Glu Gly Gln Glu Leu Leu
            35                  40                  45

Leu Glu Leu Glu Lys Asn His Arg Leu Leu Ala Pro Gly Tyr Ile Glu
            50                  55                  60

Thr His Tyr Gly Pro Asp Gly Gln Pro Val Val Leu Ala Pro Asn His
65                  70                  75                  80

Thr Asp His Cys His Tyr Gln Gly Arg Val Arg Gly Phe Pro Asp Ser
            85                  90                  95
```

-continued

```
Trp Val Val Leu Cys Thr Cys Ser Gly Met Ser Gly Leu Ile Thr Leu
            100             105             110

Ser Arg Asn Ala Ser Tyr Tyr Leu Arg Pro Trp Pro Arg Gly Ser
        115             120             125

Lys Asp Phe Ser Thr His Glu Ile Phe Arg Met Glu Gln Leu Leu Thr
        130             135             140

Trp Lys Gly Thr Cys Gly His Arg Asp Pro Gly Asn Lys Ala Gly Met
145             150             155             160

Thr Ser Leu Pro Gly Gly Pro Gln Ser Arg Gly Arg Thr Glu Ala Arg
                165             170             175

Ser Thr Arg Lys Tyr Leu Glu Leu Tyr Ile Val Ala Asp His Thr Leu
            180             185             190

Phe Leu Thr Arg His Arg Asn Leu Asn His Thr Lys Gln Arg Leu Leu
        195             200             205

Glu Val Ala Asn Tyr Val Asp Gln Leu Leu Arg Thr Leu Asp Ile Gln
    210             215             220

Val Ala Leu Thr Gly Leu Glu Val Trp Thr Glu Arg Asp Arg Ser Arg
225             230             235             240

Val Thr Gln Asp Ala Asn Ala Thr Leu Trp Ala Phe Leu Gln Trp Arg
                245             250             255

Arg Gly Leu Trp Ala Gln Arg Pro His Asp Ser Ala Gln Leu Leu Thr
            260             265             270

Gly Arg Ala Phe Gln Gly Ala Thr Val Gly Leu Ala Pro Val Glu Gly
        275             280             285

Met Cys Arg Ala Glu Ser Ser Gly Gly Val Ser Thr Asp His Ser Glu
    290             295             300

Leu Pro Ile Gly Ala Ala Ala Thr Met Ala His Glu Ile Gly His Ser
305             310             315             320

Leu Gly Leu Ser His Asp Pro Asp Gly Cys Cys Val Glu Ala Ala Ala
                325             330             335

Glu Ser Gly Gly Cys Val Met Ala Ala Ala Thr Gly His Pro Phe Pro
            340             345             350

Arg Val Phe Ser Ala Cys Ser Arg Arg Gln Leu Arg Ala Phe Phe Arg
        355             360             365

Lys Gly Gly Gly Ala Cys Leu Ser Asn Ala Pro
370             375
```